United States Patent
Gennaro et al.

(10) Patent No.: US 12,145,998 B2
(45) Date of Patent: Nov. 19, 2024

(54) PERTUZUMAB VARIANTS AND EVALUATION THEREOF

(71) Applicant: Genentech, Inc., South San Francisco, CA (US)

(72) Inventors: Lynn A. Gennaro, San Mateo, CA (US); Yung-Hsiang Kao, San Mateo, CA (US); Yonghua Zhang, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 145 days.

(21) Appl. No.: 17/809,098

(22) Filed: Jun. 27, 2022

(65) Prior Publication Data

US 2023/0047103 A1     Feb. 16, 2023

Related U.S. Application Data

(60) Division of application No. 16/510,287, filed on Jul. 12, 2019, now abandoned, which is a continuation of application No. 15/788,598, filed on Oct. 19, 2017, now abandoned, which is a division of application No. 14/253,038, filed on Apr. 15, 2014, now Pat. No. 9,815,904.

(60) Provisional application No. 61/812,603, filed on Apr. 16, 2013.

(51) Int. Cl.
| | |
|---|---|
| *A61K 39/395* | (2006.01) |
| *C07K 16/30* | (2006.01) |
| *C07K 16/32* | (2006.01) |
| *G01N 33/68* | (2006.01) |
| *A61K 39/00* | (2006.01) |

(52) U.S. Cl.
CPC .............. *C07K 16/30* (2013.01); *C07K 16/32* (2013.01); *G01N 33/6854* (2013.01); *A61K 2039/505* (2013.01); *C07K 2317/41* (2013.01); *C07K 2317/55* (2013.01); *C07K 2317/567* (2013.01); *C07K 2317/73* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 4,968,603 A | 6/1990 | Slamon et al. | |
| 5,648,237 A | 7/1997 | Carter et al. | |
| 5,677,171 A | 10/1997 | Hudziak et al. | |
| 5,720,937 A | 2/1998 | Hudziak et al. | |
| 5,720,954 A | 2/1998 | Hudziak et al. | |
| 5,770,195 A | 6/1998 | Hudziak et al. | |
| 5,772,997 A | 6/1998 | Hudziak et al. | |
| 5,725,856 A | 10/1998 | Hudziak et al. | |
| 5,821,337 A | 10/1998 | Carter et al. | |
| 6,015,567 A | 1/2000 | Hudziak et al. | |
| 6,127,526 A | 3/2000 | Blank | |
| 6,054,297 A | 4/2000 | Carter et al. | |
| 6,165,464 A | 12/2000 | Hudziak et al. | |
| 6,267,958 B1 | 7/2001 | Andya et al. | |
| 6,333,169 B1 | 12/2001 | Hudziak et al. | |
| 6,333,398 B1 | 12/2001 | Blank | |
| 6,339,142 B1 | 1/2002 | Basey et al. | |
| 6,489,447 B1 | 3/2002 | Basey et al. | |
| 6,399,063 B1 | 4/2002 | Hudziak et al. | |
| 6,387,371 B1 | 5/2002 | Hudziak et al. | |
| 6,407,213 B1 | 6/2002 | Carter et al. | |
| 6,417,335 B1 | 9/2002 | Basey et al. | |
| 6,573,043 B1 | 3/2003 | Cohen et al. | |
| 6,627,196 B1 | 9/2003 | Baughman et al. | |
| 6,632,979 B2 | 10/2003 | Erickson et al. | |
| 6,639,055 B1 | 10/2003 | Carter et al. | |
| 6,685,940 B2 | 3/2004 | Andya et al. | |
| 6,719,971 B1 | 4/2004 | Carter et al. | |
| 6,800,738 B1 | 5/2004 | Carter et al. | |
| 6,797,814 B2 | 9/2004 | Blank | |
| 6,821,515 B1 | 11/2004 | Cleland et al. | |
| 6,905,830 B2 | 6/2005 | Cohen et al. | |
| 6,949,245 B1 | 9/2005 | Sliwkowski et al. | |
| 7,018,809 B1 | 3/2006 | Carter | |
| 7,060,268 B2 | 6/2006 | Andya et al. | |
| 7,097,840 B2 | 8/2006 | Erickson et al. | |

(Continued)

FOREIGN PATENT DOCUMENTS

| | | |
|---|---|---|
| WO | 2004/008099 A2 | 1/2004 |
| WO | 2005/000898 | 1/2005 |

(Continued)

OTHER PUBLICATIONS

Salas-Solano (CE Currents, 2008; LC-GC Europe; www.chromatographyonline.com; p. 615-622) in IDS.*

(Continued)

*Primary Examiner* — Laura B Goddard

(74) *Attorney, Agent, or Firm* — Wendy M. Lee

(57) ABSTRACT

The present application discloses variants of Pertuzumab. In particular, it discloses: an unpaired cysteine variant comprising Cys23/Cys88 unpaired cysteines in one or both variable light domains of Pertuzumab, an afucosylated variant of Pertuzumab, a low-molecular-weight-species (LMWS) of Pertuzumab, and a high-molecular-weight-species (HMWS) or Pertuzumab. The application further discloses the isolated variants, compositions, pharmaceutical compositions, and articles of manufacture comprising the variants, as well as methods of making and characterizing the variants and compositions thereof.

3 Claims, 42 Drawing Sheets

Specification includes a Sequence Listing.

(56) References Cited

U.S. PATENT DOCUMENTS

| | | |
|---|---|---|
| 7,041,292 B1 | 9/2006 | Sliwkowski et al. |
| 6,984,494 B2 | 10/2006 | Ralph |
| 7,129,051 B2 | 10/2006 | Cohen et al. |
| 7,074,404 B2 | 11/2006 | Basey et al. |
| 7,279,287 B2 | 9/2007 | Ralph |
| 7,344,840 B2 | 3/2008 | Cohen et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,184 B2 | 11/2008 | Allison et al. |
| 7,468,252 B2 | 12/2008 | Cohen et al. |
| 7,485,302 B2 | 3/2009 | Adams et al. |
| 7,485,704 B2 | 3/2009 | Fahrner et al. |
| 7,498,030 B2 | 3/2009 | Adams et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,501,122 B2 | 10/2009 | Adams et al. |
| 7,618,631 B2 | 11/2009 | Sliwkowski |
| 7,531,645 B2 | 12/2009 | Basey et al. |
| 7,682,609 B2 | 3/2010 | Andya et al. |
| 7,700,299 B2 | 4/2010 | Moecks et al. |
| 7,807,799 B2 | 5/2010 | Fahrner et al. |
| 7,846,441 B1 | 7/2010 | Hellmann |
| 7,674,589 B2 | 9/2010 | Cohen et al. |
| 7,811,773 B2 | 12/2010 | Ralph |
| 7,850,966 B2 | 12/2010 | Lowman et al. |
| 7,879,325 B2 | 1/2011 | Kao et al. |
| 7,892,549 B2 | 2/2011 | Paton et al. |
| 7,862,817 B2 | 4/2011 | Adams et al. |
| 7,919,254 B2 | 5/2011 | Cohen et al. |
| 7,981,418 B2 | 7/2011 | Amler et al. |
| 7,993,834 B2 | 9/2011 | Mass |
| 8,044,017 B2 | 10/2011 | Emery et al. |
| 8,075,890 B2 | 12/2011 | Carter et al. |
| 8,075,892 B2 | 12/2011 | Hellmann |
| 8,076,066 B2 | 12/2011 | Mass |
| 8,142,784 B2 | 3/2012 | Ebens, Jr. et al. |
| 8,163,287 B2 | 4/2012 | Sliwkowski et al. |
| 8,241,630 B2 | 8/2012 | Kao et al. |
| 8,247,397 B2 | 8/2012 | Belvin et al. |
| 8,309,087 B2 | 11/2012 | Hellmann |
| 8,333,964 B2 | 12/2012 | Agus et al. |
| 8,337,856 B2 | 12/2012 | Blattler et al. |
| 8,404,234 B2 | 3/2013 | Allison et al. |
| 8,597,654 B2 | 3/2013 | Bryant |
| 8,425,908 B2 | 4/2013 | Hellman |
| 8,440,402 B2 | 5/2013 | Mass |
| 8,529,901 B2 | 10/2013 | Hasmann et al. |
| 8,604,014 B2 | 10/2013 | Belvin et al. |
| 8,591,897 B2 | 11/2013 | Bryant |
| 8,592,152 B2 | 11/2013 | Mass |
| 8,372,396 B2 | 12/2013 | Andya et al. |
| 8,652,474 B2 | 2/2014 | Harris et al. |
| 8,652,479 B2 | 2/2014 | Ebens, Jr. et al. |
| 8,642,036 B2 | 4/2014 | Hellmann |
| 8,663,643 B2 | 4/2014 | Berry et al. |
| 8,710,196 B2 | 4/2014 | Emery et al. |
| 8,758,747 B2 | 6/2014 | Kallmeyer et al. |
| 8,691,232 B2 | 8/2014 | Derynck et al. |
| 8,840,896 B2 | 9/2014 | Lowman et al. |
| 8,937,161 B2 | 1/2015 | Mao et al. |
| 8,940,302 B2 | 1/2015 | Amler et al. |
| 9,017,671 B2 | 4/2015 | Andya et al. |
| 9,090,700 B2 | 7/2015 | Friess et al. |
| 9,107,926 B2 | 8/2015 | Belvin et al. |
| 9,180,185 B2 | 10/2015 | Bauss et al. |
| 9,180,189 B2 | 10/2015 | Andya et al. |
| 9,181,346 B2 | 10/2015 | Harris et al. |
| 9,249,218 B2 | 2/2016 | Basey et al. |
| 9,283,273 B2 | 3/2016 | Andya et al. |
| 9,345,661 B2 | 5/2016 | Adler et al. |
| 9,376,715 B2 | 6/2016 | Brophy et al. |
| 9,551,033 B2 | 1/2017 | Lee-Hoeflich et al. |
| 9,687,568 B2 | 6/2017 | Hasmann et al. |
| 9,815,904 B2 | 11/2017 | Gennaro et al. |
| 9,868,760 B2 | 1/2018 | Emery et al. |
| 9,896,478 B2 | 2/2018 | Lebreton et al. |
| 9,968,676 B2 | 5/2018 | Adler et al. |
| 9,969,811 B2 | 5/2018 | Gennaro et al. |
| 10,160,811 B2 | 12/2018 | Baughman et al. |
| 10,280,228 B2 | 5/2019 | Baughman et al. |
| 10,501,491 B2 | 12/2019 | Emery et al. |
| 10,689,457 B2 | 6/2020 | Paton et al. |
| 10,849,849 B2 | 12/2020 | Eng-Wong et al. |
| 11,077,189 B2 | 8/2021 | Benyunes et al. |
| 11,414,498 B2 | 8/2022 | Harris et al. |
| 11,638,756 B2 | 5/2023 | Benyunes et al. |
| 11,654,105 B2 | 5/2023 | Eng-Wong et al. |
| 11,655,305 B2 | 5/2023 | Paton et al. |
| 2001/0014326 A1 | 8/2001 | Andya et al. |
| 2002/0001587 A1 | 1/2002 | Erickson et al. |
| 2002/0035736 A1 | 3/2002 | Erickson et al. |
| 2002/0064785 A1 | 5/2002 | Mass |
| 2002/0090662 A1 | 7/2002 | Ralph |
| 2003/0078388 A1 | 4/2003 | Basey et al. |
| 2003/0086924 A1 | 5/2003 | Sliwkowski |
| 2003/0134344 A1 | 7/2003 | Mass |
| 2003/0147884 A1 | 8/2003 | Paton et al. |
| 2003/0152987 A1 | 8/2003 | Cohen et al. |
| 2003/0170234 A1 | 9/2003 | Hellmann |
| 2003/0170235 A1 | 9/2003 | Cohen et al. |
| 2003/0202972 A1 | 10/2003 | Andya et al. |
| 2004/0013667 A1 | 1/2004 | Kelsey et al. |
| 2004/0037823 A9 | 2/2004 | Paton et al. |
| 2004/0082047 A1 | 4/2004 | Emery et al. |
| 2004/0106161 A1 | 6/2004 | Bossenmaier et al. |
| 2004/0258685 A1 | 12/2004 | Brunetta et al. |
| 2005/0002928 A1 | 1/2005 | Hellmann |
| 2005/0063972 A1 | 3/2005 | Basey et al. |
| 2005/0100944 A1 | 5/2005 | Cohen et al. |
| 2005/0208043 A1 | 9/2005 | Adams et al. |
| 2005/0238640 A1 | 10/2005 | Sliwkowski |
| 2005/0244417 A1 | 11/2005 | Ashkenazi et al. |
| 2005/0244929 A1 | 11/2005 | Carter |
| 2005/0276812 A1 | 12/2005 | Ebens et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0046270 A1 | 3/2006 | Ralph |
| 2006/0067930 A1 | 3/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya |
| 2006/0099201 A1 | 5/2006 | Andya et al. |
| 2006/0121044 A1 | 6/2006 | Amler |
| 2006/0165702 A1 | 7/2006 | Allison et al. |
| 2006/0275305 A1 | 7/2006 | Bryant |
| 2006/0182739 A1 | 8/2006 | Basey et al. |
| 2006/0183150 A1 | 8/2006 | Cohen et al. |
| 2006/0188509 A1 | 8/2006 | Derynck |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman |
| 2006/0212956 A1 | 9/2006 | Crocker et al. |
| 2006/0216285 A1 | 9/2006 | Adams et al. |
| 2006/0228745 A1 | 12/2006 | Mass |
| 2006/0292158 A1 | 12/2006 | Aoki et al. |
| 2007/0020261 A1 | 1/2007 | Sliwkowski et al. |
| 2007/0026001 A1 | 1/2007 | Ashkenazi et al. |
| 2007/0037228 A1 | 2/2007 | Moecks et al. |
| 2007/0166753 A1 | 7/2007 | Mass |
| 2007/0202516 A1 | 8/2007 | Mass et al. |
| 2007/0184055 A1 | 9/2007 | Sliwkowski |
| 2007/0224203 A1 | 9/2007 | Friess |
| 2007/0009976 A1 | 11/2007 | Lenz |
| 2007/0269429 A1 | 11/2007 | Kelsey et al. |
| 2007/0292419 A1 | 12/2007 | Hellmann |
| 2008/0102069 A1 | 1/2008 | Friess et al. |
| 2008/0038271 A1 | 2/2008 | Amler et al. |
| 2008/0050373 A1 | 2/2008 | Cohen |
| 2008/0050385 A1 | 2/2008 | Friess et al. |

(56) References Cited

U.S. PATENT DOCUMENTS

| | | |
|---|---|---|
| 2008/0050748 A1 | 2/2008 | Cohen et al. |
| 2008/0003827 A1 | 3/2008 | Dijksman |
| 2008/0160026 A1 | 3/2008 | Ashkenazi et al. |
| 2008/0112957 A1 | 5/2008 | Fendly et al. |
| 2008/0112958 A1 | 5/2008 | Mass |
| 2008/0171040 A1 | 7/2008 | Ebens et al. |
| 2008/0187533 A1 | 7/2008 | Hellmann |
| 2008/0108096 A1 | 8/2008 | Ralph |
| 2008/0226659 A1 | 9/2008 | Erickson et al. |
| 2008/0241146 A1 | 10/2008 | Ashkenazi et al. |
| 2008/0286280 A1 | 11/2008 | Kallmeyer et al. |
| 2008/0317753 A1 | 12/2008 | Amler et al. |
| 2009/0068178 A1 | 3/2009 | Crowley |
| 2009/0081223 A1 | 3/2009 | Allison |
| 2009/0087432 A1 | 4/2009 | Sliwkowski |
| 2009/0098135 A1 | 4/2009 | Belvin |
| 2009/0099344 A1 | 4/2009 | Fahrner et al. |
| 2009/0148402 A1 | 6/2009 | Brunetta et al. |
| 2009/0148435 A1 | 6/2009 | Lebreton et al. |
| 2009/0155259 A1 | 6/2009 | Derynck |
| 2009/0155803 A1 | 6/2009 | Cohen et al. |
| 2009/0187007 A1 | 7/2009 | Lowmen |
| 2009/0202536 A1 | 8/2009 | Ebens et al. |
| 2009/0202546 A1* | 8/2009 | Harris .................. A61P 15/00 424/139.1 |
| 2009/0220492 A1 | 9/2009 | Basey et al. |
| 2009/0226455 A1 | 9/2009 | Filvaroff |
| 2009/0239236 A1 | 9/2009 | Mass |
| 2009/0285837 A1 | 11/2009 | Kao |
| 2009/0317387 A1 | 12/2009 | Paton et al. |
| 2010/0008975 A1 | 1/2010 | Amler et al. |
| 2010/0015157 A1 | 1/2010 | Andya |
| 2010/0016556 A1 | 1/2010 | Carter et al. |
| 2010/0112603 A1 | 5/2010 | Moecks et al. |
| 2010/0120053 A1 | 5/2010 | Cohen et al. |
| 2010/0158899 A1 | 6/2010 | Andya et al. |
| 2010/0196363 A1 | 8/2010 | Vanhauwere et al. |
| 2010/0285010 A1 | 11/2010 | Friess |
| 2010/0298156 A1 | 11/2010 | Lee-Hoeflich |
| 2011/0044977 A1 | 2/2011 | Adler et al. |
| 2011/0129464 A1 | 2/2011 | Adams et al. |
| 2011/0027190 A1 | 3/2011 | Hasmann et al. |
| 2011/0064736 A1 | 3/2011 | Friess et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0151454 A1 | 6/2011 | Lee-Hoeflich |
| 2011/0159014 A1 | 6/2011 | Lowman et al. |
| 2011/0245103 A1 | 6/2011 | Amler et al. |
| 2011/0246399 A1 | 6/2011 | Amler et al. |
| 2011/0165157 A1 | 7/2011 | Derynck |
| 2011/0223159 A1 | 9/2011 | Friess et al. |
| 2011/0223619 A1 | 9/2011 | Belvin |
| 2011/0236383 A1 | 9/2011 | Andya et al. |
| 2011/0033460 A1 | 10/2011 | Fendly et al. |
| 2011/0250194 A1 | 10/2011 | Hellmann |
| 2011/0311556 A1 | 12/2011 | Gaucher et al. |
| 2012/0065381 A1 | 3/2012 | Emery |
| 2012/0107302 A1 | 3/2012 | Berry et al. |
| 2012/0107391 A1 | 3/2012 | Kelsey |
| 2012/0093838 A1 | 4/2012 | Mass |
| 2012/0251530 A1 | 4/2012 | Sliwkowski et al. |
| 2012/0003217 A1 | 5/2012 | Bryant |
| 2012/0121586 A1 | 5/2012 | Kiermaier et al. |
| 2012/0034213 A1 | 9/2012 | Hellmann |
| 2012/0034609 A1 | 9/2012 | Mass |
| 2013/0195845 A1 | 1/2013 | Fendly et al. |
| 2013/0195851 A1 | 1/2013 | Alavattam et al. |
| 2013/0039909 A1 | 2/2013 | Amler |
| 2013/0108620 A1 | 2/2013 | Blattler et al. |
| 2013/0071384 A1 | 3/2013 | Andya et al. |
| 2013/0095172 A1 | 4/2013 | Alavattam et al. |
| 2013/0323180 A1 | 5/2013 | Hasmann et al. |
| 2013/0142865 A1 | 6/2013 | Allison et al. |
| 2013/0149299 A1 | 6/2013 | Baughman et al. |
| 2013/0183292 A1 | 7/2013 | Friess et al. |
| 2013/0209459 A1 | 8/2013 | Hellmann |
| 2013/0216532 A1 | 8/2013 | Adler et al. |
| 2013/0224185 A1 | 8/2013 | Andya et al. |
| 2013/0345217 A1 | 12/2013 | Belvin et al. |
| 2014/0018523 A1 | 1/2014 | Basey et al. |
| 2014/0044704 A1 | 2/2014 | Paton et al. |
| 2014/0044706 A1 | 2/2014 | Belvin |
| 2014/0044709 A1 | 2/2014 | Klencke et al. |
| 2014/0079692 A1 | 3/2014 | Baughman et al. |
| 2014/0086940 A1 | 3/2014 | Bryant |
| 2014/0093458 A1 | 3/2014 | Dobosz et al. |
| 2014/0186343 A1 | 3/2014 | Harris et al. |
| 2014/0186347 A1 | 3/2014 | Derynck et al. |
| 2014/0186867 A1 | 3/2014 | Harris et al. |
| 2014/0248274 A1 | 4/2014 | Kallmeyer et al. |
| 2014/0248609 A1 | 4/2014 | Mass |
| 2014/0140993 A1 | 5/2014 | Ross et al. |
| 2014/0212411 A1 | 7/2014 | Blattler et al. |
| 2014/0128580 A1 | 8/2014 | Ebens, Jr. et al. |
| 2014/0227255 A1 | 8/2014 | Bauss et al. |
| 2014/0308277 A1 | 10/2014 | Gennaro et al. |
| 2014/0322202 A1 | 10/2014 | Cohen |
| 2014/0341886 A1 | 11/2014 | Hellmann |
| 2015/0273059 A1 | 1/2015 | Derynck et al. |
| 2015/0056196 A1 | 2/2015 | Lebreton et al. |
| 2015/0093381 A1 | 2/2015 | Allison et al. |
| 2015/0079076 A1 | 3/2015 | Brophy et al. |
| 2015/0086545 A1 | 3/2015 | Sliwkowski et al. |
| 2015/0110816 A1 | 4/2015 | Blattler et al. |
| 2015/0111211 A1 | 4/2015 | Amler et al. |
| 2015/0150970 A1 | 4/2015 | Mass |
| 2015/0037332 A1 | 5/2015 | Paton et al. |
| 2015/0196642 A1 | 7/2015 | Andya et al. |
| 2015/0239969 A1 | 8/2015 | Friess et al. |
| 2015/0283238 A1 | 8/2015 | Friess et al. |
| 2015/0252113 A1 | 10/2015 | Fendly et al. |
| 2015/0072918 A1 | 12/2015 | Emery et al. |
| 2016/0045515 A1 | 2/2016 | Belvin et al. |
| 2016/0060353 A1 | 3/2016 | Lowman et al. |
| 2016/0175438 A1 | 6/2016 | Alavattam et al. |
| 2016/0376377 A1 | 12/2016 | Basey et al. |
| 2017/0073777 A1 | 3/2017 | Lee-Hoeflich et al. |
| 2017/0106097 A1 | 4/2017 | Blattler et al. |
| 2017/0136026 A1 | 5/2017 | Sliwkowski et al. |
| 2017/0166656 A1 | 6/2017 | Lowman et al. |
| 2017/0190786 A1 | 6/2017 | Fendly et al. |
| 2017/0035907 A1 | 9/2017 | Green et al. |
| 2017/0037147 A1 | 9/2017 | Allison et al. |
| 2017/0226224 A1 | 10/2017 | Basey et al. |
| 2017/0008971 A1 | 12/2017 | Dennis et al. |
| 2018/0118781 A1 | 3/2018 | Lebreton et al. |
| 2018/0280408 A1 | 4/2018 | Belvin et al. |
| 2018/0282428 A1 | 4/2018 | Fendly et al. |
| 2018/0134803 A1 | 5/2018 | Douthwaite et al. |
| 2018/0162951 A1 | 6/2018 | Cohen |
| 2018/0251536 A1 | 6/2018 | Friess et al. |
| 2018/0251557 A1 | 6/2018 | Chui et al. |
| 2018/0201692 A1 | 7/2018 | Lowman et al. |
| 2018/0037661 A1 | 8/2018 | Gennaro et al. |
| 2018/0037662 A1 | 8/2018 | Gennaro et al. |
| 2018/0228895 A1 | 8/2018 | Adler et al. |
| 2018/0236072 A1 | 8/2018 | Derynck et al. |
| 2018/0236093 A1 | 8/2018 | Bryant |
| 2018/0244715 A1 | 8/2018 | Emery et al. |
| 2018/0221481 A1 | 9/2018 | Beattie et al. |
| 2018/0221488 A1 | 9/2018 | Andya et al. |
| 2018/0274038 A1 | 9/2018 | Belousov et al. |
| 2018/0327510 A1 | 11/2018 | Allison et al. |
| 2019/0055317 A1 | 2/2019 | Baughman et al. |
| 2019/0298861 A1 | 3/2019 | Dobosz et al. |
| 2019/0117769 A1 | 4/2019 | Benyunes et al. |
| 2019/0070291 A1 | 7/2019 | Mass |
| 2019/0240185 A1 | 8/2019 | Desmond-Hellman et al. |
| 2019/0322761 A1 | 10/2019 | Harris |
| 2019/0323089 A1 | 10/2019 | Lee-Hoeflich et al. |
| 2019/0345258 A1 | 11/2019 | Gennaro et al. |
| 2019/0352331 A1 | 11/2019 | Emery et al. |
| 2019/0352332 A1 | 11/2019 | Emery et al. |

(56) References Cited

U.S. PATENT DOCUMENTS

| | | |
|---|---|---|
| 2019/0352333 A1 | 11/2019 | Emery et al. |
| 2019/0374547 A1 | 12/2019 | Sliwkowski et al. |
| 2020/0048362 A1 | 2/2020 | Blattler et al. |
| 2020/0206348 A1 | 2/2020 | Benyunes et al. |
| 2020/0376120 A1 | 3/2020 | Benyunes et al. |
| 2020/0155701 A1 | 5/2020 | Bryant |
| 2020/0157238 A1 | 5/2020 | Gennaro et al. |
| 2020/0199690 A1 | 6/2020 | Belousov et al. |
| 2020/0246267 A1 | 6/2020 | Haas et al. |
| 2020/0237910 A1 | 7/2020 | Beattie et al. |
| 2020/0239595 A1 | 7/2020 | Allison et al. |
| 2020/0179515 A1 | 11/2020 | Andya et al. |
| 2021/0015919 A1 | 1/2021 | Benyunes et al. |
| 2021/0047429 A1 | 2/2021 | Paton et al. |
| 2021/0085597 A1 | 3/2021 | Eng-Wong et al. |
| 2021/0130398 A1 | 6/2021 | Emery et al. |
| 2021/0130399 A1 | 6/2021 | Emery et al. |
| 2021/0171571 A1 | 10/2021 | Emery et al. |
| 2021/0330789 A1 | 10/2021 | Benyunes et al. |
| 2021/0042016 A1 | 11/2021 | Chui et al. |
| 2021/0353753 A1 | 11/2021 | Adler et al. |
| 2021/0403599 A1 | 12/2021 | Badovinac-Crnjevic et al. |
| 2022/0170115 A1 | 2/2022 | Belousov et al. |
| 2022/0090212 A1 | 3/2022 | Belousov et al. |
| 2022/0282337 A1 | 8/2022 | Belousov et al. |
| 2022/0362379 A1 | 11/2022 | Benyunes et al. |
| 2023/0212311 A1 | 7/2023 | Allison et al. |
| 2023/0250187 A1 | 8/2023 | Paton et al. |
| 2023/0263895 A1 | 8/2023 | Andya et al. |
| 2023/0277663 A1 | 9/2023 | Ross et al. |
| 2023/0277664 A1 | 9/2023 | Ross et al. |
| 2023/0310455 A1 | 10/2023 | Schutzman et al. |
| 2023/0314420 A1 | 10/2023 | Avenal et al. |
| 2023/0416401 A1 | 12/2023 | Harris et al. |
| 2024/0252634 A1 | 8/2024 | Benyunes et al. |
| 2024/0262932 A1 | 8/2024 | Harris et al. |
| 2024/0269064 A1 | 8/2024 | Eng-Wong et al. |

FOREIGN PATENT DOCUMENTS

| | | |
|---|---|---|
| WO | 2008/116149 A2 | 9/2008 |
| WO | 2008/116149 A3 | 9/2008 |
| WO | 2009/009523 A2 | 1/2009 |
| WO | 2009/099545 | 8/2009 |
| WO | 2009/099719 A2 | 8/2009 |
| WO | 2009/099829 A1 | 8/2009 |
| WO | 2011/069074 A2 | 6/2011 |
| WO | 2011/076683 A1 | 6/2011 |
| WO | 2011/146568 A1 | 11/2011 |
| WO | 2011/146568 A8 | 11/2011 |
| WO | 2012/092612 A1 | 7/2012 |
| WO | 2012/100343 | 8/2012 |
| WO | 2012/120004 A1 | 9/2012 |
| WO | 2013/083810 A1 | 6/2013 |
| WO | 2014/083178 A1 | 6/2014 |
| WO | 2014/108484 A2 | 7/2014 |
| WO | 2015/095418 A1 | 6/2015 |
| WO | 2022/013189 A1 | 1/2022 |
| WO | 2022/125483 A1 | 6/2022 |
| WO | 2023/178019 A1 | 9/2023 |

OTHER PUBLICATIONS

Michels et al (Electrophoresis, Mar. 2012, 33:815-826) in IDS.*
Felten and Salas-Solano (Part I) (Beckman Coulter, 2010, pp. 1-8) in IDS.*
Felten and Salas-Solano (Part II) (Beckman Coulter, 2011, pp. 1-6) in IDS.*
Yamamoto et al (Jpn J Clinical Oncology, 2009, 39:260-266) (IDS).*
CSCO—Chinese Society Clinical Oncology et al., "Guidelines of the Chinese Society of Clinical Oncology [CSCO]—Breast Cancer" People's Medical Publishing House-Beijing (Excerpt pp. 12, 14—Chinese w/Eng. Translation),: 12, 14 (Jan. 1, 2022).

Adams et al., "Humanization of a recombinant monoclonal antibody to produce a therapeutic HER dimerization inhibitor, pertuzumab" Cancer Immunol Immunother. 55(6):717-727 ( 2006).
Baselga, J. et al., "Phase II Trial of Pertuzumab and Trastuzumab in Patients with Human Epidermal Growth Factor Receptor 2-Positive Metastatic Breast Cancer That Progressed During Prior Trastuzumab Therapy" J Clin Oncl 28(7):1138-1144 (Mar. 1, 2010).
Chumsae, C., et al., "Identification and Localization of Unpaired Cysteine Residues in Monoclonal Antibodies by Fluorescence Labeling and Mass Spectrometry" Anal Chem 81(15):6449-6457 (Aug. 1, 2009).
Chung et al., "Quantitative evaluation of fucose reducing effects in a humanized antibody on Fcγ receptor binding and antibody-dependent cell-mediated cytotoxicity activities" mAbs 4(3):326-340 ( 2012).
Diederich et al., "A sub-two minutes method for monoclonal antibody-aggregate quantification using parallel interlaced size exclusion high performance liquid chromatography" Journal of Chromatography A 1218(50):9010-9018 (Dec. 16, 2011).
Ellman, "Tissue sulfhydryl groups" Arch. Biochem. Biophys. 82:70-77 ( 1959).
European Medicines Agency, Committee for Medicinal Products for Human Use, Perjeta Assessment Report, Procedure No. EMEA/H/C/002547/000, pgs.pp. 1-123 (Dec. 13, 2012).
Felten and Salas-Solano, "Capillary Electrophoresis in Quality Control: Part Ii: Ce-Sds Method Development and Robustness" Beckman Coulter:1-6 ( 2011).
Felten and Salas-Solano, "Capillary Electrophoresis in Quality Control: Part I: Application for Therapeutic Proteins" Beckman Coulter:1-8 ( 2010).
Fisher et al., "MythBusters: Could a Fragment Peak be Identified in a Reduced CE-SDS Profile?" Slides pp. 1-22 ( Oct. 3, 2012).
Flynn et al., "Naturally occurring glycan forms of human immunoglobulins G1 and G2" Mol Immunol. 47(11-12):2074-82 ( 2010).
Gabrielson et al., "Measuring low levels of protein aggregation by sedimentation velocity" Methods 54(1):83-91 ( 2011).
Genentech, Inc., 'Genentech reports additional data from biooncology pipeline at ASCO' (press release), pp. 1-2 ( Jun. 1, 2003).
Glover, Z.W., et al., "Compatibility and stability of pertuzumab and trastuzumab admixtures in I.V. infusion bags for coadministration" J Pharma Sci 102(3):794-812 (Mar. 1, 2013).
Harris, "Heterogeneity of recombinant antibodies: linking structure to function" Dev Biol Basel). 122:117-127 ( 2005).
Hunt et al., "Capillary electrophoresis sodium dodecyl sulfate nongel sieving analysis of a therapeutic recombinant monoclonal antibody: a biotechnology perspective" Anal Chem. 71(13):2390-7 ( 1999).
Junttila et al., "Superior in vivo efficacy of afucosylated trastuzumab in the treatment of HER2-amplified breast cancer" Cancer Research 70(11):4481-4489 (Jun. 1, 2010).
Kanda, Y., et al., "Comparison of cell lines for stable production of fucose-negative antibodies with enhanced ADCC" Biotechnol Bioeng 94(4):680-688 (Jul. 5, 2006).
Lin, "A concordance correlation coefficient to evaluate reproducibility" Biometrics 45(1):255-68 ( 1989).
Ma et al., "Analysis of Protein Therapeutics by Capillary Electrophoresis" Chromatographia Supplement 53:S75-S89 ( 2001).
Ma et al., "Carbohydrate analysis of a chimeric recombinant monoclonal antibody by capillary electrophoresis with laser-induced fluorescence detection" Anal Chem. 71(22):5185-92 (1999).
Michels et al., "Quantitative impurity analysis of monoclonal antibody size heterogeneity by CE-LIF: Example of development and validation through a quality-by-design framework" Electrophoresis, www.electrophoresis-journal.com 33:815-826 (Mar. 2012).
Moreno et al., "High-Throughput Multi-Product Liquid Chromatography for Characterization of Monoclonal Antibodies" BioPharm International 23(11):pp. 1-17 http://www.biopharminternational.com/high-throughput-multi-product-liquid-chromatography-characterization-monoclonal-antibodies-0 Nov. 1, 2010.
National Research Council et al. Monoclonal Antibody Production "Chapter 5: Large-Scale Production of Monoclonal Antibodies" Committee on Methods of Producing Monoclonal Antibodies, Insti-

(56) References Cited

OTHER PUBLICATIONS tute for Laboratory Animal Research, Washington, DC—USA:National Academy Press,:25-32 ( 1999) https://www.ncbi.nlm.nih.gov/books/NBK100189/.

Page et al., "A New Fluorometric Assay for Cytotoxicity Measurements In Vitro." Int J Oncol 3:473-476 ( 1993).

PERJETA® (pertuzumab) Full Prescribing Information, pp. 1-15 (revised Jun. 2012).

Reichert, J.,, "Marketed therapeutic antibodies compendium" MABS 4(3):413-415 (May 1, 2012).

Salas-Solano et al., "Optimization and Validation of a Quantitative Capillary Electrophoresis Sodium Dodecyl Sulfate Method for Quality Control and Stability Monitoring of Monoclonal Antibodies" Analytical Chemistry 78(18):6583-94 ( 2006).

Salas-Solano et al., "Optimization Approaches in the Routine Analysis of Monoclonal Antibodies by Capillary Electrophoresis" CE Currents, www.chromatographyonline.com:615-622 (2008).

Stackhouse et al., "A high-throughput UPLC method for the characterization of chemical modifications in monoclonal antibody molecules" Journal of Pharmaceutical Sciences 100(12):5115-5125 (Dec. 2011).

Xiang et al., "Localization and Quantitation of Free Sulfhydryl in Recombinant Monoclonal Antibodies by Differential Labeling with 12C and 13C Iodoacetic Acid and LC-MS Analysis" 81(19):8101-8108 (Oct. 1, 2009).

Yamamoto et al., "Phase I and Pharmacokinetic Study of HER2-targeted rhuMAb 2C4 (Pertuzumab, RO4368451) in Japanese Patients with Solid Tumors" Jpn J. Clin Oncol 39(4):260-266 ( 2009).

Yamane-Ohnuki et al., "Production of Therapeutic Antibodies with Controlled Fucosylation" mABs 1(3):230-236 ( 2009).

Zhang et al., "Identification and characterization of buried unpaired cysteines in a recombinant monoclonal IgG1 antibody" Anal Chem. 84(16):7112-7123 ( 2012).

\* cited by examiner

Variable Light

```
                    10         20         30          40
2C4      DTVMTQSHKIMSTSVGDRVSITC [KASQDVSIGVA] WYQQRP
         **  **** *            *                   *
574      DIQMTQSPSSLSASVGDRVTITC [KASQDVSIGVA] WYQQKP
                                   *  ** ***
hum κI   DIQMTQSPSSLSASVGDRVTITC [RASQSISNYLA] WYQQKP 50          60         0          80
2C4      GQSPKLLIY [SASYRYT] GVPDRFTGSGSGTDFTFTISSVQA
         **                      *  *         *    * *
574      GKAPKLLIY [SASYRYT] GVPSRFSGSGSGTDFTLTISSLQP
                    * *****
hum κI   GKAPKLLIY [AASSLES] GVPSRFSGSGSGTDFTLTISSLQP 90         100
2C4      EDLAVYYC [QQYYIYPYT] FGGGTKLEIK (SEQ ID NO:5)
          * *                  *    *
574      EDFATYYC [QQYYIYPYT] FGQGTKVEIK (SEQ ID NO:7)
                   *** *
hum κI   EDFATYYC [QQYNSLPWT] FGQGTKVEIK (SEQ ID NO:9)
```

FIG. 2A

Variable Heavy

```
                     10         20         30          40
2C4       EVQLQQSGPELVKPGTSVKISCKAS [GFTFTDYTMD] WVKQS
           **   **   *  *  ***  *                * *
574       EVQLVESGGGLVQPGGSLRLSCAAS [GFTFTDYTMD] WVRQA
                                      **  *
hum III   EVQLVESGGGLVQPGGSLRLSCAAS [GFTFSSYAMS] WVRQA 50       a     60             70         80
2C4       HGKSLEWIG [DVNPNSGGSIYNQRFKG] KASLTVDRSSRIVYM
          *   *  **                     *** *     **** *
574       PGKGLEWVA [DVNPNSGGSIYNQRFKG] RFTLSVDRSKNTLYL
                     ****** *** ****     *  *
hum III   PGKGLEWVA [VISGDGGSTYYADSVKG] RFTISRDNSKNTLYL abc      90        100ab         110
2C4       ELRSLTFEDTAVYYCAR [NLGPSFYFDY] WGQGTTLTVSS (SEQ ID NO:6)
          ***   **                                **
574       QMNSLRAEDTAVYYCAR [NLGPSFYFDY] WGQGTLVTVSS (SEQ ID NO:8)
                                ********
hum III   QMNSLRAEDTAVYYCAR [GRVGYSLYDY] WGQGTLVTVSS (SEQ ID NO:10)
```

FIG. 2B

Amino Acid Sequence for Pertuzumab Light Chain

```
  1         10        20        30        40        50        60
  |         |         |         |         |         |         |
DIQMTQSPSSLSASVGDRVTITCKASQDVSIGVAWYQQKPGKAPKLLIYSASYRYTGVPS 70        80        90       100       110       120
            |         |         |         |         |         |
RFSGSGSGTDFTLTISSLQPEDFATYYCQQYYIYPYTFGQGTKVEIKRTVAAPSVFIFPP 130       140       150       160       170       180
            |         |         |         |         |         |
SDEQLKSGTASVVCLLNNFYPREAKVQWKVDNALQSGNSQESVTEQDSKDSTYSLSSTLT 190       200       210
            |         |         |
LSKADYEKHKVYACEVTHQGLSSPVTKSFNRGEC (SEQ ID NO: 11)
```

*FIG. 3A*

Amino Acid Sequence for Pertuzumab Heavy Chain

```
  1         10        20        30        40        50        60
  |         |         |         |         |         |         |
EVQLVESGGGLVQPGGSLRLSCAASGFTFTDYTMDWVRQAPGKGLEWVADVNPNSGGSIY 70        80        90       100       110       120
            |         |         |         |         |         |
NQRFKGRFTLSVDRSKNTLYLQMNSLRAEDTAVYYCARNLGPSFYFDYWGQGTLVTVSSA 130       140       150       160       170       180
            |         |         |         |         |         |
STKGPSVFPLAPSSKSTSGGTAALGCLVKDYFPEPVTVSWNSGALTSGVHTFPAVLQSSG 190       200       210       220       230       240
            |         |         |         |         |         |
LYSLSSVVTVPSSSLGTQTYICNVNHKPSNTKVDKKVEPKSCDKTHTCPPCPAPELLGGP 250       260       270       280       290       300
            |         |         |         |         |        *|
SVFLFPPKPKDTLMISRTPEVTCVVVDVSHEDPEVKFNWYVDGVEVHNAKTKPREEQYNS 310       320       330       340       350       360
            |         |         |         |         |         |
TYRVVSVLTVLHQDWLNGKEYKCKVSNKALPAPIEKTISKAKGQPREPQVYTLPPSREEM 370       380       390       400       410       420
            |         |         |         |         |         |
TKNQVSLTCLVKGFYPSDIAVEWESNGQPENNYKTTPPVLDSDGSFFLYSKLTVDKSRWQ 430       440       448
            |         |         |
QGNVFSCSVMHEALHNHYTQKSLSLSPG   (SEQ ID NO: 12)
```

*FIG. 3B*

Trastuzmab Light Chain

```
  1                                              15                              30                                45
  D I Q M T Q S P S S L S A S V G D R V T I T C R A S Q D V N T A V A W Y Q Q K P G K A P K
 46                                             60                              75                                90
  L L I Y S A S F L Y S G V P S R F S G S R S G T D F T L T I S S L Q P E D F A T Y Y C Q Q
 91                                            105                             120                               135
  H Y T T P P T F G Q G T K V E I K R T V A A P S V F I F P P S D E Q L K S G T A S V V C L
136                                            150                             165                               180
  L N N F Y P R E A K V Q W K V D N A L Q S G N S Q E S V T E Q D S K D S T Y S L S S T L T
181                                            195                             210  214
  L S K A D Y E K H K V Y A C E V T H Q G L S S P V T K S F N R G E C   (SEQ ID NO: 13)
```

*FIG. 4A*

Trastuzmab Heavy Chain

```
1                                               45
EVQLVESGGGLVQPGGSLRLSCAASGFNIKDTYIHWVRQAPGKGL
46                                              90
EWVARIYPTNGYTRYADSVKGRFTISADTSKNTAYLQMNSLRAED
91                                              135
TAVYYCSRWGGDGFYAMDYWGQGTLVTVSSASTKGPSVFPLAPSS
136                                             180
KSTSGGTAALGCLVKDYFPEPVTVSWNSGALTSGVHTFPAVLQSS
181                                             225
GLYSLSSVVTVPSSSLGTQTYICNVNHKPSNTKVDKKVEPKSCDK
226                                             270
THTCPPCPAPELLGGPSVFLFPPKPKDTLMISRTPEVTCVVVDVS
271                                             315
HEDPEVKFNWYVDGVEVHNAKTKPREEQYNSTYRVVSVLTVLHQD
316                                             360
WLNGKEYKCKVSNKALPAPIEKTISKAKGQPREPQVYTLPPSREE
361                                             405
MTKNQVSLTCLVKGFYPSDIAVEWESNGQPENNYKTTPPVLDSDG
406                                             449
SFFLYSKLTVDKSRWQQGNVFSCSVMHEALHNHYTQKSLSLSPG
```

(SEQ ID NO: 14)

FIG. 4B

Pertuzumab Variant Light Chain

```
1                          15                          30                          45
V H S D I Q M T Q S P S S L S A S V G D R V T I T C K A S Q D V S I G V A W Y Q Q K P G K
46                         60                          75                          90
A P K L L I Y S A S Y R Y T G V P S R F S G S G S G T D F T L T I S S L Q P E D F A T Y Y
91                         105                         120                         135
C Q Q Y Y I Y P Y T F G Q G T K V E I K R T V A A P S V F I F P P S D E Q L K S G T A S V
136                        150                         165                         180
V C L L N N F Y P R E A K V Q W K V D N A L Q S G N S Q E S V T E Q D S K D S T Y S L S S
181                        195                         210  217
T L T L S K A D Y E K H K V Y A C E V T H Q G L S S P V T K S F N R G E C   (SEQ ID NO: 15)
```

FIG. 5A

Pertuzumab Variant Heavy Chain

```
1   E V Q L V E S G G G L V Q P G G S L R L S C A A S G F T F T D Y T M D W V R Q A P G K G L   45
46  E W V A D V N P N S G G S I Y N Q R F K G R F T L S V D R S K N T L Y L Q M N S L R A E D   90
91  T A V Y Y C A R N L G P S F Y F D Y W G Q G T L V T V S S A S T K G P S V F P L A P S S K   135
136 S T S G G T A A L G C L V K D Y F P E P V T V S W N S G A L T S G V H T F P A V L Q S S G   180
181 L Y S L S S V V T V P S S S L G T Q T Y I C N V N H K P S N T K V D K K V E P K S C D K T   225
226 H T C P P C P A P E L L G G P S V F L F P P K P K D T L M I S R T P E V T C V V V D V S H   270
271 E D P E V K F N W Y V D G V E V H N A K T K P R E E Q Y N S T Y R V V S V L T V L H Q D W   315
316 L N G K E Y K C K V S N K A L P A P I E K T I S K A K G Q P R E P Q V Y T L P P S R E E M   360
361 T K N Q V S L T C L V K G F Y P S D I A V E W E S N G Q P E N N Y K T T P P V L D S D G S   405
406 F F L Y S K L T V D K S R W Q Q G N V F S C S V M H E A L H N H Y T Q K S L S L S P G K   449
```

(SEQ ID NO: 16)

FIG. 5B

Pertuzumab
PERJETA

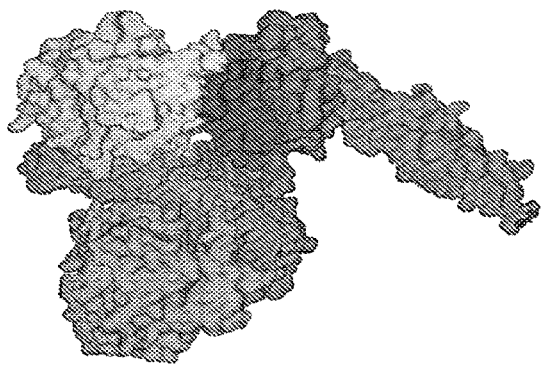

- Binds in Subdomain II at dimerization interface
- Does not prevent receptor shedding
- Moderately affects receptor down-modulation
- Major effect on HER2's role as a coreceptor Trastuzumab
HERCEPTIN

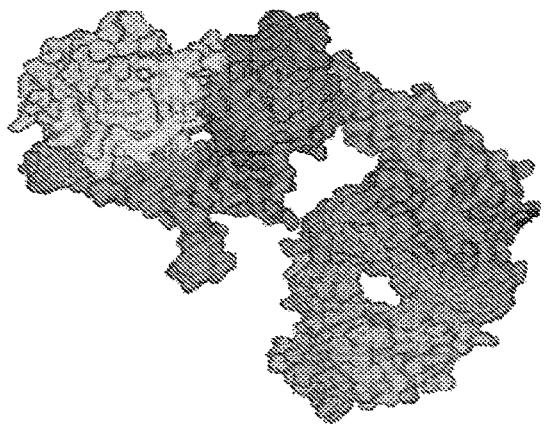

- Binds in Subdomain IV.
- Protects against receptor shedding
- Moderately affects receptor down-modulation
- Slight effect on HER2's role as a coreceptor

Oligosaccharide Structures attached to IgG1

| Structures | Abbreviation | Mass |
|---|---|---|
| Manα(1→6)<br>　　　＼<br>　　　　Manα(1→6)<br>Manα(1→3)／　　　＼<br>　　　　　　　　Manβ(1→4)GlcNAcβ(1→4)GlcNAc- | Man5 | 1235 |
| 　　　　　　　　　　　　　　　Fucα(1→6)<br>　　　　　　　　　　　　　　　　│<br>GlcNAcβ(1→2){Manα(1→6)<br>　　　　　　　　Manα(1→3)<br>　　　　　　　　　＼<br>　　　　　　　　　　Manβ(1→4)GlcNAcβ(1→4)GlcNAc- | G-1 | 1260 |
| GlcNAcβ(1→2)Manα(1→6)<br>GlcNAcβ(1→2)Manα(1→3)<br>　　　　　　　　　＼<br>　　　　　　　　　　Manβ(1→4)GlcNAcβ(1→4)GlcNAc- | G0-F | 1317 |
| Manα(1→6)<br>　　　＼<br>　　　　Manα(1→6)<br>Manα(1→3)／　　　＼<br>Manα(1→2)Manα(1→3)　　Manβ(1→4)GlcNAcβ(1→4)GlcNAc- | Man6 | 1398 |

Oligosaccharide Structures attached to IgG1

| Structures | Abbreviation | Mass |
|---|---|---|
| Galβ(1→4)GlcNAcβ(1→2)⟨Manα(1→6) / Manα(1→3)⟩Manβ(1→4)GlcNAcβ(1→4)GlcNAc- with Fucα(1→6) | G1-1 | 1423 |
| GlcNAcβ(1→2)Manα(1→6) / GlcNAcβ(1→2)Manα(1→3)⟩Manβ(1→4)GlcNAcβ(1→4)GlcNAc- with Fucα(1→6) | G0 | 1463 |
| Galβ(1→4)GlcNAcβ(1→2)Manα(1→6) / GlcNAcβ(1→2)Manα(1→3)⟩Manβ(1→4)GlcNAcβ(1→4)GlcNAc- with Fucα(1→6) | G1 (1-6) | 1626 |
| GlcNAcβ(1→2)Manα(1→6) / Galβ(1→4)GlcNAcβ(1→2)Manα(1→3)⟩Manβ(1→4)GlcNAcβ(1→4)GlcNAc- with Fucα(1→6) | G1 (1-3) | 1626 |
| Galβ(1→4)GlcNAcβ(1→2)Manα(1→6) / Galβ(1→4)GlcNAcβ(1→2)Manα(1→3)⟩Manβ(1→4)GlcNAcβ(1→4)GlcNAc- with Fucα(1→6) | G2 | 1788 |

Masses shown in this figure correspond to the (M+Na)+ values.

*FIG. 24B*

SEQUENCE LISTING

<160> NUMBER OF SEQ ID NOS: 24

<210> SEQ ID NO 1
<211> LENGTH: 195
<212> TYPE: PRT
<213> ORGANISM: Homo sapiens

<400> SEQUENCE: 1

```
Thr Gln Val Cys Thr Gly Thr Asp Met Lys Leu Arg Leu Pro Ala
 1               5                  10                  15

Ser Pro Glu Thr His Leu Asp Met Leu Arg His Leu Tyr Gln Gly
                20                  25                  30

Cys Gln Val Val Gln Gly Asn Leu Glu Leu Thr Tyr Leu Pro Thr
                35                  40                  45

Asn Ala Ser Leu Ser Phe Leu Gln Asp Ile Gln Glu Val Gln Gly
                50                  55                  60

Tyr Val Leu Ile Ala His Asn Gln Val Arg Gln Val Pro Leu Gln
                65                  70                  75

Arg Leu Arg Ile Val Arg Gly Thr Gln Leu Phe Glu Asp Asn Tyr
                80                  85                  90

Ala Leu Ala Val Leu Asp Asn Gly Asp Pro Leu Asn Asn Thr Thr
                95                  100                 105

Pro Val Thr Gly Ala Ser Pro Gly Gly Leu Arg Glu Leu Gln Leu
                110                 115                 120

Arg Ser Leu Thr Glu Ile Leu Lys Gly Gly Val Leu Ile Gln Arg
                125                 130                 135

Asn Pro Gln Leu Cys Tyr Gln Asp Thr Ile Leu Trp Lys Asp Ile
                140                 145                 150

Phe His Lys Asn Asn Gln Leu Ala Leu Thr Leu Ile Asp Thr Asn
                155                 160                 165
```

-continued

```
Arg Ser Arg Ala Cys His Pro Cys Ser Pro Met Cys Lys Gly Ser
            170                 175                 180

Arg Cys Trp Gly Glu Ser Ser Glu Asp Cys Gln Ser Leu Thr Arg
            185                 190                 195

<210> SEQ ID NO 2
<211> LENGTH: 124
<212> TYPE: PRT
<213> ORGANISM: Homo sapiens

<400> SEQUENCE: 2

Thr Val Cys Ala Gly Gly Cys Ala Arg Cys Lys Gly Pro Leu Pro
  1               5                  10                  15

Thr Asp Cys Cys His Glu Gln Cys Ala Gly Cys Thr Gly Pro
                 20                  25                  30

Lys His Ser Asp Cys Leu Ala Cys Leu His Phe Asn His Ser Gly
                 35                  40                  45

Ile Cys Glu Leu His Cys Pro Ala Leu Val Thr Tyr Asn Thr Asp
                 50                  55                  60

Thr Phe Glu Ser Met Pro Asn Pro Glu Gly Arg Tyr Thr Phe Gly
                 65                  70                  75

Ala Ser Cys Val Thr Ala Cys Pro Tyr Asn Tyr Leu Ser Thr Asp
                 80                  85                  90

Val Gly Ser Cys Thr Leu Val Cys Pro Leu His Asn Gln Glu Val
                 95                 100                 105

Thr Ala Glu Asp Gly Thr Gln Arg Cys Glu Lys Cys Ser Lys Pro
                110                 115                 120

Cys Ala Arg Val

<210> SEQ ID NO 3
<211> LENGTH: 169
<212> TYPE: PRT
<213> ORGANISM: Homo sapiens

<400> SEQUENCE: 3

Cys Tyr Gly Leu Gly Met Glu His Leu Arg Glu Val Arg Ala Val
  1               5                  10                  15

Thr Ser Ala Asn Ile Gln Glu Phe Ala Gly Cys Lys Lys Ile Phe
                 20                  25                  30

Gly Ser Leu Ala Phe Leu Pro Glu Ser Phe Asp Gly Asp Pro Ala
                 35                  40                  45

Ser Asn Thr Ala Pro Leu Gln Pro Glu Gln Leu Gln Val Phe Glu
                 50                  55                  60

Thr Leu Glu Glu Ile Thr Gly Tyr Leu Tyr Ile Ser Ala Trp Pro
                 65                  70                  75

Asp Ser Leu Pro Asp Leu Ser Val Phe Gln Asn Leu Gln Val Ile
                 80                  85                  90

Arg Gly Arg Ile Leu His Asn Gly Ala Tyr Ser Leu Thr Leu Gln
                 95                 100                 105

Gly Leu Gly Ile Ser Trp Leu Gly Leu Arg Ser Leu Arg Glu Leu
                110                 115                 120

Gly Ser Gly Leu Ala Leu Ile His His Asn Thr His Leu Cys Phe
                125                 130                 135

Val His Thr Val Pro Trp Asp Gln Leu Phe Arg Asn Pro His Gln
                140                 145                 150

Ala Leu Leu His Thr Ala Asn Arg Pro Glu Asp Glu Cys Val Gly
```

```
                    155                 160                 165

Glu Gly Leu Ala

<210> SEQ ID NO 4
<211> LENGTH: 142
<212> TYPE: PRT
<213> ORGANISM: Homo sapiens

<400> SEQUENCE: 4

Cys His Gln Leu Cys Ala Arg Gly His Cys Trp Gly Pro Gly Pro
  1               5                  10                  15

Thr Gln Cys Val Asn Cys Ser Gln Phe Leu Arg Gly Gln Glu Cys
                 20                  25                  30

Val Glu Glu Cys Arg Val Leu Gln Gly Leu Pro Arg Glu Tyr Val
                 35                  40                  45

Asn Ala Arg His Cys Leu Pro Cys His Pro Glu Cys Gln Pro Gln
                 50                  55                  60

Asn Gly Ser Val Thr Cys Phe Gly Pro Glu Ala Asp Gln Cys Val
                 65                  70                  75

Ala Cys Ala His Tyr Lys Asp Pro Pro Phe Cys Val Ala Arg Cys
                 80                  85                  90

Pro Ser Gly Val Lys Pro Asp Leu Ser Tyr Met Pro Ile Trp Lys
                 95                 100                 105

Phe Pro Asp Glu Glu Gly Ala Cys Gln Pro Cys Pro Ile Asn Cys
                110                 115                 120

Thr His Ser Cys Val Asp Leu Asp Asp Lys Gly Cys Pro Ala Glu
                125                 130                 135

Gln Arg Ala Ser Pro Leu Thr
                140

<210> SEQ ID NO 5
<211> LENGTH: 107
<212> TYPE: PRT
<213> ORGANISM: Mus musculus

<400> SEQUENCE: 5

Asp Thr Val Met Thr Gln Ser His Lys Ile Met Ser Thr Ser Val
  1               5                  10                  15

Gly Asp Arg Val Ser Ile Thr Cys Lys Ala Ser Gln Asp Val Ser
                 20                  25                  30

Ile Gly Val Ala Trp Tyr Gln Gln Arg Pro Gly Gln Ser Pro Lys
                 35                  40                  45

Leu Leu Ile Tyr Ser Ala Ser Tyr Arg Tyr Thr Gly Val Pro Asp
                 50                  55                  60

Arg Phe Thr Gly Ser Gly Ser Gly Thr Asp Phe Thr Phe Thr Ile
                 65                  70                  75

Ser Ser Val Gln Ala Glu Asp Leu Ala Val Tyr Tyr Cys Gln Gln
                 80                  85                  90

Tyr Tyr Ile Tyr Pro Tyr Thr Phe Gly Gly Gly Thr Lys Leu Glu
                 95                 100                 105

Ile Lys

<210> SEQ ID NO 6
<211> LENGTH: 119
<212> TYPE: PRT
<213> ORGANISM: Mus musculus
```

<400> SEQUENCE: 6

Glu Val Gln Leu Gln Gln Ser Gly Pro Glu Leu Val Lys Pro Gly
1               5                   10                  15

Thr Ser Val Lys Ile Ser Cys Lys Ala Ser Gly Phe Thr Phe Thr
            20                  25                  30

Asp Tyr Thr Met Asp Trp Val Lys Gln Ser His Gly Lys Ser Leu
        35                  40                  45

Glu Trp Ile Gly Asp Val Asn Pro Asn Ser Gly Gly Ser Ile Tyr
    50                  55                  60

Asn Gln Arg Phe Lys Gly Lys Ala Ser Leu Thr Val Asp Arg Ser
65                  70                  75

Ser Arg Ile Val Tyr Met Glu Leu Arg Ser Leu Thr Phe Glu Asp
                80                  85                  90

Thr Ala Val Tyr Tyr Cys Ala Arg Asn Leu Gly Pro Ser Phe Tyr
            95                  100                 105

Phe Asp Tyr Trp Gly Gln Gly Thr Thr Leu Thr Val Ser Ser
        110                 115

<210> SEQ ID NO 7
<211> LENGTH: 107
<212> TYPE: PRT
<213> ORGANISM: Artificial Sequence
<220> FEATURE:
<223> OTHER INFORMATION: Sequence is synthesized.

<400> SEQUENCE: 7

Asp Ile Gln Met Thr Gln Ser Pro Ser Ser Leu Ser Ala Ser Val
1               5                   10                  15

Gly Asp Arg Val Thr Ile Thr Cys Lys Ala Ser Gln Asp Val Ser
            20                  25                  30

Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Tyr Ile Tyr Pro Tyr Thr Phe Gly Gln Gly Thr Lys Val Glu
            95                  100                 105

Ile Lys

<210> SEQ ID NO 8
<211> LENGTH: 119
<212> TYPE: PRT
<213> ORGANISM: Artificial Sequence
<220> FEATURE:
<223> OTHER INFORMATION: Sequence is synthesized.

<400> SEQUENCE: 8

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Thr
            20                  25                  30

Asp Tyr Thr Met Asp Trp Val Arg Gln Ala Pro Gly Lys Gly Leu
        35                  40                  45

Glu Trp Val Ala Asp Val Asn Pro Asn Ser Gly Gly Ser Ile Tyr

```
                    50                  55                  60

Asn Gln Arg Phe Lys Gly Arg Phe Thr Leu Ser Val Asp Arg Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                 100                 105

Phe Asp Tyr Trp Gly Gln Gly Thr Leu Val Thr Val Ser Ser
               110                 115

<210> SEQ ID NO 9
<211> LENGTH: 107
<212> TYPE: PRT
<213> ORGANISM: Artificial Sequence
<220> FEATURE:
<223> OTHER INFORMATION: Sequence is synthesized.

<400> SEQUENCE: 9

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
                35                  40                  45

Leu Leu Ile Tyr Ala Ala Ser Ser Leu Glu Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                 100                 105

Ile Lys

<210> SEQ ID NO 10
<211> LENGTH: 119
<212> TYPE: PRT
<213> ORGANISM: Artificial Sequence
<220> FEATURE:
<223> OTHER INFORMATION: Sequence is synthesized.

<400> SEQUENCE: 10

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45

Glu Trp Val Ala Val Ile Ser Gly Asp Gly Ser Thr Tyr Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Arg Val Gly Tyr Ser Leu
                95                 100                 105

Tyr Asp Tyr Trp Gly Gln Gly Thr Leu Val Thr Val Ser Ser
```

<210> SEQ ID NO 11
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 11

Asp Ile Gln Met Thr Gln Ser Pro Ser Ser Leu Ser Ala Ser Val
1               5                   10                  15

Gly Asp Arg Val Thr Ile Thr Cys Lys Ala Ser Gln Asp Val Ser
                20                  25                  30

Ile Gly Val Ala Trp Tyr Gln Gln Lys Pro Gly Lys Ala Pro Lys
                35                  40                  45

Leu Leu Ile Tyr Ser Ala Ser Tyr Arg Tyr Thr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Tyr Ile Tyr Pro Tyr Thr Phe Gly Gln Gly Thr Lys Val Glu
                95                  100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 12
<211> LENGTH: 448
<212> TYPE: PRT
<213> ORGANISM: Artificial sequence
<220> FEATURE:
<223> OTHER INFORMATION: Sequence is synthesized.

<400> SEQUENCE: 12

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Thr
                20                  25                  30

Asp Tyr Thr Met Asp Trp Val Arg Gln Ala Pro Gly Lys Gly Leu
                35                  40                  45

Glu Trp Val Ala Asp Val Asn Pro Asn Ser Gly Gly Ser Ile Tyr
                50                  55                  60

Asn Gln Arg Phe Lys Gly Arg Phe Thr Leu Ser Val Asp Arg Ser

```
                    65                  70                  75
Lys Asn Thr Leu Tyr Leu Gln Met Asn Ser Leu Arg Ala Glu Asp
                80                  85                  90
Thr Ala Val Tyr Tyr Cys Ala Arg Asn Leu Gly Pro Ser Phe Tyr
                95                 100                 105
Phe Asp Tyr Trp Gly Gln Gly Thr Leu Val Thr Val Ser Ser Ala
               110                 115                 120
Ser Thr Lys Gly Pro Ser Val Phe Pro Leu Ala Pro Ser Ser Lys
               125                 130                 135
Ser Thr Ser Gly Gly Thr Ala Ala Leu Gly Cys Leu Val Lys Asp
               140                 145                 150
Tyr Phe Pro Glu Pro Val Thr Val Ser Trp Asn Ser Gly Ala Leu
               155                 160                 165
Thr Ser Gly Val His Thr Phe Pro Ala Val Leu Gln Ser Ser Gly
               170                 175                 180
Leu Tyr Ser Leu Ser Ser Val Val Thr Val Pro Ser Ser Ser Leu
               185                 190                 195
Gly Thr Gln Thr Tyr Ile Cys Asn Val Asn His Lys Pro Ser Asn
               200                 205                 210
Thr Lys Val Asp Lys Lys Val Glu Pro Lys Ser Cys Asp Lys Thr
               215                 220                 225
His Thr Cys Pro Pro Cys Pro Ala Pro Glu Leu Leu Gly Gly Pro
               230                 235                 240
Ser Val Phe Leu Phe Pro Pro Lys Pro Lys Asp Thr Leu Met Ile
               245                 250                 255
Ser Arg Thr Pro Glu Val Thr Cys Val Val Val Asp Val Ser His
               260                 265                 270
Glu Asp Pro Glu Val Lys Phe Asn Trp Tyr Val Asp Gly Val Glu
               275                 280                 285
Val His Asn Ala Lys Thr Lys Pro Arg Glu Glu Gln Tyr Asn Ser
               290                 295                 300
Thr Tyr Arg Val Val Ser Val Leu Thr Val Leu His Gln Asp Trp
               305                 310                 315
Leu Asn Gly Lys Glu Tyr Lys Cys Lys Val Ser Asn Lys Ala Leu
               320                 325                 330
Pro Ala Pro Ile Glu Lys Thr Ile Ser Lys Ala Lys Gly Gln Pro
               335                 340                 345
Arg Glu Pro Gln Val Tyr Thr Leu Pro Pro Ser Arg Glu Glu Met
               350                 355                 360
Thr Lys Asn Gln Val Ser Leu Thr Cys Leu Val Lys Gly Phe Tyr
               365                 370                 375
Pro Ser Asp Ile Ala Val Glu Trp Glu Ser Asn Gly Gln Pro Glu
               380                 385                 390
Asn Asn Tyr Lys Thr Thr Pro Pro Val Leu Asp Ser Asp Gly Ser
               395                 400                 405
Phe Phe Leu Tyr Ser Lys Leu Thr Val Asp Lys Ser Arg Trp Gln
               410                 415                 420
Gln Gly Asn Val Phe Ser Cys Ser Val Met His Glu Ala Leu His
               425                 430                 435
Asn His Tyr Thr Gln Lys Ser Leu Ser Leu Ser Pro Gly
               440                 445

<210> SEQ ID NO 13
```

```
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 13

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
             20                  25                  30

Thr Ala Val Ala Trp Tyr Gln Gln Lys Pro Gly Lys Ala Pro Lys
         35                  40                  45

Leu Leu Ile Tyr Ser Ala Ser Phe Leu Tyr Ser Gly Val Pro Ser
     50                  55                  60

Arg Phe Ser Gly Ser Arg Ser Gly Thr Asp Phe Thr Leu Thr Ile
 65                  70                  75

Ser Ser Leu Gln Pro Glu Asp Phe Ala Thr Tyr Tyr Cys Gln Gln
                 80                  85                  90

His Tyr Thr Thr Pro Pro Thr Phe Gly Gln Gly Thr Lys Val Glu
             95                 100                 105

Ile Lys Arg Thr Val Ala Ala Pro Ser Val Phe Ile Phe Pro Pro
        110                 115                 120

Ser Asp Glu Gln Leu Lys Ser Gly Thr Ala Ser Val Val Cys Leu
    125                 130                 135

Leu Asn Asn Phe Tyr Pro Arg Glu Ala Lys Val Gln Trp Lys Val
140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
        185                 190                 195

Val Thr His Gln Gly Leu Ser Ser Pro Val Thr Lys Ser Phe Asn
    200                 205                 210

Arg Gly Glu Cys

<210> SEQ ID NO 14
<211> LENGTH: 449
<212> TYPE: PRT
<213> ORGANISM: Artificial sequence
<220> FEATURE:
<223> OTHER INFORMATION: Sequence is synthesized.

<400> SEQUENCE: 14

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
             20                  25                  30

Asp Thr Tyr Ile His Trp Val Arg Gln Ala Pro Gly Lys Gly Leu
         35                  40                  45

Glu Trp Val Ala Arg Ile Tyr Pro Thr Asn Gly Tyr Thr Arg Tyr
     50                  55                  60

Ala Asp Ser Val Lys Gly Arg Phe Thr Ile Ser Ala Asp Thr Ser
 65                  70                  75

Lys Asn Thr Ala Tyr Leu Gln Met Asn Ser Leu Arg Ala Glu Asp
                 80                  85                  90
```

```
Thr Ala Val Tyr Tyr Cys Ser Arg Trp Gly Asp Gly Phe Tyr
             95                 100                 105

Ala Met Asp Tyr Trp Gly Gln Gly Thr Leu Val Thr Val Ser Ser
            110                 115                 120

Ala Ser Thr Lys Gly Pro Ser Val Phe Pro Leu Ala Pro Ser Ser
            125                 130                 135

Lys Ser Thr Ser Gly Gly Thr Ala Ala Leu Gly Cys Leu Val Lys
            140                 145                 150

Asp Tyr Phe Pro Glu Pro Val Thr Val Ser Trp Asn Ser Gly Ala
            155                 160                 165

Leu Thr Ser Gly Val His Thr Phe Pro Ala Val Leu Gln Ser Ser
            170                 175                 180

Gly Leu Tyr Ser Leu Ser Ser Val Val Thr Val Pro Ser Ser Ser
            185                 190                 195

Leu Gly Thr Gln Thr Tyr Ile Cys Asn Val Asn His Lys Pro Ser
            200                 205                 210

Asn Thr Lys Val Asp Lys Lys Val Glu Pro Lys Ser Cys Asp Lys
            215                 220                 225

Thr His Thr Cys Pro Pro Cys Pro Ala Pro Glu Leu Leu Gly Gly
            230                 235                 240

Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp
            305                 310                 315

Trp Leu Asn Gly Lys Glu Tyr Lys Cys Lys Val Ser Asn Lys Ala
            320                 325                 330

Leu Pro Ala Pro Ile Glu Lys Thr Ile Ser Lys Ala Lys Gly Gln
            335                 340                 345

Pro Arg Glu Pro Gln Val Tyr Thr Leu Pro Pro Ser Arg Glu Glu
            350                 355                 360

Met Thr Lys Asn Gln Val Ser Leu Thr Cys Leu Val Lys Gly Phe
            365                 370                 375

Tyr Pro Ser Asp Ile Ala Val Glu Trp Glu Ser Asn Gly Gln Pro
            380                 385                 390

Glu Asn Asn Tyr Lys Thr Thr Pro Pro Val Leu Asp Ser Asp Gly
            395                 400                 405

Ser Phe Phe Leu Tyr Ser Lys Leu Thr Val Asp Lys Ser Arg Trp
            410                 415                 420

Gln Gln Gly Asn Val Phe Ser Cys Ser Val Met His Glu Ala Leu
            425                 430                 435

His Asn His Tyr Thr Gln Lys Ser Leu Ser Leu Ser Pro Gly
            440                 445

<210> SEQ ID NO 15
<211> LENGTH: 217
<212> TYPE: PRT
<213> ORGANISM: Artificial sequence
<220> FEATURE:
```

<223> OTHER INFORMATION: Sequence is synthesized.

<400> SEQUENCE: 15

```
Val His Ser Asp Ile Gln Met Thr Gln Ser Pro Ser Ser Leu Ser
 1               5                  10                  15

Ala Ser Val Gly Asp Arg Val Thr Ile Thr Cys Lys Ala Ser Gln
                20                  25                  30

Asp Val Ser Ile Gly Val Ala Trp Tyr Gln Gln Lys Pro Gly Lys
                35                  40                  45

Ala Pro Lys Leu Leu Ile Tyr Ser Ala Ser Tyr Arg Tyr Thr Gly
                50                  55                  60

Val Pro Ser Arg Phe Ser Gly Ser Gly Ser Gly Thr Asp Phe Thr
                65                  70                  75

Leu Thr Ile Ser Ser Leu Gln Pro Glu Asp Phe Ala Thr Tyr Tyr
                80                  85                  90

Cys Gln Gln Tyr Tyr Ile Tyr Pro Tyr Thr Phe Gly Gln Gly Thr
                95                  100                 105

Lys Val Glu Ile Lys Arg Thr Val Ala Ala Pro Ser Val Phe Ile
                110                 115                 120

Phe Pro Pro Ser Asp Glu Gln Leu Lys Ser Gly Thr Ala Ser Val
                125                 130                 135

Val Cys Leu Leu Asn Asn Phe Tyr Pro Arg Glu Ala Lys Val Gln
                140                 145                 150

Trp Lys Val Asp Asn Ala Leu Gln Ser Gly Asn Ser Gln Glu Ser
                155                 160                 165

Val Thr Glu Gln Asp Ser Lys Asp Ser Thr Tyr Ser Leu Ser Ser
                170                 175                 180

Thr Leu Thr Leu Ser Lys Ala Asp Tyr Glu Lys His Lys Val Tyr
                185                 190                 195

Ala Cys Glu Val Thr His Gln Gly Leu Ser Ser Pro Val Thr Lys
                200                 205                 210

Ser Phe Asn Arg Gly Glu Cys
                215
```

<210> SEQ ID NO 16
<211> LENGTH: 449
<212> TYPE: PRT
<213> ORGANISM: Artificial sequence
<220> FEATURE:
<223> OTHER INFORMATION: Sequence is synthesized.

<400> SEQUENCE: 16

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
                20                  25                  30

Asp Tyr Thr Met Asp Trp Val Arg Gln Ala Pro Gly Lys Gly Leu
                35                  40                  45

Glu Trp Val Ala Asp Val Asn Pro Asn Ser Gly Gly Ser Ile Tyr
                50                  55                  60

Asn Gln Arg Phe Lys Gly Arg Phe Thr Leu Ser Val Asp Arg Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                  100                 105
```

Phe Asp Tyr Trp Gly Gln Gly Thr Leu Val Thr Val Ser Ser Ala
                    110                 115                 120

Ser Thr Lys Gly Pro Ser Val Phe Pro Leu Ala Pro Ser Ser Lys
            125                 130                 135

Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210

Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu
            320                 325                 330

Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Glu Glu Met
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390

Asn Asn Tyr Lys Thr Thr Pro Pro Val Leu Asp Ser Asp Gly Ser
            395                 400                 405

Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly Lys
            440                 445

<210> SEQ ID NO 17
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa

```
<222> LOCATION: 10
<223> OTHER INFORMATION: Xaa is preferrably D or S

<400> SEQUENCE: 17

Gly Phe Thr Phe Thr Asp Tyr Thr Met Xaa
                5                   10

<210> SEQ ID NO 18
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 18

Asp Val Asn Pro Asn Ser Gly Gly Ser Ile Tyr Asn Gln Arg Phe
 1               5                  10                  15

Lys Gly

<210> SEQ ID NO 19
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 19

Asn Leu Gly Pro Ser Phe Tyr Phe Asp Tyr
                 5                  10

<210> SEQ ID NO 20
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 20

Lys Ala Ser Gln Asp Val Ser Ile Gly Val Ala
                 5                  10

<210> SEQ ID NO 21
<211> LENGTH: 7
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 5
<223> OTHER INFORMATION: Xaa is preferably R or L
<220> FEATURE:
<221> NAME/KEY: Xaa
<222> LOCATION: 6
<223> OTHER INFORMATION: Xaa is preferably Y or E
<220> FEATURE:
<221> NAME/KEY: Xaa
<222> LOCATION: 7
<223> OTHER INFORMATION: Xaa is preferably T or S

<400> SEQUENCE: 21

Ser Ala Ser Tyr Xaa Xaa Xaa
                 5

<210> SEQ ID NO 22
<211> LENGTH: 9
<212> TYPE: PRT
<213> ORGANISM: Artificial sequence
```

```
<220> FEATURE:
<223> OTHER INFORMATION: Sequence is synthesized.

<400> SEQUENCE: 22

Gln Gln Tyr Tyr Ile Tyr Pro Tyr Thr
                5

<210> SEQ ID NO 23
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 23

Gly Phe Thr Phe Thr Asp Tyr Thr Met Asp
                5                   10

<210> SEQ ID NO 24
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 24

Ser Ala Ser Tyr Arg Tyr Thr
                5
```

PERTUZUMAB VARIANTS AND EVALUATION THEREOF

CROSS REFERENCE TO RELATED APPLICATIONS

This application is a divisional of U.S. application Ser. No. 16/510,287, filed on Jul. 12, 2019 which is a continuation of U.S. application Ser. No. 15/788,598, filed on Oct. 19, 2017, now abandoned, which is a divisional of U.S. application Ser. No. 14/253,038, filed Apr. 15, 2014, now U.S. Pat. No. 9,815,904 which claims the benefit under 35 USC § 119(e) of U.S. Provisional Application Ser. No. 61/812,603, filed Apr. 16, 2013, which applications are hereby incorporated by reference in entirety.

SEQUENCE LISTING

The instant application contains a Sequence Listing submitted via EFS-Web and hereby incorporated by reference in its entirety. Said ASCII copy, created Jun. 20, 2022, is named P05584_US_7_Sequence_Listing.txt, and is 31,367 bytes in size.

FIELD OF THE INVENTION

The present invention concerns variants of Pertuzumab. In particular, it concerns: an unpaired cysteine variant comprising Cys23/Cys88 unpaired cysteines in one or both variable light domains of Pertuzumab, an afucosylated variant of Pertuzumab, a low-molecular-weight-species (LMWS) of Pertuzumab, and a high-molecular-weight-species (HMWS) or Pertuzumab. The invention further concerns the isolated variants, compositions, pharmaceutical compositions, and articles of manufacture comprising the variants, as well as methods of making and characterizing the variants and compositions thereof.

BACKGROUND OF THE INVENTION

Pertuzumab (PERJETA®) (also called rhuMAb 2C4) is a monoclonal antibody (MAb) which is the first of its class in a line of agents called "HER dimerization inhibitors." By binding to HER2, it inhibits dimerization of HER2 with other HER receptors and thus inhibits tumor growth. Pertuzumab received United Stated Food and Drug Administration (US FDA) approval for the treatment of HER2-positive metastatic breast cancer on Jun. 8, 2012.

U.S. Pat. No. 7,862,817 (Adams et al.) describe a humanized variant of the 2C4 antibody called humanized 2C4 version 574 or recombinant humanized monoclonal antibody 2C4 (rhuMAb 2C4). The antibody bound Subdomain II in the Human Epidermal Growth Factor Receptor 2 (HER2) extracellular domain (ECD). The rhuMAb 2C4 antibody was produced on a laboratory scale and shown to bind to HER2 and inhibit growth of MDA-175 cells (which express HER2 at a 1+level) and MCF7 xenografts implanted into mice. See, also, Adams et al. *Cancer Immunol. Immunother.* 55(6):717-727 (2006)

U.S. Pat. No. 6,339,142 (Blank and Basey) describes a HER2 antibody composition comprising a mixture of anti-HER2 antibody and one or more acidic variants thereof, wherein the amount of the acidic variant(s) is less than about 25%. Humanized monoclonal antibody 4D5 variant 8 (humMAb4D5-8 or Trastuzumab) is the exemplified HER2 antibody.

U.S. Pat. Nos. 7,560,111, 7,879,325, and U.S. Pat. No. 8,241,630 (Kao et al.) describe a variant of Pertuzumab (rhuMAb 2C4) comprising an amino terminal leader extension (VHS-) on one or both light chains of the antibody, the so-called "VHS-variant." When, Reference Material (Phase I), Lot S9802A (Phase II), and 400 L scale Process Development Material were tested for free thiol using the Ellman's analysis at native conditions, free thiol level was below the limit of detection in all materials tested. From 1-2% of the Pertuzumab in the compositions tested were afucosylated (G0-F) as determined by capillary electrophoresis (CE). See Table 5 of U.S. Pat. No. 7,560,111 (Kao et al.).

WO 2009/099829 (Harris et al.) describe acidic variants of pertuzumab including: deamidated variant, glycated variant, disulfide reduced variant, non-reducible variant, and sialylated variant. The variants were characterized as disclosed as follows:

TABLE 1

Acidic Variants in WO 2009/099829 (Harris et al.)
Methods for Characterization of Acidic Variants

| Method | Variants Detected | Variant Name |
|---|---|---|
| CEX +/− Sialydase Treatment | 6% Sialylated | Sialylated Variant |
| Reduced CE-SDS | 1.5% Incompletely Reduced | Non-Reducible Variant |
| Non-Reduced CE-SDS | 6% Reduced Disulfide | Disulfide Reduced Variant |
| Boronate Chromatography | 3.5% Glycated (Higher Order) | Glycated Variant |
| Peptide Map | Deamidated | Deamidated Variant |

CEX = cation exchange.
CE-SDS = Capillary Electrophoresis with Sodium Dodecyl Sulfate.

The experimental method used to characterize the disulfide reduced variant in WO 2009/099829 (Harris et al.), non-reduced CE-SDS of intact antibody, evaluated reduced inter-chain disulfide bonds, rather than intra-chain disulfide bonds.

Zhang et al. *Anal. Chem.* 84(16):7112-7123 (2012) report a recombinant antibody (mAb A) having unpaired cysteines (Cys22 and Cys96) in the variable heavy (VH domain) thereof. The unpaired cysteines were found to have no significant impact on binding of the antibody to CD20, and mAb A with unpaired cysteines was fully active in a potency assay (complement-dependent cytotoxicity, CDC, assay).

WO 2009/009523 (Kao et al.) discloses prevention of inter-chain disulfide bond reduction during recombinant production of the ocreclizumab (rhuMAb 2H7) antibody which binds CD20.

Harris, R. *Dev. Biol.* (Basel, Switzerland) 122: 117-127 (2005) disclosed unpaired cysteines (Cys22 and Cys96) in the variable heavy (VH) domain of omalizumab, a humanized anti-IgE antibody. The unpaired cysteine form had significantly lower potency.

SUMMARY OF THE INVENTION

The experimental data herein concerns variant forms of Pertuzumab, including an unpaired cysteine variant, afucosylated variant, low-molecular-weight-species (LMWS), and high-molecular-weight-species (HMWS). Means for identifying, characterizing, and quantifying these variants are valuable in the manufacture and quality control methods for the Pertuzumab drug composition.

Thus, in a first aspect, the invention concerns a composition comprising Pertuzumab and unpaired cysteine variant thereof, wherein the unpaired cysteine variant comprises Cys23/Cys88 unpaired cysteines in one or both variable light domains of Pertuzumab. The unpaired cysteine variant includes a heterodimer variant (comprising Cys23/Cys88 unpaired cysteines in only one variable light domain of Pertuzumab) and/or a homodimer variant (comprising Cys23/Cys88 unpaired cysteines in both variable light domains of Pertuzumab).

The composition optionally further comprises one or more additional variants of Pertuzumab such as afucosylated variant, low-molecular-weight-species (LMWS) variant, high-molecular-weight-species (HMWS) variant, glycated variant, disulfide reduced variant, non-reducible variant, deamidated variant, sialylated variant, VHS-variant, C-terminal lysine variant, methionine-oxidized variant, G1 glycosylation variant, G2 glycosylation variant, and non-glycosylated heavy chain variant.

The invention also concerns a composition comprising Pertuzumab and an afucosylated variant of Pertuzumab, wherein the amount of the afucosylated variant is from 0.9 to 4.1% of the composition. In one embodiment, the invention concerns a composition comprising Pertuzumab and an afucosylated variant of Pertuzumab, wherein the amount of the afucosylated variant is greater than 2% of the composition. According to this embodiment, the amount of the afucosylated variant is greater than that reported in U.S. Pat. Nos. 7,560,111, 7,879,325, and 8,241,630 (Kao et al.).

In an additional aspect, the invention concerns a composition comprising a mixture of Pertuzumab, low-molecular-weight species (LMWS) of Pertuzumab, and high-molecular-weight-species (HMWS) of Pertuzumab, wherein the amount of LMWS is ≤1.6% and the amount of HMWS is ≤1.7%.

The invention also concerns a composition comprising a mixture of Pertuzumab, Peak 1, and Peak 2, wherein the amount of Peak 1 is ≤0.5% and the amount of Peak 2 is ≤1.0% as measured by reduced capilliary electrophoresis sodium dodecyl sulphate (R-CE-SDS) assay.

Additional aspects of the invention concern pharmaceutical compositions, articles of manufacture, and methods of treating a cancer patient using or comprising the compositions herein.

In an additional aspect, the invention concerns a method for evaluating a Pertuzumab composition comprising: (1) measuring the amount of unpaired cysteine variant in the composition, wherein the unpaired cysteine variant comprises Cys23/Cys88 unpaired cysteines in one or both variable light domains of Pertuzumab; and/or (2) measuring the amount of afucosylated Pertuzumab in the composition; and/or (3) measuring the amount of low-molecular-weight-species (LMWS) or high-molecular-weight-species (HMWS) of Pertuzumab in the composition.

In yet an additional aspect, the invention concerns a method for evaluating the biological activity of a Pertuzumab composition comprising measuring the amount of afucosylated Pertuzumab variant in the composition to determine the antibody-dependent cell-mediated cytotoxicity (ADCC) activity of the composition, and confirming the amount of afucosylated Pertuzumab is in the range from about 0.9 to about 4.1%.

In another aspect, the invention concerns a method for making a composition comprising: (1) producing a composition comprising Pertuzumab and one or more variants thereof, and (2) subjecting the composition so-produced to an analytical assay to evaluate the amount of the variant(s) therein, wherein the variant(s) comprise: (i) unpaired cysteine variant comprising Cys23/Cys88 unpaired cysteines in one or both variable light domains of Pertuzumab; and/or (ii) afucosylated variant of Pertuzumab; and/or (iii) high-molecular-weight-species (HMWS) of Pertuzumab; and/or (iv) low-molecular-weight-species (LMWS) of Pertuzumab, and/or (v) Peak 1 fragment(s) of Pertuzumab, and/or (vi) Peak 2 fragment(s) of Pertuzumab.

In another aspect, the invention concerns an isolated variant of Pertuzumab, wherein the isolated variant comprises: (a) an unpaired cysteine variant of Pertuzumab, wherein the variant is a heterodimer variant comprising Cys23/Cys88 unpaired cysteines in only one variable light domain of Pertuzumab; and/or (b) an unpaired cysteine variant of Pertuzumab, wherein the variant is a homodimer variant comprising Cys23/Cys88 unpaired cysteines in both variable light domains of Pertuzumab; and/or (c) afucosylated variant of Pertuzumab; and/or (d) high-molecular-weight-species (HMWS) of Pertuzumab; and/or (e) low-molecular-weight-species (LMWS) of Pertuzumab; and/or (f) Peak 1 fragment(s) of Pertuzumab, and/or (g) Peak 2 fragment(s) of Pertuzumab.

In an additional aspect, the invention concerns a method for evaluating fragmentation of a Pertuzumab composition comprising measuring the amount of Peak 1 and Peak 2 in the composition by reduced capilliary electrophoresis sodium dodecyl sulphate (R-CE-SDS) assay and confirming the amount of Peak 1 is ≤5% and the amount of Peak 2 is ≤1.0%.

BRIEF DESCRIPTION OF THE DRAWINGS

FIGS. 2A and 2B depict alignments of the amino acid sequences of the variable light (VL) (FIG. 2A) and variable heavy (VH) (FIG. 2B) domains of murine monoclonal antibody 2C4 (SEQ ID Nos. 5 and 6, respectively); VL and VH domains of variant 574/Pertuzumab (SEQ ID Nos. 7 and 8, respectively), and human VL and VH consensus frameworks (hum $\kappa$I, light kappa subgroup I; humIII, heavy subgroup III) (SEQ ID Nos. 9 and 10, respectively). Asterisks identify differences between variable domains of Pertuzumab and murine monoclonal antibody 2C4 or between variable domains of Pertuzumab and the human framework. Complementarity Determining Regions (CDRs) are in brackets.

FIGS. 3A and 3B show the amino acid sequences of Pertuzumab light chain (FIG. 3A; SEQ ID NO. 11) and heavy chain (FIG. 3B; SEQ ID No. 12). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIGS. 4A and 4B show the amino acid sequences of Trastuzumab light chain (FIG. 4A; SEQ ID NO. 13) and heavy chain (FIG. 4B; SEQ ID NO. 14), respectively. Boundaries of the variable light and variable heavy domains are indicated by arrows.

FIGS. 5A and 5B depict a variant Pertuzumab light chain sequence (FIG. 5A; SEQ ID NO. 15) and a variant Pertuzumab heavy chain sequence (FIG. 5B; SEQ ID NO. 16), respectively.

FIG. 23 compares activities of Trastuzumab (which binds to Subdomain IV near the juxtamembrane domain of HER2 ECD) and Pertuzumab (which binds to Subdomain II of HER2 ECD).

FIGS. 24A and 24B depict oligosaccharide structures attached to an IgG antibody.

DETAILED DESCRIPTION OF THE PREFERRED EMBODIMENTS

I. Definitions

Figure 6:
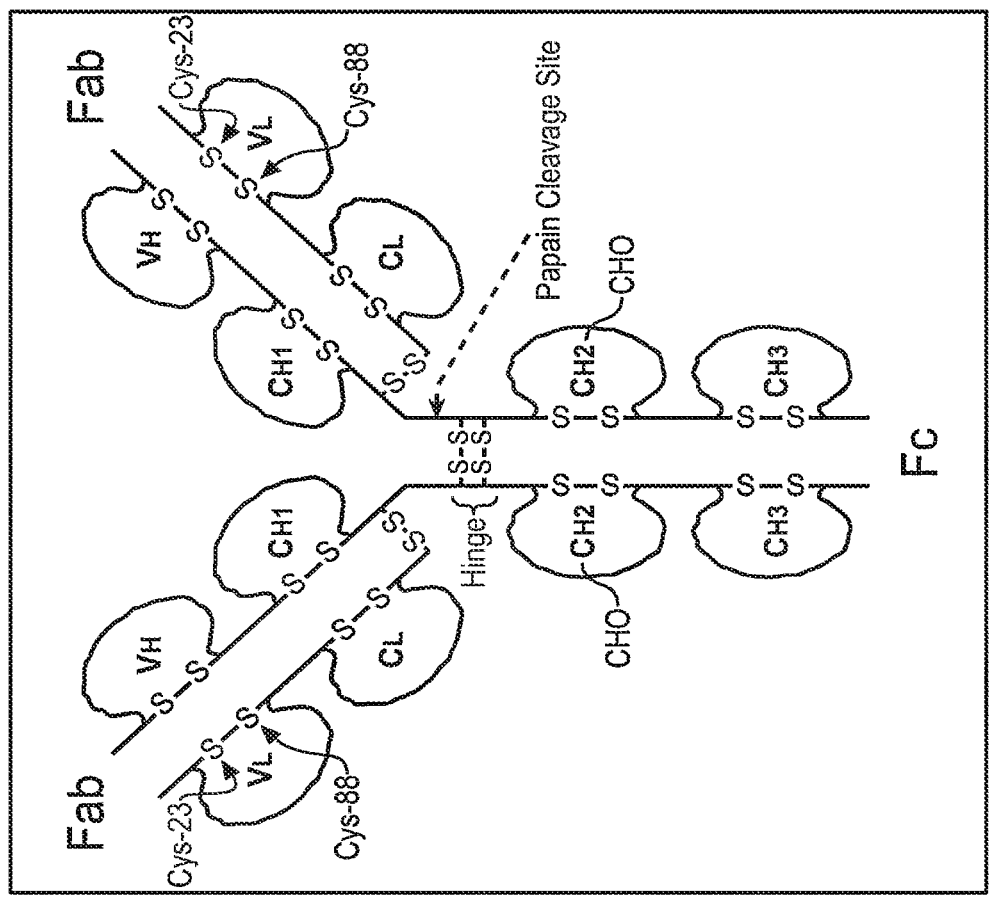
FIG. 6 depicts the structure of (main species) Pertuzumab including its 4 inter-chain and 12 intra-chain disulfide bonds, including the Cys23/Cys88 intra-chain disulfide bonds in each of the variable light (VL) domains. Domains depicted are: VL=variable light domain; VH=variable heavy domain; CL=light chain constant domain; CH1=heavy chain constant domain 1; CH2=heavy chain constant domain 2; CH3=heavy chain constant domain 3.

"Paired cysteines" herein refers to two cysteine residues that form a disulfide bond in a protein, such as an antibody. Such disulfide bond can be an inter-chain disulfide bond (e.g. disulfide bond between heavy and light chains of an antibody, or between two heavy chains of an antibody), or intra-chain disulfide bond (e.g. within a light chain of an antibody or within a heavy chain of an antibody). Most IgG1 antibodies comprise four inter-chain disulfide bonds and twelve intra-chain disulfide bonds. See FIG. 6.

An "unpaired cysteine variant" is a variant of a protein (e.g. an antibody such as Pertuzumab) in which one or more paired cysteines are not in the disulfide bonded state. Such unpaired cysteines may not have been paired to form a disulfide bond (e.g. when the protein originally folded into its tertiary structure) or may have formed a disulfide bond but which has later broken (e.g. during manufacture or upon storage). The unpaired cysteines are often referred to as free thiols or free sulfhydryls. In one embodiment, the unpaired cysteines are from an intra-chain disulfide bond. In one embodiment, the unpaired cysteines are in a light chain, e.g. a variable light domain of the antibody. In one embodiment, the unpaired cysteine variant is a Cys23/Cys88 variant.

Figure 20A:
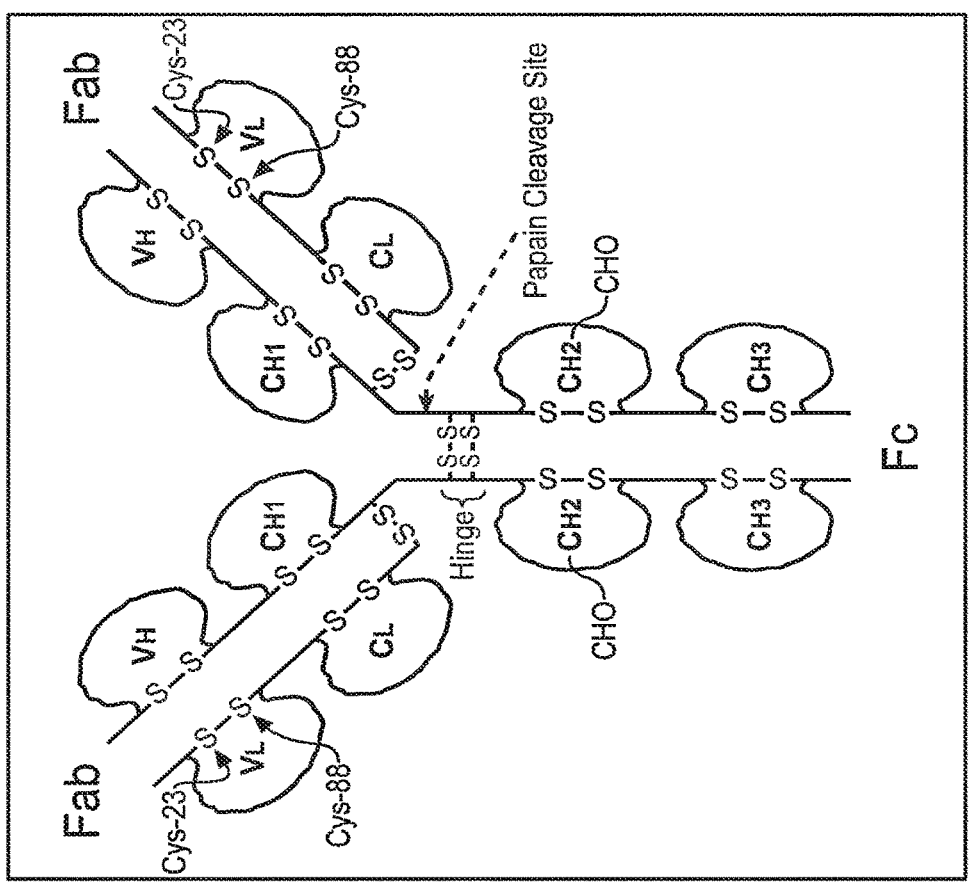
FIGS. 20A, 20B, and 20C depict schematically: main species or wild type IgG1 (FIG. 20A), Cys23/Cys88 heterodimer variant (FIG. 20B), and Cys23/Cys88 homodimer variant (FIG. 20C).
Figure 20C:
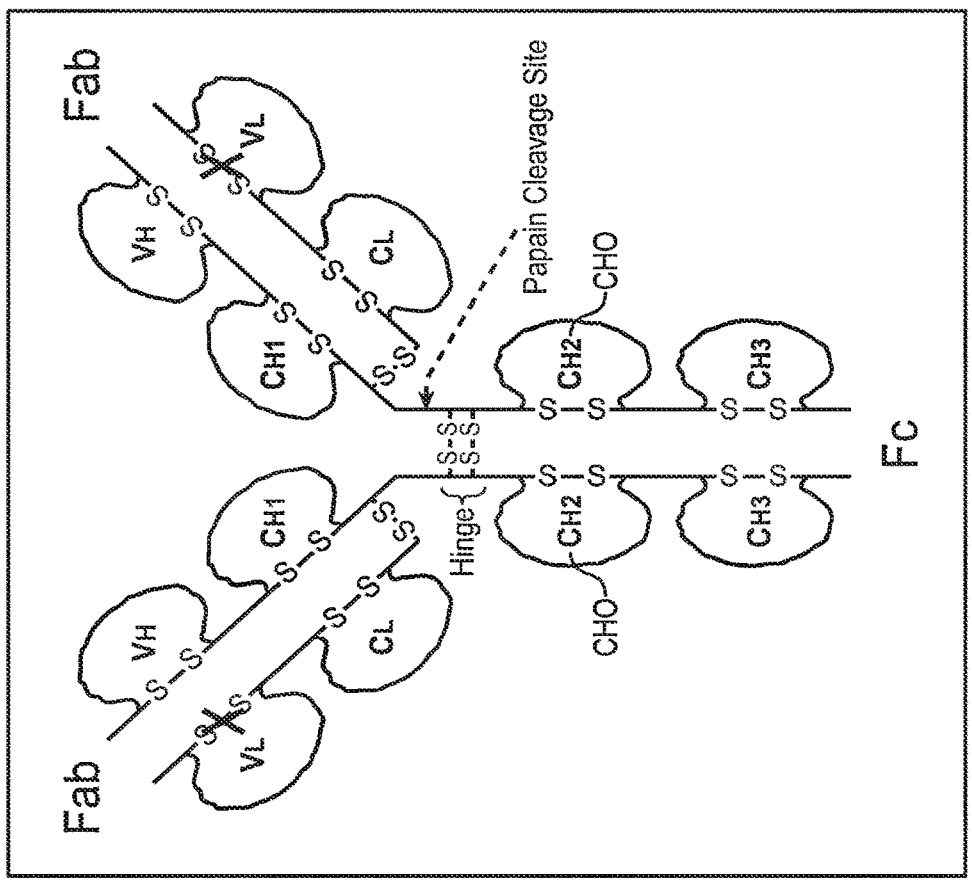
Figure 20B:
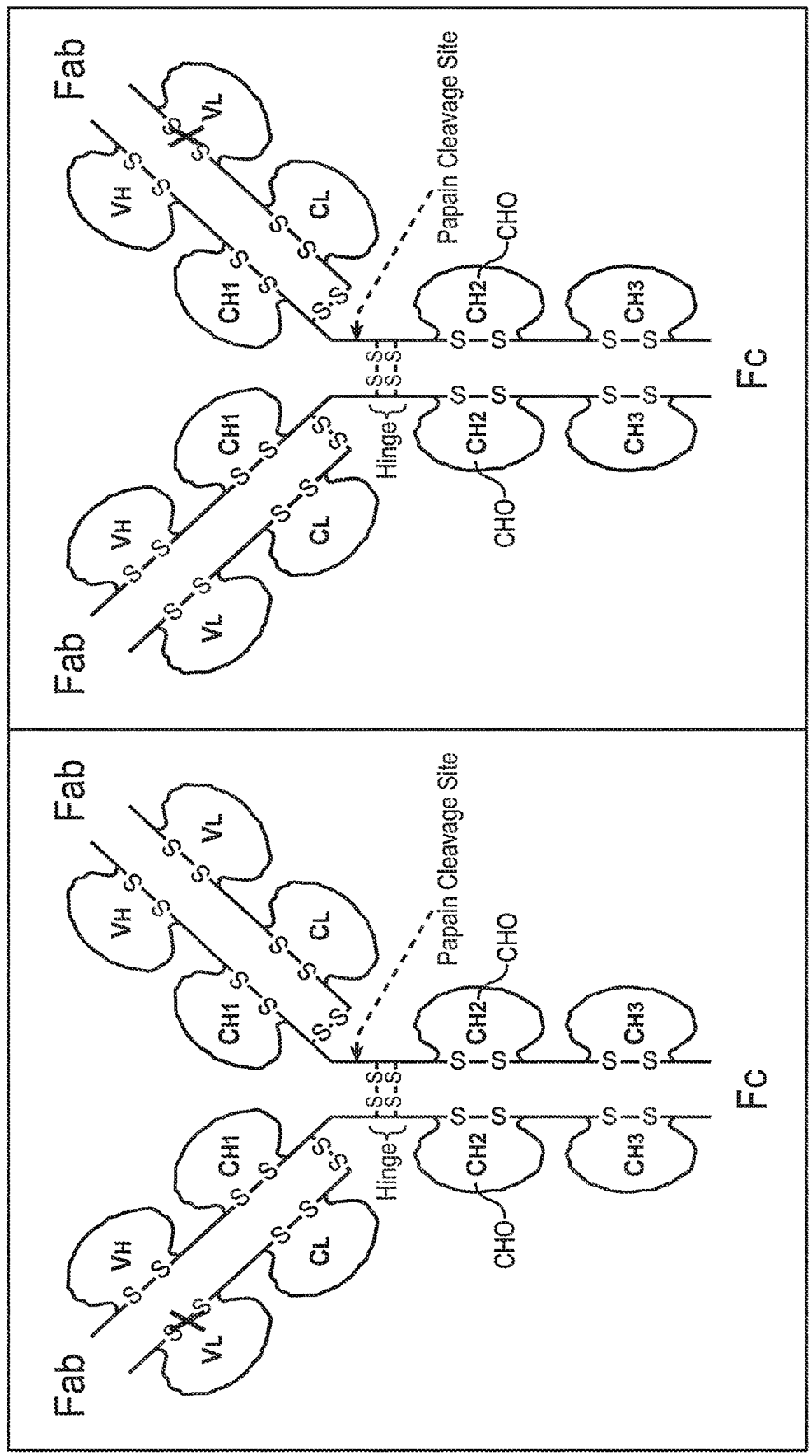

A "Cys23/Cys88" unpaired cysteine variant lacks an intra-molecular disulfide bond at cysteine residues 23 and 88 in one or both variable light domains of the antibody. See FIGS. 20(b) and (c) herein.

A "homodimer variant" lacks Cys23/Cys88 disulfide bonds in both variable light domains of the antibody. See FIG. 20(c) herein.

A "heterodimer variant" lacks only one Cys23/Cys88 disulfide bond in one variable light domain of an antibody. See FIG. 20(b) herein.

An "afucosylated variant" is a glycosylation variant of an antibody in which one or both of the oligosaccharide structures attached to residue Asn299 of one or both heavy chains lacks fucose, e.g. lacks Fucα(1->6), in the core oligosaccharide structure.

A "low-molecular-weight-species" or "LMWS" of Pertuzumab comprises a fragment of Pertuzumab that has a molecular weight less than that of main species or intact Pertuzumab (e.g. where the intact Pertuzumab has a molecular weight of about 145,197 Da measuring its peptide chains only). The LMWS can be detected by size exclusion high performance liquid chromatography (SE-HPLC) and/or non-reduced Capillary Electrophoresis with Sodium Dodecyl Sulfate (CE-SDS) for example as in Example 5. In one embodiment, the LMWS comprises or consists of "Peak 6" as obtained by CE-SDS (see, e.g., Example 5).

A "high-molecular-weight-species" or "HMWS" comprises a preparation of Pertuzumab having a molecular weight that is greater than the main species or intact Pertuzumab (e.g. where the intact Pertuzumab has a molecular weight of about 145,197 Da measuring its peptide chains only). The HMWS can be detected by size exclusion high performance liquid chromatography (SE-HPLC) and/or non-reduced Capillary Electrophoresis with Sodium Dodecyl Sulfate (CE-SDS) assay for example as in Example 5.

Figure 33A:
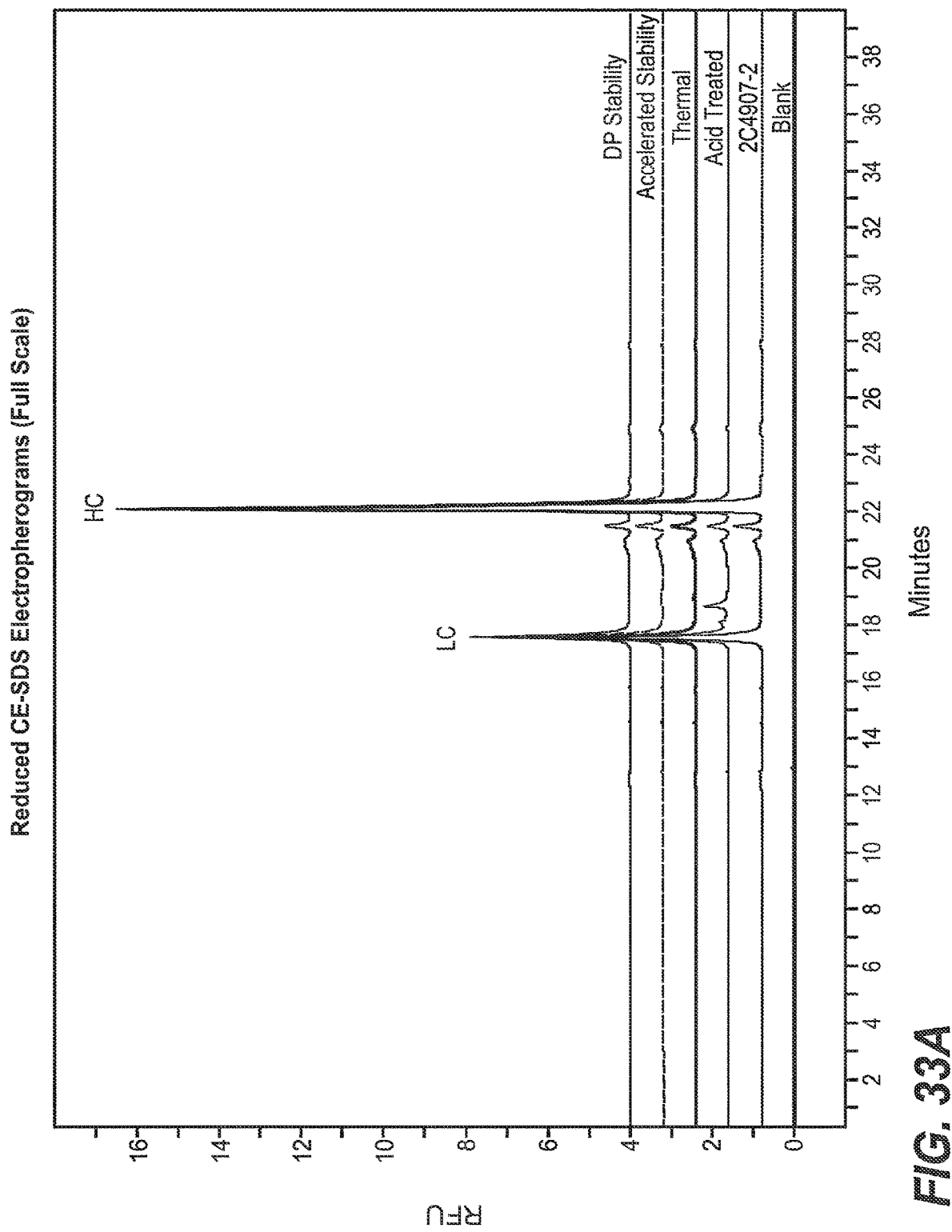
FIGS. 33A and 33B depict reduced CE-SDS (R-CE-SDS) electropherograms for Example 6: full scale (FIG. 33A), and expanded scale (FIG. 33B).
Figure 33B:
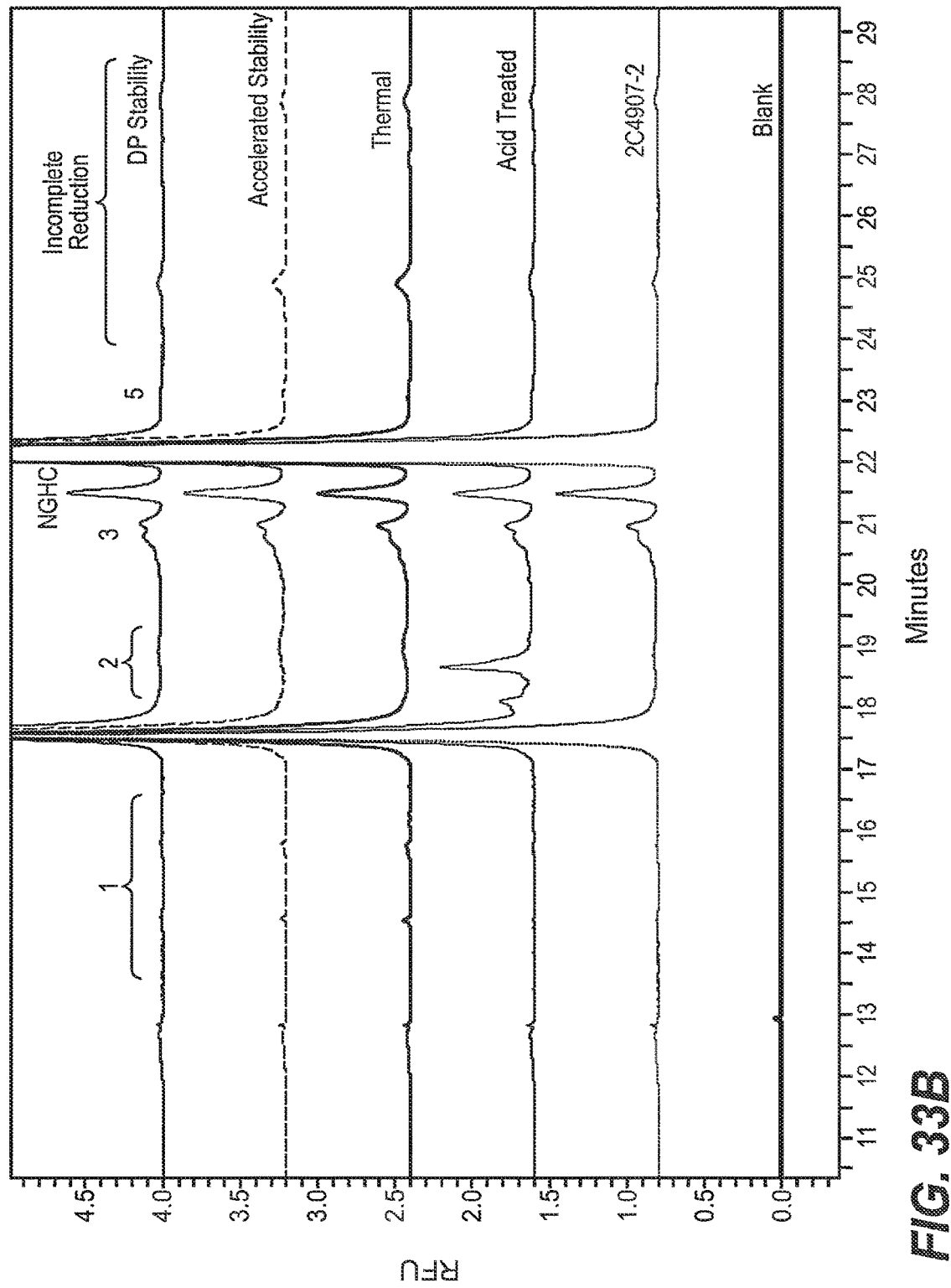

"Peak 1" herein refers to Pertuzumab fragment(s) which are of a size smaller than Pertuzumab light chain (LC). Peak 1 fragment(s) can be separated from main species Pertuzumab by CE-SDS assay, preferably by reduced CE-SDS (R-CE-SDS) assay. See, for example, FIG. 33B, Table 16, and Table 18 herein. Preferably, the amount of peak 1 in a Pertuzumab composition is ≤0.5%. Optionally, the R-CE-SDS assay is carried out as described in Example 6 and the corrected peak area (CPA) provides the % peak 1 in a composition.

"Peak 2" herein refers to Pertuzumab fragment(s) which are of a size larger than Pertuzumab light chain (LC) and smaller than Pertuzumab non-glycosylated heavy chain (NGHC). Peak 2 can be separated from main species Pertuzumab by CE-SDS, preferably by reduced (R-CE-SDS) assay. Peak 2 excludes peak 3 that can appear during R-CE-SDS assay as explained in Example 6 herein. See, for example, FIG. 33B, Table 16, and Table 18 herein. Preferably, the amount of peak 2 in a Pertuzumab composition is ≤1.0%. Optionally, the R-CE-SDS assay is carried out as described in Example 6 and the corrected peak area (CPA) provides the % peak 2 in a composition.

"Fragmentation" refers to polypeptide chain cleavage, e.g. cleavage of Pertuzumab light chain and/or heavy chain. It does not include the dissociation of non-covalently associated polypeptide chains during NR-CE-SDS analysis, for example.

An "analytical assay" is an assay which qualitatively assesses and/or quantitatively measures the presence or amount of an analyte (e.g. an antibody variant) in a composition. The composition subjected to the assay can be a purified composition, including a pharmaceutical composition.

A "Fab hydrophobic interaction chromatograpy assay" or "Fab HIC assay" comprises generating fragments (e.g. Fab fragments) of the antibodies in a composition (e.g. using papain enzyme) and subjecting the antibody fragments thus generated to HIC in order to separate unpaired cysteine variants from main species Pertuzumab. An exemplarly such assay is disclosed in Example 1 herein.

A "HER receptor" is a receptor protein tyrosine kinase which belongs to the HER receptor family and includes EGFR, HER2, HER3 and HER4 receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated.

The expression "HER2" refers to human HER2 protein described, for example, in Semba et al., *PNAS* (USA) 82:6497-6501 (1985) and Yamamoto et al. *Nature* 319:230-234 (1986) (Genebank accession number X03363).

Figure 1:
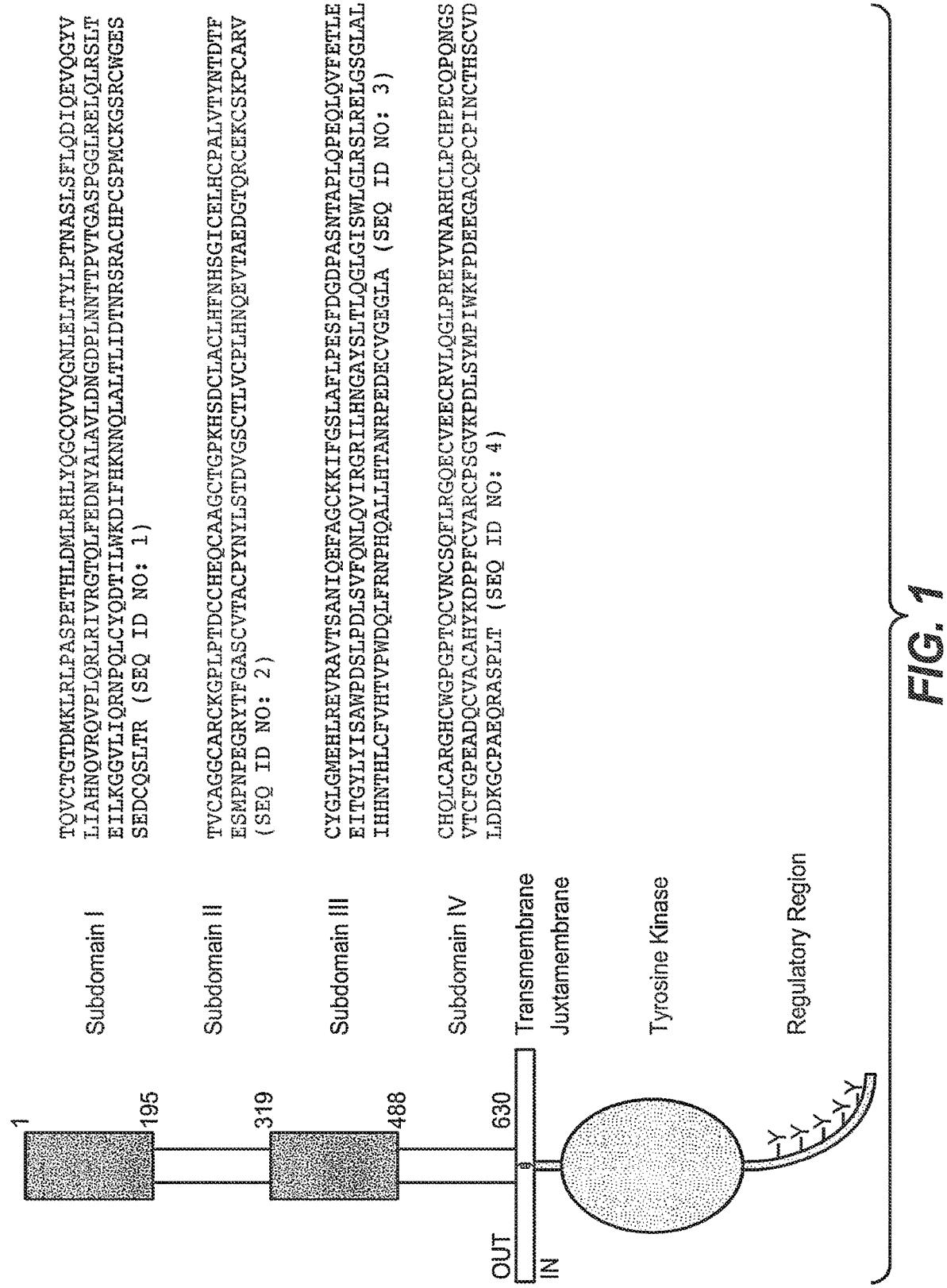
FIG. 1 provides a schematic of the HER2 protein structure, and amino acid sequences for Subdomains I-IV (SEQ ID Nos.1-4, respectively) of the extracellular domain thereof.

Herein, "HER2 extracellular domain" or "HER2 ECD" refers to a domain of HER2 that is outside of a cell, either anchored to a cell membrane, or in circulation, including fragments thereof. The amino acid sequence of HER2 is shown in FIG. 1. In one embodiment, the extracellular domain of HER2 may comprise four domains: "Subdomain I" (amino acid residues from about 1-195; SEQ ID NO:1), "Subdomain II" (amino acid residues from about 196-319; SEQ ID NO:2), "Subdomain III" (amino acid residues from about 320-488: SEQ ID NO:3), and "Subdomain IV" (amino acid residues from about 489-630; SEQ ID NO:4) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), and Plowman et al. *Proc. Natl. Acad. Sci.* 90:1746-1750 (1993), as well as FIG. 1 herein.

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.,* 269(20): 14661-14665 (1994), for example. Other proteins, such as a cytokine receptor subunit (e.g. gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). Humanized HER2 antibodies specifically include Trastuzumab and humanized 2C4 antibodies such as Pertuzumab as described and defined herein.

An "intact antibody" herein is one which comprises two antigen binding regions, and an Fc region. Preferably, the intact antibody has a functional Fc region. In one embodiment, "intact Pertuzumab" has a molecular weight of about 145,197 Da measuring its peptide chains only.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 449 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K449 residues removed, antibody populations with no K449 residues removed, and antibody populations having a mixture of antibodies with and without the K449 residue.

Unless indicated otherwise, herein the numbering of the residues in an immunoglobulin heavy chain is that of the EU index as in Kabat et al., *Sequences of Proteins of Immunological Interest*, 5th Ed. Public Health Service, National Institutes of Health, Bethesda, MD (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "naked antibody" is an antibody that is not conjugated to a heterologous molecule, such as a cytotoxic moiety or radiolabel.

The term "main species antibody" or "wild type antibody" herein refers to the antibody amino acid sequence structure in a composition which is the quantitatively predominant antibody molecule in the composition. Preferably, the main species antibody is a HER2 antibody, such as an antibody that binds to Subdomain II of HER2, antibody that inhibits HER dimerization more effectively than Trastuzumab, and/or binds to a heterodimeric binding site on HER2. In one embodiment, the main species antibody is one comprising CDR-H1 (SEQ ID NO: 17 or 23), CDR-H2 (SEQ ID NO: 18), and CDR-H3 (SEQ ID NO: 19), CDR-L1 (SEQ ID NO: 20), CDR-L2 (SEQ ID NO: 21 or 24) and CDR-L3 (SEQ ID NO: 22), the VL and VH amino acid sequences in SEQ ID NOs. 7 and 8, respectively (see FIGS. 2A-2B), and optionally, the light chain amino acid sequences in SEQ ID NOs. 11 or 15 and heavy chain amino acid sequences in SEQ ID NOs. 12 or 16 (see FIGS. 3A-3B and 5A-5B). In one embodiment, the main species antibody is Pertuzumab.

An antibody which "inhibits HER dimerization" is an antibody which inhibits, or interferes with, formation of a HER dimer or heterodimer. In one embodiment, such an antibody binds to HER2 at the heterodimeric binding site thereof. The most preferred dimerization inhibiting antibody herein is Pertuzumab.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Subdomain II of HER2 (SEQ ID NO: 2). Franklin et al. *Cancer Cell* 5:317-328 (2004).

A HER2 antibody that "binds to a heterodimeric binding site" of HER2, binds to residues in Subdomain II (SEQ ID NO: 2) and optionally also binds to residues in other of the domains of the HER2 extracellular domain, such as Subdomains I and III (SEQ ID NOs: 1 and 3), and can sterically hinder, at least to some extent, formation of a HER2-EGFR, HER2-HER3, or HER2-HER4 heterodimer. Franklin et al. *Cancer Cell* 5:317-328 (2004) characterize the HER2-Pertuzumab crystal structure, deposited with the RCSB Protein Data Bank (ID Code IS78), illustrating an exemplary antibody that binds to the heterodimeric binding site of HER2.

An antibody that "binds to Subdomain II" of HER2 binds to residues in Subdomain II (SEQ ID NO: 2) and optionally residues in other Subdomain(s) of HER2, such as Subdomains I and III (SEQ ID NOs: 1 and 3, respectively).

Figure 22:
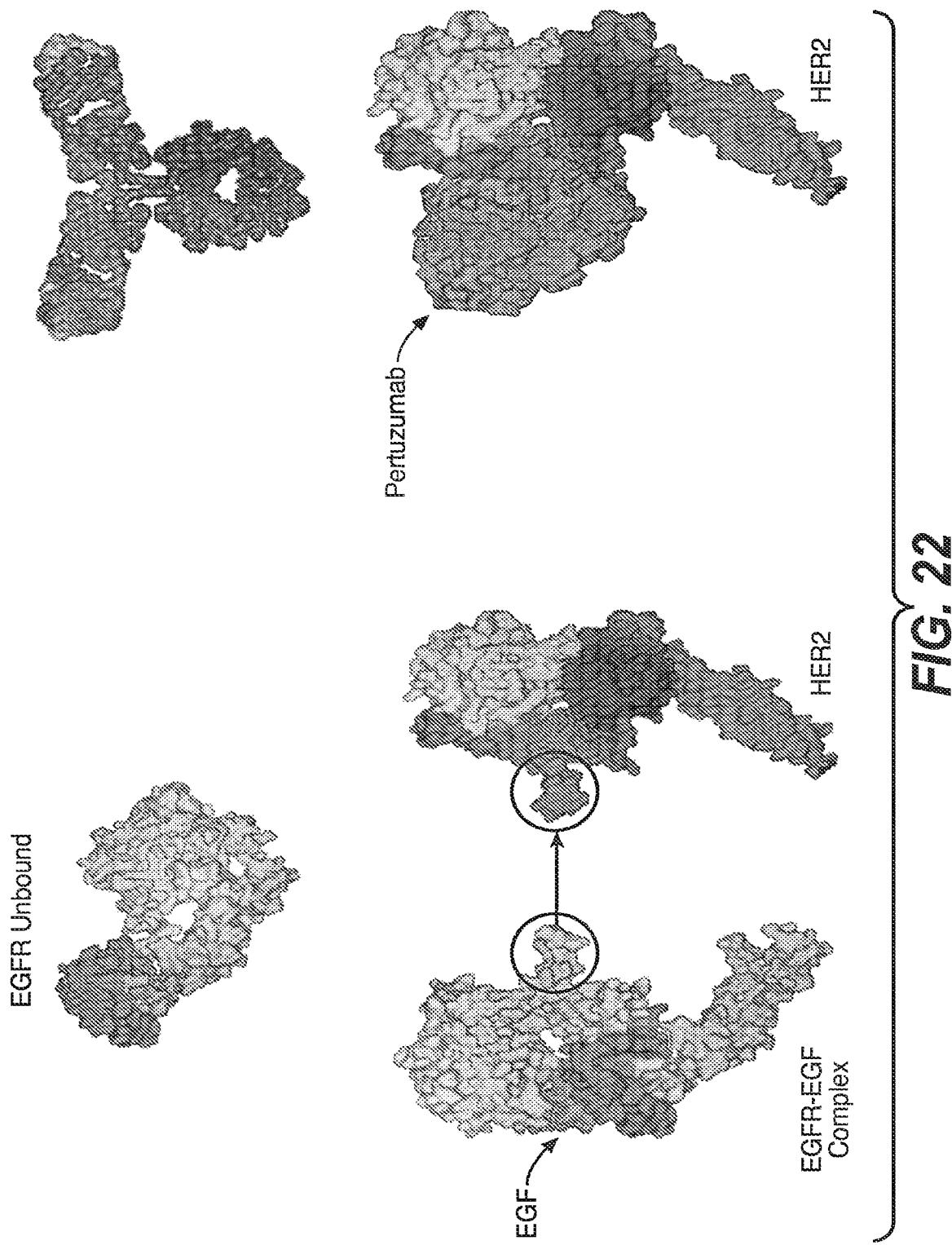
FIG. 22 depicts schematically binding of Pertuzumab at the heterodimeric binding site of HER2, thereby preventing heterodimerization with activated EGFR or HER3.

For the purposes herein, "Pertuzumab" and "rhuMAb 2C4", which are used interchangeably, refer to an antibody comprising the variable light (VL) and variable heavy (VH) amino acid sequences in SEQ ID NOs: 7 and 8, respectively. FIGS. 22 and 23 herein illustrate exemplary biological functions of Pertuzumab. Where Pertuzumab is an intact antibody, it preferably comprises an IgG1 antibody; in one embodiment comprising the light chain amino acid sequence in SEQ ID NO: 11 or 15, and heavy chain amino acid sequence in SEQ ID NO: 12 or 16. The antibody is optionally produced by recombinant Chinese Hamster Ovary (CHO) cells. The terms "Pertuzumab" and "rhuMAb 2C4" herein cover biosimilar or intended copies of the drug with the United States Adopted Name (USAN) or International Nonproprietary Name (INN): Pertuzumab.

For the purposes herein, "Trastuzumab" and rhuMAb4D5", which are used interchangeably, refer to an antibody comprising the variable light (VL) and variable heavy (VH) amino acid sequences from within SEQ ID Nos: 13 and 14, respectively (see FIGS. 4A-4B). Where Trastuzumab is an intact antibody, it preferably comprises an IgG1 antibody; in one embodiment comprising the light chain amino acid sequence of SEQ ID NO: 13 and the heavy chain amino acid sequence of SEQ ID NO: 14. The antibody is optionally produced by Chinese Hamster Ovary (CHO) cells. The terms "Trastuzumab" and "rhuMAb4D5" herein cover biosimilar or intended copies of the drug with the United States Adopted Name (USAN) or International Nonproprietary Name (INN): Trastuzumab.

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, and more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include deamidated antibody variant, antibody with an amino-terminal leader extension (e.g. VHS-) on one or two light chains thereof, antibody with a C-terminal lysine residue on one or two heavy chains thereof, etc, and includes combinations of variations to the amino acid sequences of heavy and/or light chains.

An "acidic variant" is a variant of the main species antibody which is more acidic than the main species antibody. An acidic variant has gained negative charge or lost positive charge relative to the main species antibody. Such acidic variants can be resolved using a separation methodology, such as ion exchange chromatography, that separates proteins according to charge. Acidic variants of a main species antibody elute earlier than the main peak upon separation by cation exchange chromatography.

A "disulfide reduced variant" has one or more inter-chain disulfide-bonded cysteine(s) chemically reduced to the free thiol form. This variant can be monitored by non-reduced Capillary Electrophoresis with Sodium Dodecyl Sulfate (CE-SDS), e.g. as described in WO 2009/099829 (Harris et al.).

Herein, a "non-reducible variant" or "incompletely reduced variant" is a variant of the main species antibody that cannot be chemically reduced to heavy chain and light chain by treatment with a reducing agent such as dithiothreitol. Such variants can be assessed by treating the composition with a reducing agent and evaluating the resulting composition using a methodology that evaluates protein size, such as Capillary Electrophoresis with Sodium Dodecyl Sulfate (CE-SDS), for instance using the techniques described in WO 2009/099829 (Harris et al.).

A "glycosylation variant" antibody herein is an antibody with one or more carbohydrate moeities attached thereto which differ from one or more carbohydrate moieties attached to a main species antibody. In one embodiment, the glycosylation variant has oligosaccharide structures attached to one or both heavy chains of an antibody, e.g. at residue 299 of the heavy chain. In one embodiment, the main species antibody (e.g. Pertuzumab) comprises G0 oligosaccharide as the predominant oligosaccharide attached to its Fc region. Exemplary oligosaccharide structures attached to IgG1 are depicted in FIGS. 24A-24B. Examples of glycosylation variants herein include afucosylated variant, antibody with a G1 or G2 oligosaccharide structure, instead a G0 oligosaccharide structure, attached to an Fc region thereof ("G1 glycosylation variant" or "G2 glycosylation variant"), antibody with no carbohydrate attached to one or two heavy chains of the antibody ("non-glycosylated heavy chain variant"), sialylated variant, etc, as well as combinations of such glycosylation alterations. See, e.g. U.S. Pat. No. 7,560,111 (Kao et al.).

Where the antibody has an Fc region, an oligosaccharide structure may be attached to one or two heavy chains of the antibody, e.g. at residue 299. In one embodiment, G0 is the predominant oligosaccharide structure, with other oligosaccharide structures such as G0-F, G-1, Man5, Man6, G1-1, G1(1-6), G1(1-3) and G2 being found in lesser amounts in the composition.

Unless indicated otherwise, a "G1 oligosaccharide structure" herein includes G1(1-6) and G1(1-3) structures.

For the purposes herein, "sialylated variant" is a variant of the main species antibody comprising one or more sialylated carbohydrate moieties attached to one or two heavy chains thereof. A sialylated variant can be identified by evaluating a composition (for example by ion exchange chromatography) with or without sialidase treatment, e.g. as described in WO 2009/099829.

A "glycated variant" is an antibody to which a sugar, such as glucose, has been covalently attached, e.g. to one or both light chains thereof. This addition can occur by reaction of glucose with a lysine residue on the protein (e.g. in cell culture media). A glycated variant can be identified by mass spectrometry analysis of the reduced antibody evaluating the increase in mass of heavy or light chains. A glycated variant can also be quantified by boronate chromatography as explained in WO 2009/099829 (Harris et al.).

A "deamidated" antibody is one in which one or more asparagine residues thereof has been derivitized, e.g. to an aspartic acid, a succinimide, or an iso-aspartic acid. An example of a deamidated antibody is a pertuzumab variant, wherein Asn-386 and/or Asn-391 on one or two heavy chains of pertuzumab are deamidated. See WO 2009/099829 (Harris et al.), for example.

An "amino-terminal leader extension variant" herein refers to a main species antibody with one or more amino acid residues of the amino-terminal leader sequence at the amino-terminus of any one or more heavy or light chains of the main species antibody. An exemplary amino-terminal leader extension comprises or consists of three amino acid residues, VHS-, present on one or both light chains of an antibody variant, designated a "VHS-variant" herein. See, U.S. Pat. No. 7,560,111 (Kao et al.).

A "C-terminal lysine variant" refers to a variant comprising a lysine (K) residue at the C-terminus of the heavy chain thereof. See, U.S. Pat. No. 7,560,111 (Kao et al.).

A "methionine-oxidized variant" refers to a variant comprising one or more oxidized methionine residues therein, e.g. oxidized Met-254. See, U.S. Pat. No. 7,560,111 (Kao et al.).

The term "cancer" refers to the physiological condition in mammals that is typically characterized by unregulated cell growth. Examples of cancer herein include breast cancer (e.g. metastatic breast cancer), gastric (or stomach) cancer, ovarian cancer, primary peritoneal cancer, and fallopian tube cancer. Examples of cancer herein include HER2-positive cancer and low HER3 cancer.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

A "HER2-positive" cancer comprises cancer cells which have higher than normal levels of HER2. Examples of HER2-positive cancer include HER2-positive breast cancer and HER2-positive gastric cancer. Methods for identifying HER2-positive cancer include: assays that measure HER2 protein such as immunohistochemistry assay (IHC), assays that measure HER2-encoding nucleic acid such as in situ hybridization (ISH), including fluorescent in situ hybridization (FISH; see WO98/45479 published October, 1998) and chromogenic in situ hybridization (CISH; see, e.g. Tanner et al., *Am. J. Pathol.* 157(5): 1467-1472 (2000); Bella et al., *J. Clin. Oncol.* 26: (May 20 suppl; abstr 22147) (2008)), southern blotting, or polymerase chain reaction (PCR) techniques, such as quantitative real time PCR (qRT-PCR); shed antigen (e.g. HER2 ECD) assays (see, e.g., U.S. Pat. No. 4,933,294 issued Jun. 12, 1990; and U.S. Pat. No. 5,401,638 issued Mar. 28, 1995); and in vivo assays. Optionally, HER2-positive cancer has an immunohistochemistry (IHC) score of 2+ or 3+ and/or an in situ hybridization (ISH) amplification ratio ≥2.0.

A "low HER3" cancer comprises cancer cells which have lower than normal levels of HER3. Examples of low HER3 cancers include ovarian, primary peritoneal, and fallopian tube carcinoma. See, for example, U.S. Pat. No. 7,981,418 (Amler et al.). In one embodiment, low HER3 is determined based on HER3 mRNA expression levels (concentration ratio equal or lower than 2.81, as assessed by qRT-PCR on a COBAS z480® instrument).

The "epitope 2C4" is the region in the extracellular domain of HER2 to which the antibody 2C4 binds. In order to screen for antibodies which bind essentially to the 2C4 epitope, a routine cross-blocking assay such as that described in *Antibodies, A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds essentially to the 2C4 epitope of HER2. Epitope 2C4 comprises residues from Subdomain II (SEQ ID NO: 2) in the extracellular domain of HER2. 2C4 and Pertuzumab binds to the extracellular domain of HER2 at the junction of Subdomains I, II and III (SEQ ID NOs: 1, 2, and 3, respectively). Franklin et al. *Cancer Cell* 5:317-328 (2004).

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m$^2$ dose, but rather as an absolute amount of the therapeutic agent.

A "container" refers to an object that can be used to hold or contain a pharmaceutical composition or composition. Examples of containers herein include a vial, syringe, intravenous bag, etc.

An "intravenous bag" or "IV bag" is a bag that can hold a solution which can be administered via the vein of a patient. In one embodiment, the solution is a saline solution (e.g. about 0.9% or about 0.45% NaCl). Optionally, the IV bag is formed from polyolefin or polyvinal chloride.

A "vial" is a container suitable for holding a liquid or lyophilized preparation. In one embodiment, the vial is a single-use vial, e.g. a 20-cc single-use vial with a stopper.

A "package insert" is a leaflet that, by order of the Food and Drug Administration (FDA) or other regulatory authority, must be placed inside the package of every prescription drug. The leaflet generally includes the trademark for the drug, its generic name, and its mechanism of action; states its indications, contraindications, warnings, precautions, adverse effects, and dosage forms; and includes instructions for the recommended dose, time, and route of administration.

A "pharmaceutical composition" is a composition comprising a pharmaceutically active drug (e.g. Pertuzumab and variant forms such as those disclosed herein) and one or more "pharmaceutically active excipients" (e.g. buffer, stabilizer, tonicity modifier, preservative, surfactant, etc) that can be safely administered to a human patient. Such compositions may be liquid or lyophilized, for example.

A "recombinant" protein is one which has been produced by a genetically modified host cell, such as a Chinese Hamster Ovary (CHO) host cell.

"Manufacturing scale" refers to production of a protein drug (e.g. antibody) at a commercial scale, e.g. at 12,000 liter (L) or more, using a commercial process approved by the FDA or other regulatory authority.

"Purifying" refers to one or more purification steps, such as Protein A chromatography, ion exchange chromatography, etc.

"Isolated" variant refers to the variant which has been separated from the main species or wild-type antibody by one or more purification or analytical procedures. Such isolated variant can be evaluated for its biological activity and/or potency.

II. Antibody Compositions

Main Species Antibody

The antibody compositions herein comprise an antibody that binds HER2 (a HER2 antibody), optionally a humanized HER2 antibody. The humanized antibodies herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises VH CDR residues:

GFTFTDYTMX (SEQ ID NO: 17), where X is preferably D or S, e.g. GFTFTDYTMD (SEQ ID NO: 23) for CDR-H1;

DVNPNSGGSIYNQRFKG (SEQ ID NO: 18) for CDR-H2; and/or

NLGPSFYFDY (SEQ ID NO: 19) for CDR-H3, optionally comprising amino acid modifications of those CDR residues, e.g. where the modifications essentially maintain or improve affinity of the antibody. For example, an antibody variant for use in the methods of the present invention may have from about one to about seven or about five amino acid substitutions in the above variable heavy CDR sequences. Such antibody variants may be prepared by affinity maturation, e.g., as described below.

The humanized antibody may comprise VL CDR residues:

KASQDVSIGVA (SEQ ID NO: 20) for CDR-L1;

SASYX$^1$X$^2$X$^3$, where X$^1$ is preferably R or L, X$^2$ is preferably Y or E, and X$^3$ is preferably T or S (SEQ ID NO: 21), e.g. SASYRYT (SEQ ID NO: 24) for CDR-L2; and/or QQYYIYPYT (SEQ ID NO: 22) for CDR-L3, e.g. in addition to those variable heavy domain CDR residues in the preceding paragraph.

Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation.

The present application also contemplates affinity matured antibodies which bind HER2. The parent antibody may be a human antibody or a humanized antibody, e.g., one comprising the variable light and/or variable heavy sequences of SEQ ID NOs. 7 and 8, respectively (i.e. comprising the VL and/or VH of Pertuzumab). An affinity matured variant of Pertuzumab preferably binds to HER2 receptor with an affinity superior to that of murine 2C4 or Pertuzumab (e.g. from about two or about four fold, to about 100 fold or about 1000 fold improved affinity, e.g. as assessed using a HER2 ECD ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody. Alternatively, the humanized antibody or affinity matured antibody may be an intact antibody, such as an intact IgG1 antibody.

Preferably, the HER2 antibody (either or both of the main species HER2 antibody and antibody variant thereof) is one which binds to Subdomain II of HER2, inhibits HER dimerization more effectively than Trastuzumab, and/or binds to a heterodimeric binding site of HER2. The preferred embodiment herein of the main species antibody is one comprising the variable light and variable heavy amino acid sequences in SEQ ID Nos. 3 and 4, and most preferably comprising the light chain amino acid sequences in SEQ ID No. 11 or 15 and heavy chain amino acid sequence in SEQ ID No. 12 or 16.

(ii) Unpaired Cysteine Variants

Examples 1 and 3 herein describe unpaired cysteine variants of Pertuzumab. Analytical assays for isolating, characterizing, and quantifying such variants include assays which specifically evaluate intra-chain disulfide bonds (as distinct from inter-chain disulfide bonds), for example, Hydrophobic Interaction Chromatography (HIC) analysis of antibody fragments (e.g. of Fab fragment) as in Example 1, HIC of an intact antibody as in Example 1, peptide mapping analysis of differentially tagged antibodies as in Example 3, and/or Reversed Phase High Performance Liquid Chromatography (RP-HPLC) as in Example 3 herein and in Zhang et al. *Anal. Chem.* 84(16):7112-7123 (2012).

Generally, the predominant form of Pertuzumab comprises a disulfide bond between Cys23 and Cys88 in both of the VL domains of its two Fab domains. See FIG. 6.

One unpaired cysteine variant herein, a heterodimer variant, lacks the Cys23/Cys88 disulfide bond in the variable light (VL) domain of only one of it two Fab regions. See FIG. 20(b). This was determined to be the predominant unpaired cysteine variant.

A further unpaired cysteine variant herein, a homodimer variant, lacks the Cys23/Cys88 disulfide bonds in both of its Fab regions. See FIG. 20(c).

In one embodiment, the amount of the unpaired cysteine variant in the composition (including homodimer and heterodimer variant) is ≤about 25%, for example, as determined by Fab hydrophobic interaction chromatography (HIC).

In one embodiment, the amount of the homodimer variant in the composition is ≤4.9% as determined by HIC of intact antibody.

In one embodiment, the amount of heterodimer variant in the composition is from about 13% to about 18%, for example, as determined by HIC of intact antibody.

The composition optionally further comprises one or more additional variants as described below.

The invention also concerns an isolated unpaired cysteine variant of Pertuzumab, wherein the unpaired cysteine variant comprises Cys23/Cys88 unpaired cysteines in one or both variable light domains of Pertuzumab. Such isolated unpaired cysteine variant may comprise or consist of a heterodimer variant and/or a homodimer variant. Such variants can be isolated using HIC or other purification methods, and may be subjected to a biological assay such as the potency assay (using HER2-positive breast cancer cells) as in Example 1 below.

(iii) Afucosylated Variant

Examples 2 and 4 herein describe afucosylated variants of Pertuzumab and demonstrate how to determine ADCC activity based on the percentage of afucosylated Pertuzumab in a composition.

In one embodiment, the invention concerns a composition comprising Pertuzumab and an afucosylated variant of Pertuzumab, wherein the amount of the afucosylated variant is greater than 2% of the composition. See, for example, anti2C4907-2, and Run 1 in Table 9 below.

In an alternative embodiment, the invention concerns a composition comprising Pertuzumab and an afucosylated variant of Pertuzumab, wherein the amount of the afucosylated variant is from 0.9 to 4.1% of the composition. This amount of afucosylated variant may, for example, be quantified using the validated CE-LIF assay in Example 4.

Optionally, the composition further comprises the unpaired cysteine variants (heterodimer and/or homodimer as described in the previous section) and/or additional variants to be described below.

(iv) LMWS and HMWS

The invention further concerns a low-molecular-weight species (LMWS) of Pertuzumab and/or high-molecular-weight-species (HMWS) of Pertuzumab in either isolated form or in compositions comprising the variant(s) and the main species antibody. The LMWS and HMWS can be isolated, characterized, and quantified using various techniques, including, without limitation, size exclusion high performance liquid chromatography (SE-HPLC), and/or Capillary Electrophoresis Sodium Dodecyl Sulfate (CE-SDS).

Using SE-HPLC assay (e.g. as in Example 5), the amount of main species Pertuzumab and HMWS or LMWS in a composition may be:
Main Peak: ≥about 96%, e.g., ≥about 96.7%, ≥about 97.3%, e.g., ≥about 97.4%.
HMWS: ≤about 2%, e.g., ≤about 1.7%, e.g., ≤about 1.5%, e.g. ≤about 1.4%, e.g. ≤about 0.8%.
LMWS: ≤about 2%, e.g., ≤about 1.6%, e.g., ≤about 1.2%, e.g. ≤about 0.6%.

Using NR-CE-SDS assay (e.g. as in Example 5), the amount of main species Pertuzumab and HMWS or LMWS in a composition may be:
Main Peak: ≥about 95%, e.g., ≥about 96.0%, e.g., ≥about 97.8%
HMWS: ≤about 1%, e.g. ≤about 0.6%.
LMWS: ≤about 4%, e.g. ≤about 3.4%.

For example, the amount of Main Peak or main species Pertuzumab (excluding LMWS and HMWS) as determined by CE-SDS may be about 95% to about 99%, e.g., from about 96.0% to about 97.8%, e.g. from about 95.3% to about 97.3% Main Peak.

Optionally, the LMWS comprises or consists of "Peak 6" as obtained by NR-CE-SDS (see, e.g. Example 5). Such Peak 6 may be determined to be about 0.9% to about 2.3%, e.g. about 2% to about 2.3% of the composition.

(v) Peak 1 and Peak 2 Fragments of Pertuzumab

The invention further concerns a Peak 1 fragment(s) and/or Peak 2 fragment(s) of Pertuzumab in either separated or isolated form or in compositions comprising the fragment (s) and the main species antibody. Peak 1 and Peak 2 can be isolated, characterized, and quantified using various techniques, including, without limitation, size exclusion high performance liquid chromatography (SE-HPLC), and/or Capillary Electrophoresis Sodium Dodecyl Sulfate (CE-SDS), including R-CE-SDS and NR-CE-SDS. In one embodiment, Peak 1 and Peak 2 are separated and/or analyzed by R-CE-SDS, e.g. as described in Examples 5 and 6 and the corrected peak area (CPA) provides the % Peak 1 or Peak 2 in the composition.

Using R-CE-SDS assay (e.g. as in Examples 5 and 6), the amount of Peak 1 in a composition is ≤5% (e.g. from 0.13% to 0.41% CPA) and the amount of Peak 2 in a composition is ≤1.0% (e.g. from 0.47% to 0.74% CPA).

(vi) Additional Variants

The compositions herein optionally comprise additional variants of Pertuzumab such as those described in U.S. Pat. No. 7,560,111 (Kao et al.) and/or in WO 2009/099829 (Harris et al.).

Examples of such additional variants include, without limitation, any one or more of: glycated variant, disulfide reduced variant, non-reducible variant, deamidated variant, sialylated variant, VHS-variant, C-terminal lysine variant, methionine-oxidized variant, afucosylated variant, G1 glycosylation variant, G2 glycosylation variant, and non-glycosylated heavy chain variant.

For example, the composition may comprise acidic variants (see WO 2009/099829, Harris et al.), wherein the acidic variants in the composition may include one, two, three, four, or five of glycated variant, deamidated variant, disulfide reduced variant, sialylated variant, and non-reducible variant. Preferably, the total amount of all acidic variants in the composition is less than about 25%. In one embodiment, the glycated variant, deamidated variant, disulfide reduced variant, sialylated variant, and non-reducible variant constitute at least about 75-80% of the acidic variants in the composition.

Acidic variants may be evaluated by a variety of methods, but preferably such methods include one, two, three, four, or five of: ion exchange chromatography (IEC) wherein the composition is treated with sialidase before, after, and/or during the IEC (e.g. to evaluate sialylated variant), reduced CE-SDS (e.g. to evaluate disulfide reduced variant), non-reduced CE-SDS (e.g to evaluate non-reducible variant), boronate chromatography (e.g. to evaluate glycated variant), and peptide mapping (e.g. to evaluate deamidated variant).

The composition optionally includes an amino-terminal leader extension variant. Preferably, the amino-terminal leader extension is on a light chain of the antibody variant (e.g. on one or two light chains of the antibody variant). The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS- (i.e. VHS-variant). Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the lower detection limit of any assay (preferably cation exchange analysis) used to detect the variant to an amount less than the amount of the main species antibody. Generally, about 20% or less (e.g. from about 1% to about 15%, for instance from 5% to about 15%, and preferably from about 8% to about 12%) of the antibody molecules in the composition comprise an amino-terminal leader extension. Such percentage amounts are preferably determined using cation exchange analysis.

Further amino acid sequence alterations of the main species antibody and/or variant are contemplated, including but not limited to an antibody comprising a C-terminal lysine residue on one or both heavy chains thereof (such an antibody variant may be present in an amount from about 1% to about 20%), antibody with one or more oxidized methionine residues (for example, Pertuzumab comprising oxidized Met-254) etc.

Moreover, aside from the afucosylated variant and sialylated variant discussed above, the main species antibody or variant may comprise additional glycosylation variations, non-limiting examples of which include antibody comprising a G1 or G2 oligosaccharide structure attached to the Fc region thereof, antibody comprising one or two non-glycosylated heavy chains, etc.

III. Manufacturing and Analytical Methods

According to one embodiment of the invention, a method for evaluating a Pertuzumab composition is provided which comprises one, two, three, or four of: (1) measuring the amount of unpaired cysteine variant in the composition, wherein the unpaired cysteine variant comprises Cys23/Cys88 unpaired cysteines in one or both variable light domains of Pertuzumab, and/or (2) measuring the amount of afucosylated Pertuzumab in the composition, and/or (3) measuring the amount of low-molecular-weight-species (LMWS) of Pertuzumab in the composition, and/or (4) measuring the amount of high-molecular-weight-species (HMWS) of Pertuzumab in the composition. Optionally, all four analytical assays are performed on a composition comprising Pertuzumab and variants thereof.

The invention also concerns a method for making a composition comprising: (1) producing a composition comprising Pertuzumab and one or more variants thereof, and (2) subjecting the composition so-produced to one or more analytical assay(s) to evaluate the amount of the variant(s) therein. The analytical assay(s) can evaluate and quantify the amount of any one or more of: (i) unpaired cysteine variant comprising Cys23/Cys88 unpaired cysteines in one or both variable light domains of Pertuzumab and/or (ii) a heterodimer variant comprising Cys23/Cys88 unpaired cysteines in only one variable light domain of Pertuzumab and/or (iii) a homodimer variant comprising Cys23/Cys88 unpaired cysteines in both variable light domains of Pertuzumab and/or (iv) afucosylated variant of Pertuzumab and/or (v) high-molecular-weight-species (HMWS) of Pertuzumab and/or (vi) low-molecular-weight-species (LMWS) of Pertuzumab, and/or (vii) Peak 1 fragment(s) of Pertuzumab and/or (viii) Peak 2 fragment(s) of Pertuzumab. Thus, one, two, three, four, five, six, seven or eight of these variants can be analyzed.

Optionally, the analytical assay evaluates, quantifies, or isolates unpaired cysteine variant, including heterodimer and/or homodimer variants. For example, the analytical assay may comprises Hydrophobic Interaction Chromatography (HIC) of an antibody fragment (e.g. Fab fragment) or of an intact antibody (see, e.g. Example 1), peptide mapping analysis (see, e.g. Example 3), or Reversed Phase High Performance Liquid Chromatography (HPLC) (see, e.g., Example 3).

In one embodiment, the amount of the unpaired cysteine variant (heterodimer and/or homodimer variant) in the composition is ≤about 25% as determined by Fab hydrophobic interaction chromatography (HIC).

In one embodiment, the amount of the homodimer variant in the composition is ≤4.9% as determined by hydrophobic interaction chromatography (HIC) of intact antibody.

In one embodiment, the amount of the heterodimer variant in the composition is from about 13% to about 18% as determined by hydrophobic interaction chromatography (HIC) of intact antibody.

Optionally, the analytical assay evaluates, quantifies, or isolates afucosyled variant. The amount of afucosylation can be used to determine or quantify biological activity, e.g. ADCC, of the composition.

In addition, the method comprises evaluating the biological activity of a Pertuzumab composition comprising measuring the amount of afucosylated Pertuzumab variant in the composition to determine the antibody-dependent cell-mediated cytotoxicity (ADCC) activity of the composition, and confirming the amount of afucosylated Pertuzumab is in the range from about 0.9% to about 4.1%. For instance, the method comprises measuring the amount of afucosylated Pertuzumab using capillary electrophoresis-laser-induced fluorescence (CE-LIF).

Optionally, the analytical assay for evaluating afucosylation is capillary electrophoresis (CE), including capillary electrophoresis-laser-induced fluorescence (CE-LIF), see, Examples 2 and 4 below. The amount of afucosylated variant is optionally from about 0.9 to about 4.1% of the composition (e.g. as measured by CE-LIF in Example 4). In one embodiment, the amount of afucosylated variant is greater than 2% of the composition (e.g. as measured by CE-LIF in Example 4).

Optionally, the analytical assay evaluates, quantifies, or isolates low-molecular-weight species (LMWS) and/or high-molecular-weight-species (HMWS) of Pertuzumab. Exemplary assays include SE-HPLC and/or CE-SDS (see, for example, Example 5 below).

In one embodiment, the analytical assay comprises SE-HPLC (e.g. as in Example 5), and the amount of main species Pertuzumab, HMWS or LMWS in a composition thus analyzed is determined to be:
Main Peak: ≥about 96%, e.g., ≥about 96.7%, ≥about 97.3%, e.g., ≥about 97.4%.
HMWS: ≤about 2%, e.g., ≤about 1.7%, e.g., ≤about 1.5%, e.g. ≤about 1.4%, e.g. ≤about 0.8%.
LMWS: ≤about 2%, e.g., ≤about 1.6%, e.g., ≤about 1.2%, e.g. ≤about 0.6%.

In one embodiment, the analytical assay comprises CE-SDS (e.g. as in Example 5), and the amount of main species Pertuzumab and HMWS or LMWS Pertuzumab in a composition thus analyzed is determined to be:
Main Peak: ≥about 95%, e.g., ≥about 96.0%, e.g., ≥about 97.8%
HMWS: ≤about 1%, e.g. ≤about 0.6%.
LMWS: ≤about 4%, e.g. ≤about 3.4%.

In one embodiment, a composition is evaluated by NR-CE-SDS, and the amount of Main Peak or main species Pertuzumab (excluding LMWS and HMWS) is found to be from about 95% to about 99%, e.g., from about 96.0% to about 97.8%, e.g. from about 95.3% to about 97.3% of the composition thus analyzed.

In one embodiment, the amount of "Peak 6" in a composition is evaluated by CE-SDS (see, e.g. Example 5), and the amount of Peak 6 LMWS is determined to be about 0.9% to about 2.3%, e.g. about 2% to about 2.3% of a composition thus analyzed.

In one embodiment, the amount of Peak 1 and/or Peak 2 in a composition is evaluated by R-CE-SDS (see, e.g. Examples 5 and 6), and the amount of Peak 1 is determined to be ≤5% (e.g. from 0.13% to 0.41% CPA) and the amount of Peak 2 is determined to be ≤1.0% (e.g. from 0.47% to 0.74% CPA).

The methods optionally further comprise combining the purified composition with one or more pharmaceutically acceptable excipients to make a pharmaceutical composition. In addition, the pharmaceutical composition can be put into a container which is packaged together with a package insert (e.g. with prescribing information instructing the user thereof to use the pharmaceutical composition to treat cancer) so as to make an article of manufacture.

IV. Pharmaceutical Compositions

Pharmaceutical compositions comprising Pertuzumab and variants thereof are prepared for storage by mixing the composition having the desired degree of purity with optional pharmaceutically acceptable excipients (*Remington's Pharmaceutical Sciences* 16th edition, Osol, A. Ed. (1980)), generally in the form of lyophilized formulations or aqueous solutions. Antibody crystals are also contemplated (see US Pat Appln 2002/0136719). Pharmaceutically acceptable excipients are nontoxic to recipients at the dosages and concentrations employed, and include buffers such as histidine acetate; antioxidants including ascorbic acid and methionine; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polysorbates (e.g. polysorbate 20 or 80), PLURONICS™ or polyethylene glycol (PEG).

Lyophilized antibody formulations are described in U.S. Pat. Nos. 6,267,958, 6,685,940 and 6,821,515, expressly incorporated herein by reference. An exemplary Trastuzumab pharmaceutical composition is a sterile, white to pale yellow preservative-free lyophilized powder for intravenous (IV) administration, comprising 440 mg Trastuzumab, 400 mg α,α-trehalose dehydrate, 9.9 mg L-histidine-HCl, 6.4 mg L-histidine, and 1.8 mg polysorbate 20. Reconstitution of 20 mL of bacteriostatic water for injection (BWFI), containing 1.1% benzyl alcohol as a preservative, yields a multi-dose solution containing 21 mg/mL Trastuzumab, at pH of approximately 6.0.

An exemplary Pertuzumab pharmaceutical composition for therapeutic use comprises 30 mg/mL Pertuzumab in 20 mM histidine acetate, 120 mM sucrose, 0.02% polysorbate 20, at pH 6.0. An alternate Pertuzumab formulation comprises 25 mg/mL Pertuzumab, 10 mM histidine-HCl buffer, 240 mM sucrose, 0.02% polysorbate 20, pH 6.0.

The pharmaceutical compositions to be used for in vivo administration must be sterile. This is readily accomplished by filtration through sterile filtration membranes.

V. Therapeutic Applications and Uses

The compositions herein can be used to treat cancer, such as HER2-positive breast cancer, e.g, metastatic or locally recurrent, unresectable breast cancer, or de novo Stage IV disease, is defined as immunohistochemistry (IHC) 3+ and/or fluorescence in situ hybridization (FISH) amplification ratio ≥2.0. Optionally, the patients in the population have not received previous treatment or have relapsed after adjuvant therapy, have a left ventricular ejection fraction (LVEF) of ≥50% at baseline, and/or have an Eastern Cooperative Oncology Group performance status (ECOG PS) of 0 or 1.

In an alternative embodiment, the composition can be used to treat early-stage HER2-positive breast cancer, e.g., in combination with Trastuzumab, and chemotherapy, wherein the chemotherapy comprises anthracycline-based chemotherapy, or carboplatin-based chemotherapy. In one embodiment, the chemotherapy comprises anthracycline-based chemotherapy, e.g. comprising 5-FU, epirubicin, and cyclophosphamide (FEC). In an alternative embodiment, the chemotherapy comprises carboplatin-based chemotherapy, e.g. comprising taxane (e.g. Docetaxel), Carboplatin in addition to HERCEPTIN®/Trastuzumab (e.g. TCH regimen). In one embodiment, the composition is administered concurrently with the anthracycline-based chemotherapy or with the carboplatin-based chemotherapy, e.g. wherein the Pertuzumab, Trastuzumab and chemotherapy are administered in 3-week cycles with Pertuzumab, Trastuzumab and the chemotherapy being administered on day-1 of each cycle. The early-stage HER2-positive breast cancer therapy contemplated herein includes neoadjuvant and adjuvant therapy.

In yet another embodiment, the composition can be used to treat HER2-positive gastric cancer, optionally in combination with Trastuzumab and a chemotherapy, such as a platin (e.g. cisplatin) and/or a fluoropurimidine (e.g. capecitabine and/or 5-fluorouracil (5-FU)).

In an alternative embodiment, the composition may be used to treat HER2-positive breast cancer optionally in combination with Trastuzumab and vinorelbine. The breast cancer according to this embodiment is optionally metastatic or locally advanced. Optionally, the patient has not previously received systemic non-hormonal anticancer therapy in the metastatic setting.

In another aspect, the composition is used to treat HER2-positive breast cancer in a patient comprising administering the composition, Trastuzumab, and aromatase inhibitor (e.g. anastrazole or letrozole) to the patient. According to this embodiment, the breast cancer is advanced breast cancer, including hormone receptor-positive breast cancer such as estrogen receptor (ER)-positive and/or progesterone receptor (PgR)-positive breast cancer. Optionally, the patient has not previously received systemic nonhormonal anticancer therapy in the metastatic setting. This treatment method optionally further comprises administering induction chemotherapy (e.g. comprising taxane) to the patient.

In an additional aspect, the composition is used to treat low HER3 cancer, such as ovarian cancer, primary peritoneal, or fallopian tube cancer. See, for example, U.S. Pat. No. 7,981,418 (Amler et al.) and U.S. Patent Publication US-2006-0013819-A1 (Kelsey, S.).

The antibodies and chemotherapeutic treatments are administered to a human patient in accord with known methods. Specific administration schedules and formulations are described in the examples herein.

According to one particular embodiment of the invention, approximately 840 mg (loading dose) of Pertuzumab is administered, followed by one or more doses of approximately 420 mg (maintenance dose(s)) of Pertuzumab. The maintenance doses are preferably administered about every 3 weeks, for a total of at least two doses, until clinical progressive disease, or unmanageable toxicity, e.g from 6 to 20 doses. Longer treatment periods, including more treatment cycles, are also contemplated.

According to another particular embodiment where the cancer is gastric cancer, Pertuzumab is administered at a dose of 840 mg for all treatment cycles.

VI. Articles of Manufacture

One embodiment of an article of manufacture herein comprises a container, such as a vial, syringe, or intravenous (IV) bag containing the composition or pharmaceutical composition herein. Optionally, the article of manufacture further comprises a package insert with prescribing information describing how to use the composition according to the previous section herein.

VII. Deposit of Biological Materials

The following hybridoma cell lines have been deposited with the American Type Culture Collection, 10801 University Boulevard, Manassas, VA 20110-2209, USA (ATCC):

| Antibody Designation | ATCC No. | Deposit Date |
|---|---|---|
| 4D5 | ATCC CRL 10463 | May 24, 1990 |
| 2C4 | ATCC HB-12697 | Apr. 8, 1999 |

Further details of the invention are illustrated by the following non-limiting Examples. The disclosures of all citations in the specification are expressly incorporated herein by reference.

Example 1

Cys23/Cys88 Unpaired Cysteine Variant of Pertuzumab and Characterization Thereof Pertuzumab is a humanized monoclonal antibody (MAb) based on a human IgG1(κ) framework. The recombinant antibody is produced by Chinese Hamster Ovary (CHO) cells and comprises two heavy chains (449 amino acid residues each) and two light chains (214 amino acid residues each) with inter-chain and intra-chain disulfide bonds. The light-chain and heavy-chain sequences of pertuzumab are shown in FIGS. 3A and 3B, respectively. The calculated molecular mass of intact pertuzumab is 145,197 Da (peptide chains only, without heavy-chain C-terminal lysine residue).

The CH2 domain of each heavy chain also has a single conserved glycosylation site at Asn299.

Pertuzumab differs from Trastuzumab (HERCEPTIN®) in the complementarity determining regions (CDRs) of the light chain (12 amino acid differences) and the heavy chain (29 amino acid differences), and the fact that it binds to a different epitope on the human epidermal growth factor receptor 2 (p185$^{HER2}$). Binding of pertuzumab to the HER2 receptor on human epithelial cells prevents HER2 from forming complexes with other members of the HER receptor family (including EGFR, HER3, HER4) and forming HER2 homodimers. By blocking complex formation, pertuzumab inhibits ligand-initiated intracellular signaling through two major signal pathways, mitogen-activated protein (MAP) kinase and phosphoinositide 3-kinase (PI3K), resulting in inhibition of cell proliferation and survival, respectively.

This example concerns the identification and characterization of an unpaired cysteine variant of Pertuzumab: the Cys23/Cys88 unpaired cysteine variant comprising unpaired cysteines in one or both light chains of the antibody.

Free sulfhydryls were measured using Ellman's reagent, and showed a reactive free sulfhydryl content of 0.1-0.3 moles per mole protein. Hydrophobic interaction chromatography (HIC) analysis and peptide map analysis revealed unpaired cysteine residues at Cys23 and Cys88 on one or both light chains. Using papain HIC, levels of the Fab variant containing free sulfhydryls at these sites were found to be 12.7%-13.5% in Pertuzumab materials produced using the commercial manufacturing process. HIC analysis of the intact antibody indicated that the two major forms are 78%-85% wild-type Pertuzumab and 13.4%-18.4% Pertuzumab heterodimer (unpaired cysteine pair on one arm).

Materials and Methods

Compositions Tested: This example describes the characterization of the current Pertuzumab Reference Standard Batch anti2C4907-2 and Run 1, representing Phase III clinical material, and five Phase III/commercial batches (Runs 3-7), all produced at 12,000 liter (L) scale using the commercial process. Comparison is also made to the previous Reference Standard Batch anti2C4-900-1, which is representative of the Phase I/II clinical material.

The compositions tested were drug substance batches formulated in the commercial formulation at 30 mg/mL in 20 mM L-histidine acetate, 120 mM sucrose, and 0.02% (w/v) polysorbate 20 at pH 6.0. Batch anti2C4-900-1 was formulated earlier in clinical development at 25 mg/mL in 10 mM L-histidine chloride, 240 mM sucrose, and 0.02% (w/v) polysorbate 20 at pH 6.0.

Disulfide Bond Analysis by Non-Reduced Peptide Map Analysis and Mass Spectrometry: To denature pertuzumab under non-reducing conditions and alkylate any buried free sulfhydryl groups, approximately 0.5 mg of pertuzumab in formulation buffer was mixed with denaturing buffer (consisting of 8 M GdHCl, 10 mM N-ethylmaleimide (NEM), 0.1 M sodium acetate, pH 5.0) and then incubated at 37° C. for 3 hours. The solution was buffer exchanged into 600 μL of 0.1 M Tris, 1 mM CaCl$_2$), pH 7.0 using NAP-5 columns. Acetonitrile (ACN) was added to each sample to achieve a concentration of 10%. The trypsin digestion was carried out at an enzyme to substrate ratio of 1:10 (w/w) at 37° C. for 16 hours. The resulting peptides were separated by RP-HPLC using the methods described below for sulfitolysis tryptic maps.

Sulfitolysis Tryptic Peptide Map: To generate the pertuzumab peptide maps, the protein was digested with trypsin after reduction and sulfitolysis of the cysteine residues. Aliquots (1 mg) of pertuzumab were added to 360 mM Tris-HCl pH 8.6, 6 M guanidine hydrochloride (GdHCl), 2 mM ethylenediaminetetraacetic acid (EDTA), 13 mM sodium sulfite, and 38 mM sodium tetrathionate for reduction and sulfitolysis of the cysteine residues. Samples were incubated at 37° C. for 20 minutes. Sulfitolyzed samples were loaded onto PD-10 columns and eluted with 10 mM Tris, 0.1 mM CaCl$_2$), pH 8.3. Following buffer exchange, 20 μL of a 10% octyl-B-glucoside solution and 20 μL of 1 mg/mL trypsin were added. Samples were incubated at 37° C. for 5 hours. The digestion reaction was quenched with 25 μL of 10% trifluoroacetic acid (TFA). The resulting peptides were separated by RP-HPLC using a Zorbax 300SB-C8 column (4.6 mm×150 mm). The peptides were separated after a 5 minute hold at initial conditions with a linear gradient from 0% to 17% solvent B in 57 minutes, to 32% solvent B at 149 minutes, to 45% solvent B at 162 minutes, and to 95% solvent B at 173 minutes. At 179 minutes, the column was reconditioned at 100% solvent A for 25 minutes, for a total run time of 204 minutes. Solvent A consisted of 0.1% TFA in water and solvent B consisted of 0.08% TFA in acetonitrile. The column was maintained at 37° C. and eluted at a flow rate of 0.5 mL/min. The elution profile was monitored at 214 nm and 280 nm. Masses of the tryptic peptides were determined by liquid chromatography-mass spectrometric (LC-MS) analysis of the separated digest mixture using an LTQ ORBITRAP™ mass spectrometer.

Free Sylfydryl Content by Ellman's Analysis: The Pertuzumab samples were buffer exchanged into reaction buffer (100 mM potassium phosphate, 1 mM EDTA, 8 M urea, pH 8) and adjusted to a concentration that resulted in free thiol concentrations within the standard curve range. A solution of dithionitrobenzene (DTNB) (10 mM) and a cysteine standard curve (eight points between 0 and 100 μM) were prepared in reaction buffer. On a 96-well plate, 165 μL of sample or standard were added to triplicate wells. The reaction was initiated by the addition of 10 μL of DTNB and then incubated for 30 minutes. After incubation, absorbance was measured at 412 nm using a SPECTRAMAX M$^2$® plate reader. The concentration of free thiol was calculated using the linear equation obtained from the standard curve. The concentration of the protein was determined using the absorbance at 280 nm obtained from a spectrophotometer. The free thiol is reported as moles of free thiol per mole of Pertuzumab.

Papain HIC: For papain-digested Pertuzumab samples, the samples were digested with papain after removing the C-terminal lysine with carboxypeptidase B (CpB). The Fab and Fc domains were separated by HIC using a PolyPropyl Aspartamide column (4.6 mm×100 mm, 1500 Å, 3 μm). Solvent A consisted of 1.6 M ammonium sulfate, 20 mM potassium phosphate, pH 6.05 and solvent B consisted of 20 mM potassium phosphate pH 6.05. The analytes were separated with a gradient from 0% to 18% solvent B from 3 to 6 minutes, to 24% solvent B at 21 minutes. The column was maintained at 25° C. with a flow rate of 0.8 mL/min. The elution profile was monitored at 280 nm.

HIC of Intact Antibody: Intact Pertuzumab samples were separated by HIC using a PolyPropyl Aspartamide column (9.4 mm×100 mm, 1500 Å, 3 μm). Solvent A consisted of 1.0 M ammonium sulfate, 20 mM potassium phosphate, pH 6.05 and solvent B consisted of 20 mM potassium phosphate, pH 6.05. The analytes were separated isocratically with 12% solvent B for 25 minutes. The column was maintained at 30° C. with a flow rate of 2 mL/min. The elution profile was monitored at 280 nm.

SDS-PAGE with Peptide Mass Fingerprinting: Both reduced and non-reduced Pertuzumab samples were analyzed by sodium dodecyl sulfate-polyacrylamide gel electrophoresis (SDS-PAGE). Samples (5 μg) were denatured by heating in the presence of SDS-PAGE sample buffer for 5-10 minutes at 60±2° C. with iodoacetamide for non-reduced samples. Samples were reduced for 15-20 minutes at 60° C.±2° C. in the presence of 80 mM dithiothreitol (DTT). The denatured samples were separated in 4%-20% polyacrylamide gradient gels and stained with SYPRO™ Ruby dye to obtain the protein banding pattern. Along with the pertuzumab samples, molecular weight standards and SYPRO™ Ruby—stain sensitivity standards (2 ng/lane and 8 ng/lane bovine serum albumin (BSA)) were included on the gels.

Peptide mass fingerprinting is an analytical technique for protein identification. The gels were loaded with 10 μg of commercial Reference Standard Batch anti2C4907-2 and Run 5. All bands separated by SDS-PAGE were cleaved into peptides by trypsin. The absolute masses of the peptides are accurately measured with BRUKER™ matrix-assisted laser desorption/ionization-time of flight mass spectrometry (MALDI-TOF MS). The peptide mass lists were used to identify proteins by searching protein sequences. All observed bands in both the non-reduced and reduced Pertuzumab were identified by peptide mass fingerprinting.

Potency by Bioassay: The Pertuzumab potency method assesses the potency of Pertuzumab by measuring its ability to inhibit proliferation of a human HER2-expressing breast cancer cell line. In a typical assay, 96-well microtiter plate(s) were seeded with the breast cancer cells and incubated in a humidified incubator. After incubation, the media was removed and varying concentrations of Pertuzumab Reference Standard, assay control, and sample(s) were added to the plate(s). The plate(s) were then incubated, and the relative number of viable cells was quantitated indirectly using a redox dye, ALAMARBLUE®. The fluorescence was measured using excitation at 530 nm and emission at 590 nm. ALAMARBLUE® is blue and nonfluorescent in its oxidized state, but is reduced by the cell's intracellular environment to a pink form that is highly fluorescent (Page et al. *Int. J. Oncol.* 3: 473-476 (1993)). The changes in color and fluorescence are proportional to the number of viable cells. The results, expressed in relative fluorescence units (RFU), were plotted against the Pertuzumab concentrations and a parallel line program was used to estimate the antiproliferative activity of Pertuzumab samples relative to the Reference Standard.

Results

Figure 7:
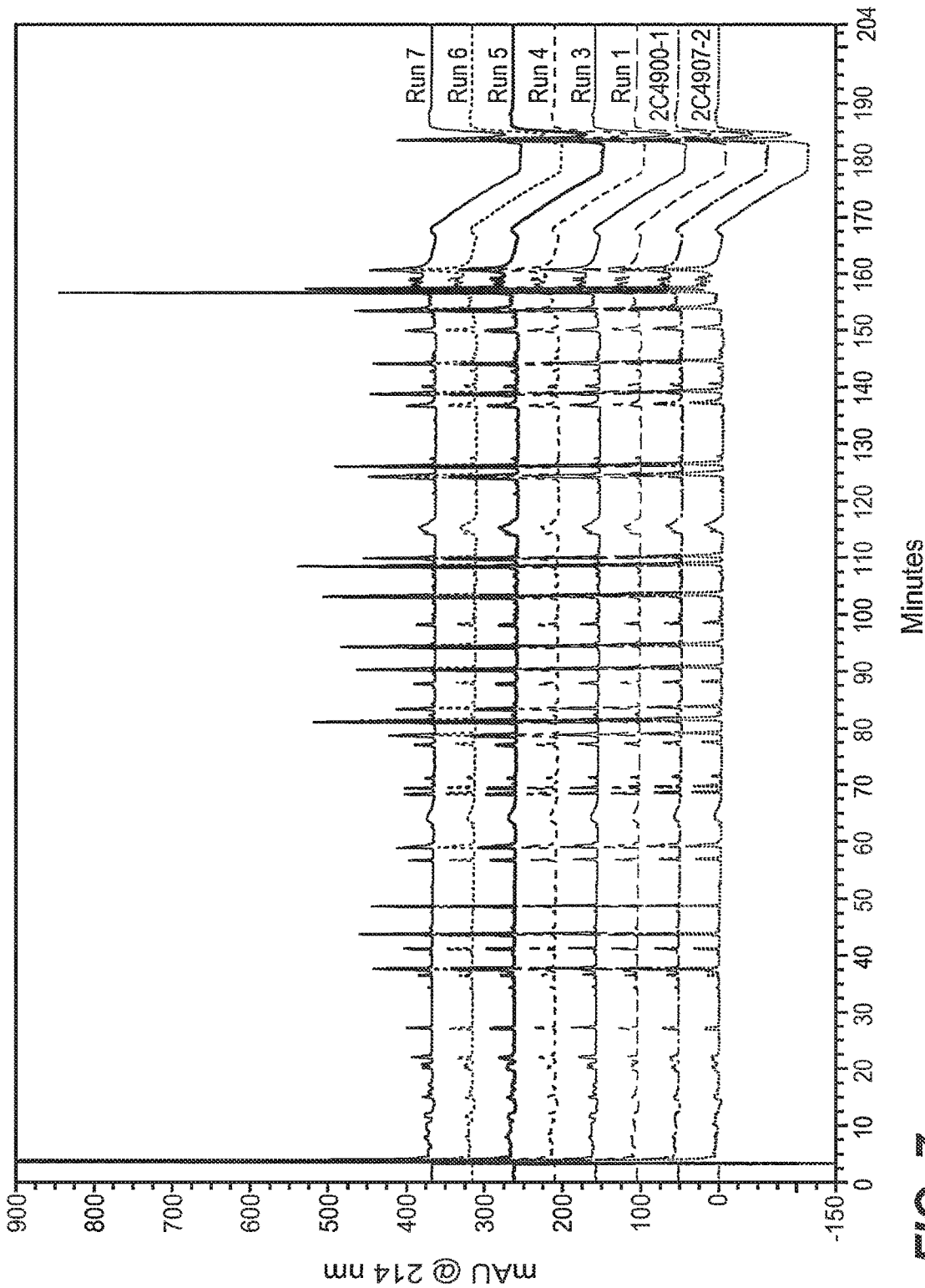
FIG. 7 shows non-reduced (native) trypic peptide maps of Pertuzumab.

Assignment of Disulfide Bonds: There are 32 cysteines in Pertuzumab, forming 16 disulfide bonds, of which four are inter-chain and 12 are intra-chain linkages. However, because of the multimeric nature of the molecule, there are only nine distinct disulfide bonds. The native protein was digested with trypsin to achieve release of all disulfide-linked peptides. The chromatographic profiles for the Pertuzumab batches are shown in FIG. 7. Reversed-phase LC-MS analysis of the digest of commercial Reference Standard Batch anti2C4907-2 yielded all of the expected disulfide-linked peptide-pairs (Table 2).

TABLE 2

Disulfide-Linked Peptide-Pairs Identified by LC-MS

| Expectecd[a] | Disulfide Linkage | Found | Expected Mass (Da)[b] | Observed Mass (Da)[b] |
|---|---|---|---|---|
| T2H = T10H | Cys22 = Cys96 | T2H = T10H | 3429.48 | 3429.48 |
| T13H = T14H | Cys146 = Cys202 | T13H = T14H | 7917.92 | 7917.92 |
| T19H = T19H | Cys228 = Cys228 Cys231 = Cys231[c] | T19H = T19H | 5455.78 | 5455.79 |
| T21H = T27H | Cys263 = Cys323 | T21H = T27H | 2329.10 | 2329.10 |
| T35H = T40H | Cys369 = Cys427 | T35H = T40H | 3845.82 | 3845.82 |
| T18H = T20L | Cys222 = Cys214 | T18H = T20L | 757.24 | 757.24 |
| T18H = T20L | Cys222 = Cys214 | T18H = T19L-T20L[d] | 1261.49 | 1261.49 |

TABLE 2-continued

Disulfide-Linked Peptide-Pairs Identified by LC-MS

| Expectecd[a] | Disulfide Linkage | Found | Expected Mass (Da)[b] | Observed Mass (Da)[b] |
|---|---|---|---|---|
| T2L = T7L | Cys23 = Cys88 | T2L = T7L | 5393.48 | 5393.48 |
| T11L = T18L | Cys134 = Cys194 | T11L = T18L | 3556.75 | 3556.75 |

Note:
An equal sign (=) represents a disulfide bond.
H = heavy chain; L = light chain; LC-MS = high-performance liquid chromatography mass spectrometry; T = tryptic peptide.
[a]Refer to FIGS. 9 and 10.
[b]Monoisotopic masses (MH[+]).
[c]Disulfides are inferred. The T19H dimer assignment did not include verification of Cys228 = Cys228 and Cys231 = Cys231 disulfides.
[d]The presence of this disulfide-linked pair has been confirmed through the use of an alternate enzyme, Lys-C, that does not cleave T19L and T20L.

Figure 8:
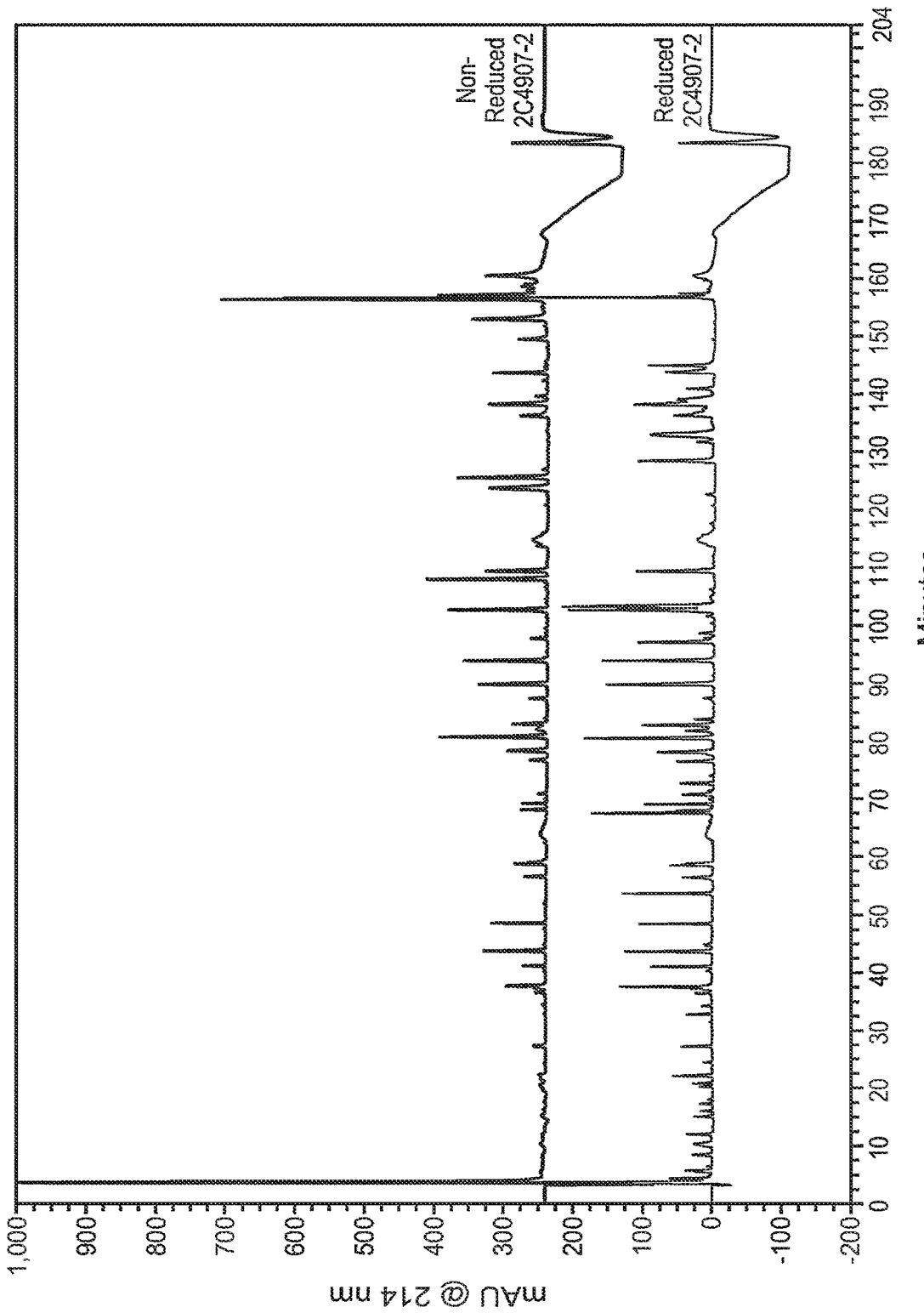
FIG. 8 depicts tryptic peptide maps of reduced and non-reduced Pertuzumab (full scale).
Figure 9:
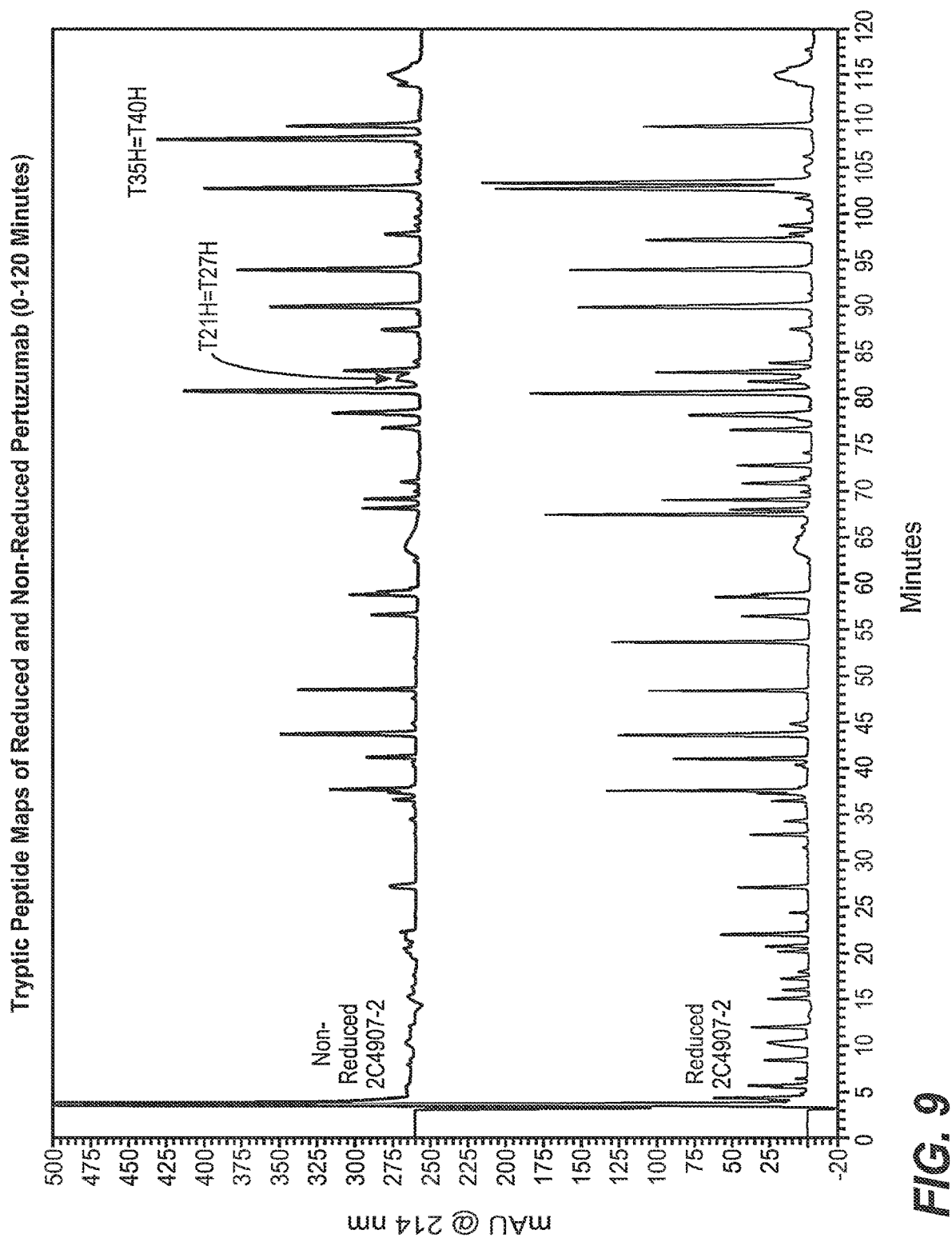
FIG. 9 depicts tryptic peptide maps of reduced and non-reduced Pertuzumab (0-120 minutes).
Figure 10:
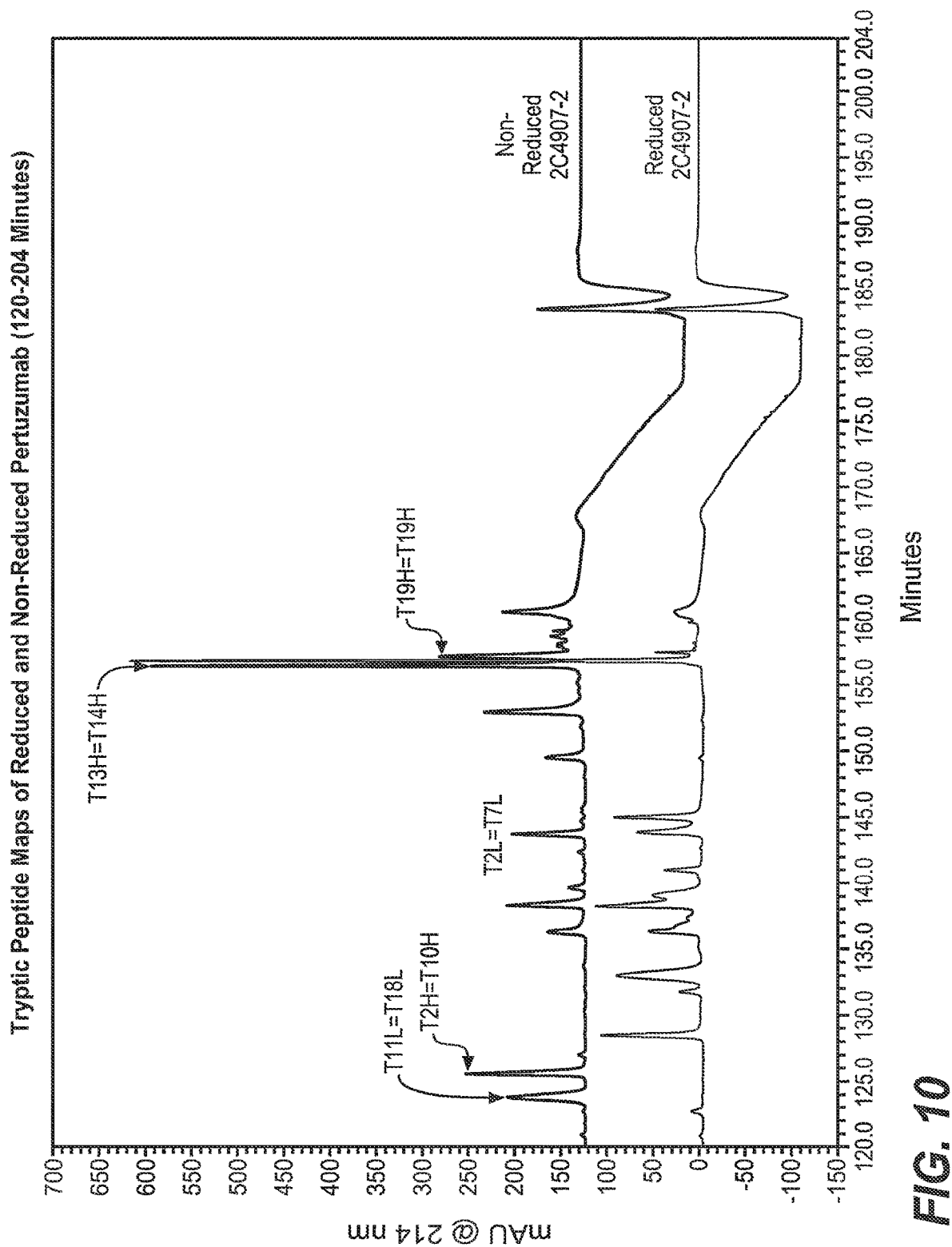
FIG. 10 depicts tryptic peptide maps of reduced and non-reduced Pertuzumab (120-204 minutes).

Identified peptides were further confirmed by the identification of expected peptides from the peptide-pairs upon reduction of the disulfides (FIG. 8 with expanded views in FIGS. 9 and 10). A dimer of heavy-chain peptide T19H (T19H=T19H) was identified as containing two disulfide bonds; identification of the Cys228=Cys228 and Cys231=Cys231 pairs is inferred. One disulfide pair, T18H=T20L, was detected by LC-MS but eluted close to the void volume and was not identifiable as a distinct peak on ultraviolet (UV) chromatograms. The presence of this disulfide pair was further confirmed by LC-MS analysis of a Lys-C digest, wherein the peptide T18H=T19L-T20L was observed. No unexpected linkages were found. One disulfide bond is partially unpaired, as discussed below.

Free Sulfhydryl Analysis: All cysteine residues in properly folded pertuzumab should be involved in disulfide bonds. Ellman's assay (Ellman, G. *Arch. Biochem. Biophys.* 82: 70-77 (1959)), a method for measuring the free sulfhydryl content of peptides and proteins, was used to determine if reactive unmodified (free) thiols are present in pertuzumab. All materials were evaluated for free thiol (unpaired cysteine residue) content and results are summarized in Table 3.

TABLE 3

Free Thiol Content by Ellman's Assay

| Batch Name | Moles of Free Thiols per Mole of Pertuzumab |
|---|---|
| anti2C4-900-1 | 0.06 |
| anti2C4907-2 | 0.15 |
| Run 1 | 0.28 |
| Run 3 | 0.16 |
| Run 4 | 0.17 |
| Run 5 | 0.16 |
| Run 6 | 0.16 |
| Run 7 | 0.14 |

Note:
Free thiol levels were determined by Ellman's assay in the presence of 8M urea.

Approximately 0.1-0.3 moles of free thiols per mole of pertuzumab were observed in all batches analyzed. In the absence of 8 M urea, free thiol levels were below the quantitation limit (QL; approximately 0.1 mole free thiol per mole protein) in all materials tested, indicating that the free thiols (i.e., unpaired cysteines) present in pertuzumab molecules were buried and inaccessible to Ellman's reagent under non-denaturing condition.

Figure 11:
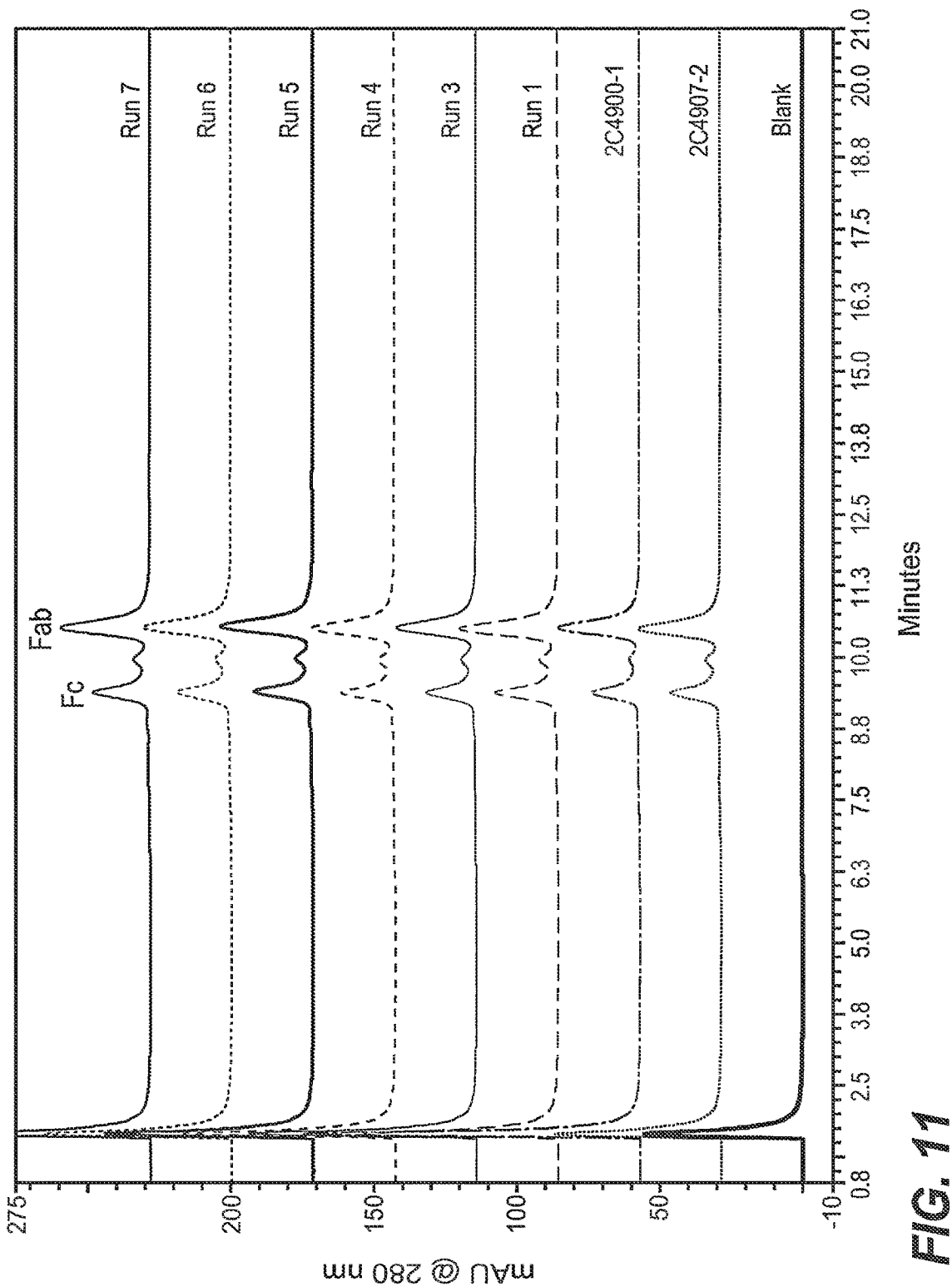
FIG. 11 depicts hydrophobic interaction chromatography (HIC) analysis of papain-digested Pertuzumab.
Figure 12:
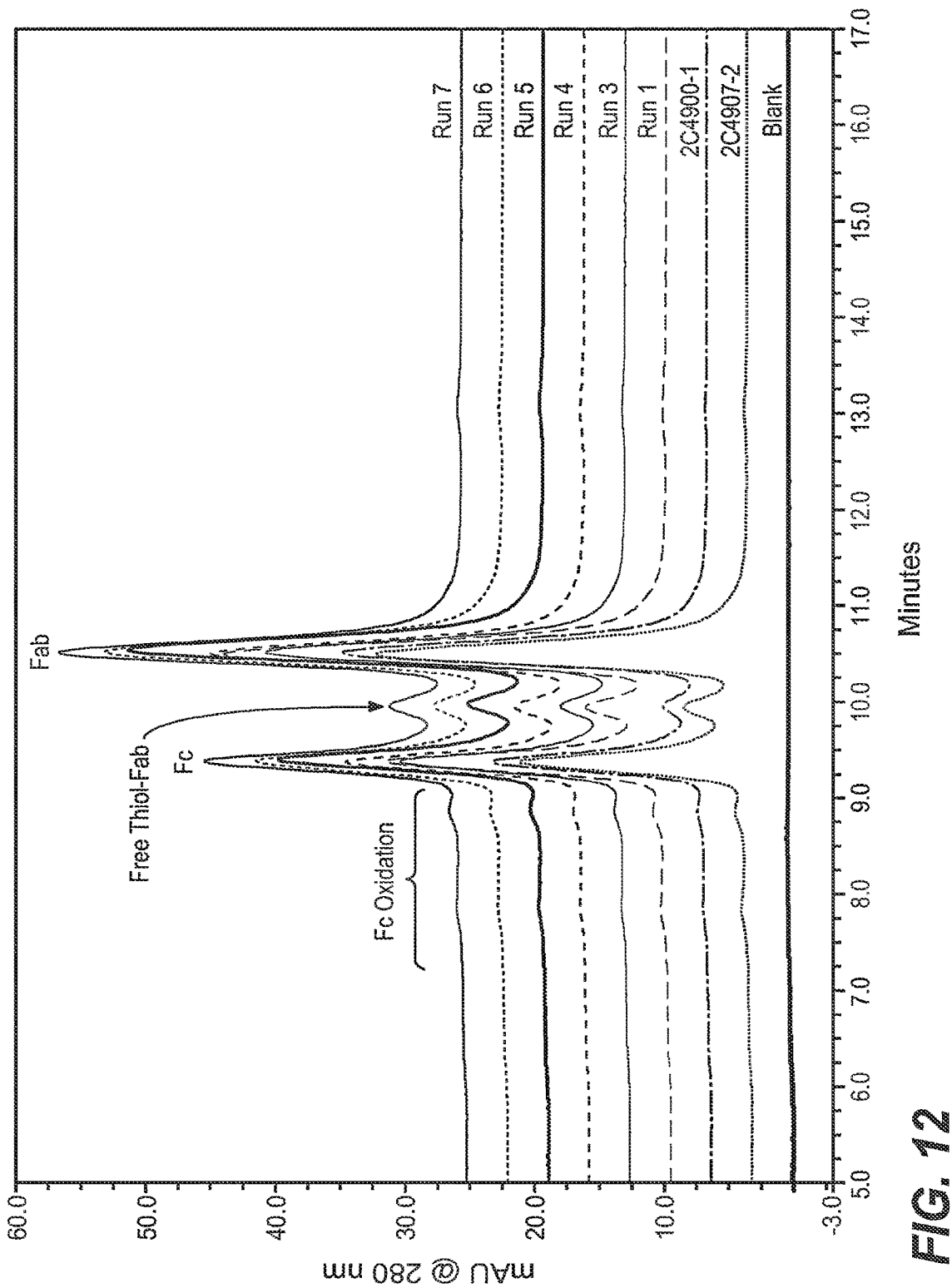
FIG. 12 depicts HIC analysis of papain-digested Pertuzumab (expanded view).

Analysis of pertuzumab materials by HIC after CpB and papain digestion revealed an additional peak between the Fc and Fab peaks which was identified as a Fab variant containing unpaired cysteine residues at Cys23 and Cys88 (FIGS. 11 and 12, labeled as free thiol Fab). This identification was confirmed by LC-MS tryptic peptide mapping, wherein the sample was subjected to denaturation in the presence of NEM prior to reduction and tryptic digestion. The extent of the free thiol Fab variant using the papain HIC method was measured across pertuzumab batches and found to be consistent using the current process (Table 4).

TABLE 4

Relative Amount of Cys23/Cys88 Unpaired Cysteine Fab Variant as Determined by Papain HIC or Calculated Intact Antibody Variant

| Batch Name | Percent Unpaired Cysteine Fab Variant | Percent Intact Antibody Variant* |
|---|---|---|
| anti2C4-900-1 | 9.4 | 17.9 |
| anti2C4907-2 | 12.7 | 23.8 |
| Run 1 | 13.2 | 24.6 |
| Run 3 | 13.3 | 24.9 |
| Run 4 | 13.5 | 25.2 |
| Run 5 | 13.3 | 24.9 |
| Run 6 | 12.9 | 24.2 |
| Run 7 | 13.2 | 24.6 |

Note:
The percent unpaired cysteine Fab peak was obtained by dividing the unpaired cysteine Fab peak area by the peak areas of unpaired cysteine Fab + Fab.
*Calculated as described below.

By the papain HIC assay, the values for material produced using the commercial process ranged from 12.7% to 13.5%, while the value for Reference Standard Batch 2C4-900-1 (Phase I/II) was slightly lower at 9.4%.

Converting % Fab Variant from Papain HIC to Estimated % Intact Antibody Variant: The relative amount of Fab fragments containing unpaired cysteines can be used to calculate the relative distribution of heterodimer or homodimer forms of unpaired cyceteine varints. If papain HIC assay shows that 10% (or x %) of Fab fragments from pertuzumab contain unpair cycteines at Cys23/Cys88, then there should be 10 Fab fragments containing unpaired cysteines released from every 50 pertuzumab molecules because the digestion of 50 antibodies by papain should yield 100 Fab fragments. Assuming that these 10 Fab fragments are from 10 different pertuzumab molecules, the relative amount pertuzumab containing one Fab with Cys23/Cys88 unpaired cysteines is approximately 20%, i.e. 10 out 50 pertuzumab molecules, (or 2x %). More precisely, if the probability of a pertuzumab with two Fabs containing Cys23/Cys88 unparied cysteines is taken into account, then the relative amount of pertuzumab heterodimer unpaired cysteine variants should be 2×10%×90%=18% (or 2×x %×[100-x] %). In addition, the relative amount of pertuzumab homodimer unpaired cysteine variants should be at 10%×10%=1% (or x %×x %). In this case, the relative among of pertuzumab containing 2 Fabs with no unpaired cysteines on either Fab should be at 90%×90%=81% (or [100-x]%×[100-x]%).

Figure 13:
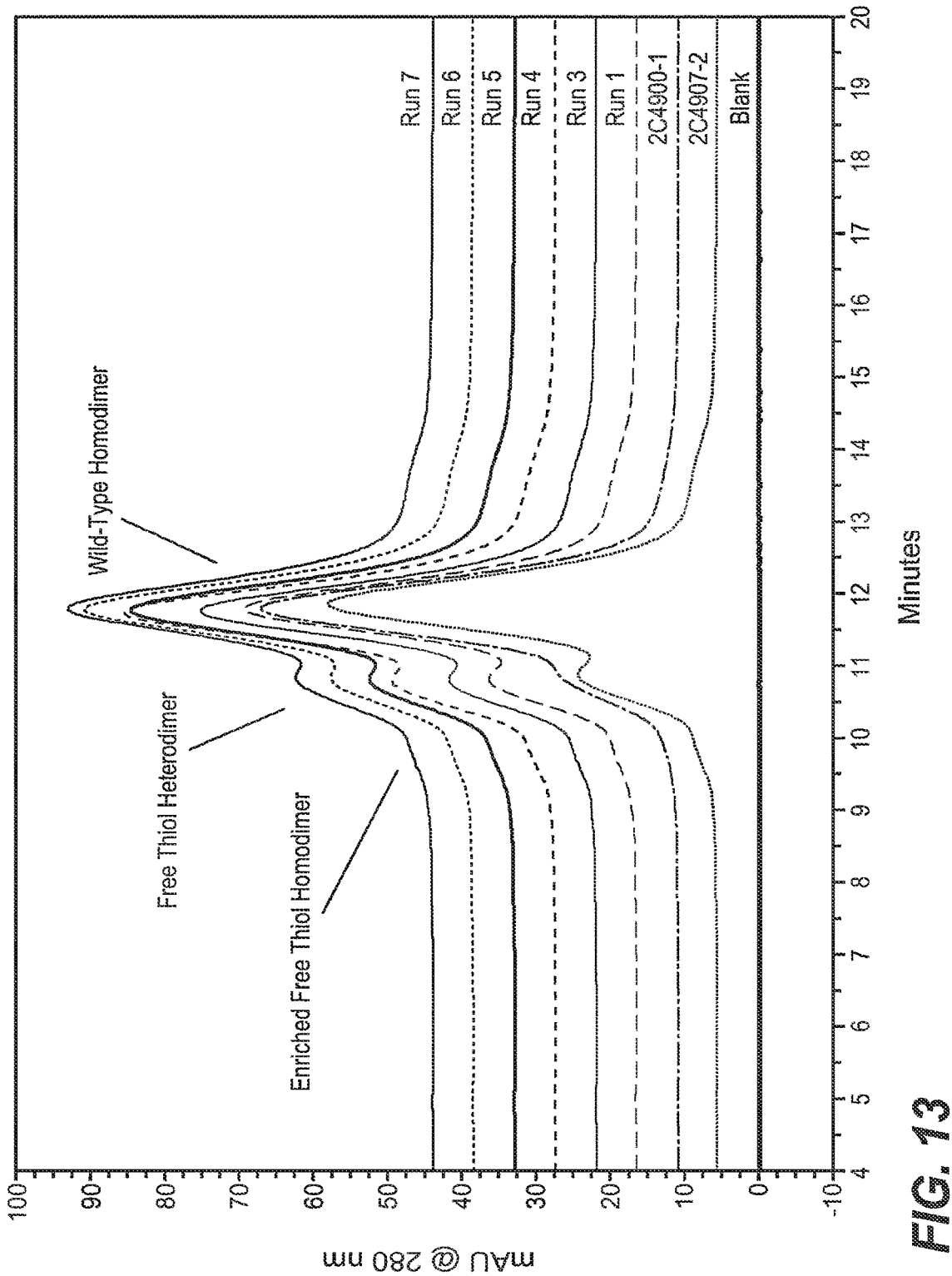
FIG. 13 depicts HIC analysis of intact Pertuzumab. Peaks comprising: enriched free thiol homodimer (free thiols on both light chains), free thiol heterodimer (free thiol on one light chain), and wild-type homodimer (main species antibody) are shown.

In addition wild-type homodimer (without unpaired cysteines) and heterodimer (with unpaired cysteines on one Fab) can be quantified directly by HIC. HIC of intact antibody separates pertuzumab into two major peaks (FIG. 13), which were identified as wild type homodimer (without free thiols) and heterodimer (with free thiol pair on one Fab) by LC-MS tryptic peptide mapping. The minor front shoulder peak was also collected and characterized by papain HIC as predominantly homodimer (free thiol pair on both Fabs, approximately 40%) and pertuzumab with Fc oxidation. Using the HIC of intact antibody, pertuzumab was estimated to contain approximately 17%-18% heterodimer for materials produced using the current process, and 13% using the Phase I/II process (Table 5). Without being bound by any one theory, it is possible that the increased amount of the unpaired cysteine variant produced by the commercial process (relative to the phase I/II process) may result from protein (i.e. VL domain) folding rate accuring faster than thiol oxidation (disulfide formation) rate, thus trapping free cysteines in the variant.

TABLE 5

Relative Amount of Intact Unpaired Cysteine Variants as Determined by HIC of Intact Pertuzumab

| | Peak | | |
|---|---|---|---|
| Batch Name | Wild-Type Homodimer (%) | Unpaired cysteine Heterodimer (%) | Partially Enriched Unpaired cysteine Homodimer (%) |
| anti2C4-900-1 | 84.7 | 13.4 | 1.9 |
| anti2C4907-2 | 78.9 | 18.2 | 2.9 |
| Run 1 | 78.4 | 18.4 | 3.2 |
| Run 3 | 79.1 | 17.6 | 3.2 |
| Run 4 | 79.3 | 17.3 | 3.4 |
| Run 5 | 79.1 | 17.4 | 3.5 |
| Run 6 | 79.7 | 17.2 | 3.1 |
| Run 7 | 79.3 | 17.3 | 3.4 |

Note:
The percent relative peak was obtained by dividing the individual peak area by the total peak area of all three peaks.

Since an unpaired cysteine pair at Cys23/Cys88 on the light chain of pertuzumab was observed by HIC, purified fractions of each of the unpaired cysteine variants were tested in the anti-proliferation assay. The unpaired cysteine containing Fab was purified and estimated to have reduced potency (estimated potency ~50% relative to the native Fab) (Table 6).

TABLE 6

Anti-Proliferation of Unpaired Cysteine Fab Variant

| Pertuzumab Samples and Conditions | Mean % Activity (n = 2) | % Difference |
|---|---|---|
| Native Fab | 100 | N/A |
| Unpaired Cysteine-Fab | 50[a] | 67 |

Note:
Percent activity reported relative to Native Fab.
[a]Estimated potency value. Dose response curves are not parallel, and the lower plateau does not converge.

In addition, three intact forms (wild-type homodimer, free-thiol containing heterodimer, and unpaired cysteine containing homodimer) were isolated by HIC and tested with the anti-proliferation potency assay. See Table 7.

TABLE 7

Anti-Proliferation Activities of Full Length Pertuzumab Unpaired Cysteine Variants Fractions

| | Anti-proliferation | |
|---|---|---|
| Pertuzumab Samples and Conditions | Mean % Activity (n = 3) | CV (%) |
| Starting Material | 110 | 11 |
| Heterodimer | 112 | 7 |

TABLE 7-continued

Anti-Proliferation Activities of Full Length Pertuzumab Unpaired Cysteine Variants Fractions

| | Anti-proliferation | |
|---|---|---|
| Pertuzumab Samples and Conditions | Mean % Activity (n = 3) | CV (%) |
| Wild-Type Homodimer | 104 | 15 |
| Unpaired cysteine-Containing Homodimer[a] | 90 | 15 |

Note:
Percent activity reported relative to pertuzumab Reference Standard (Batch anti2C4907-2).
[a]The fraction contains approximately 40% unpaired cysteine-containing homodimer and 60% heterodimer or wild-type homodimer mixture.

These data demonstrate that an unpaired cysteine variant of pertuzumab is present in the composition manufactured at commercial scale. The HIC methods (evaluating Fab fragment or intact antibody) in this Example or peptide mapping in Example 3 below are assays that can be used to evaluate the presence and quantity of the unpaired cysteine variant in a pertuzumab composition.

Example 2

Afucosylated Pertuzumab Composition and Characterization Thereof

Figure 14:
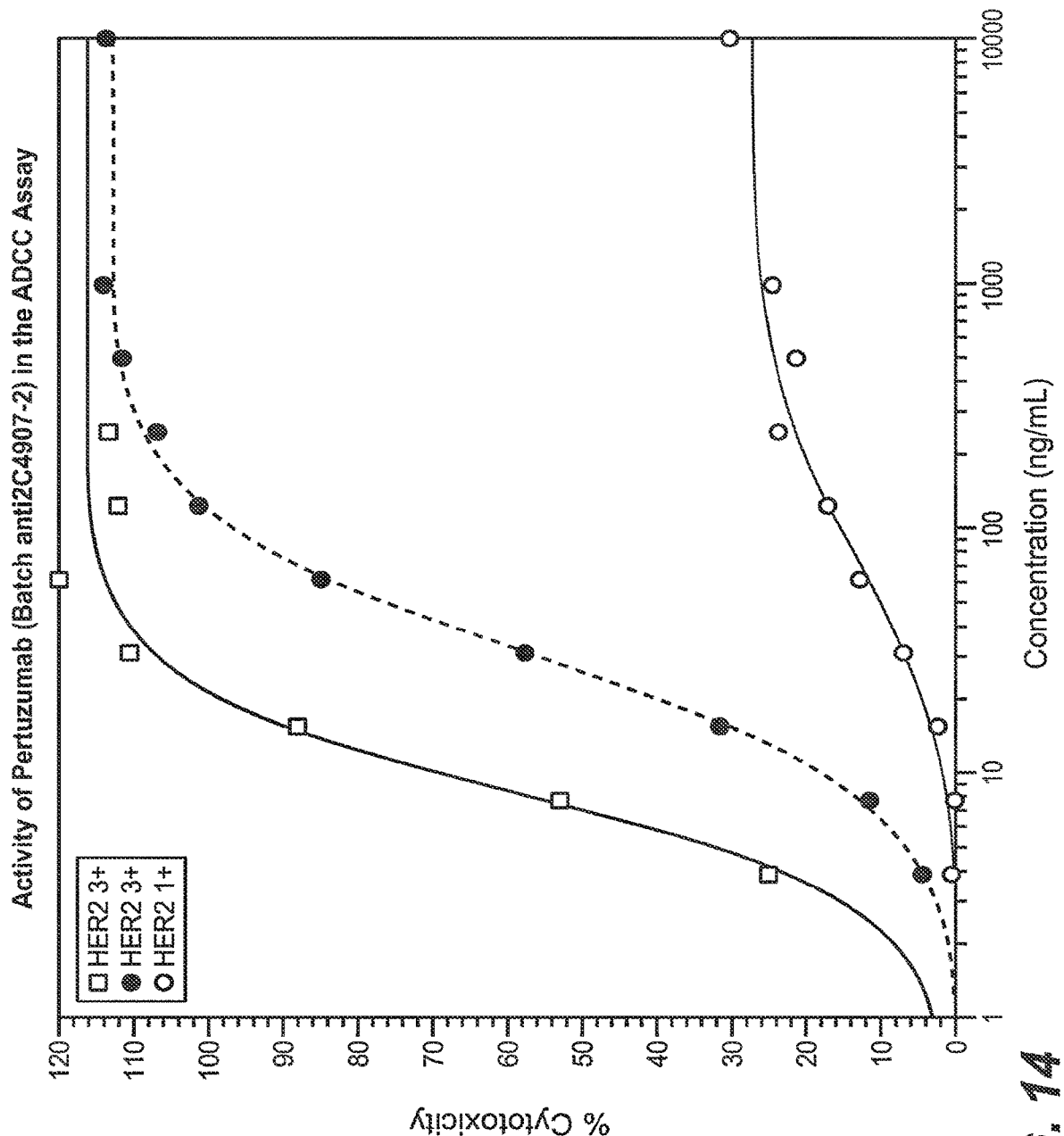
FIG. 14 depicts activity of Pertuzumab (Batch anti2C4907-2) in the antibody-dependent cell-mediated cytotoxicity (ADCC) assay.

Antibody-Dependent Cell-Mediated Cytotoxicity (ADCC) is an aspect of cell-mediated immunity by which an effector cell actively lyses a target cell that has bound antigen-specific antibodies. Pertuzumab exhibited ADCC activity when tested with HER2 3+ cells but very little activity was observed with HER2 1+ cells (FIG. 14).

Figure 15:
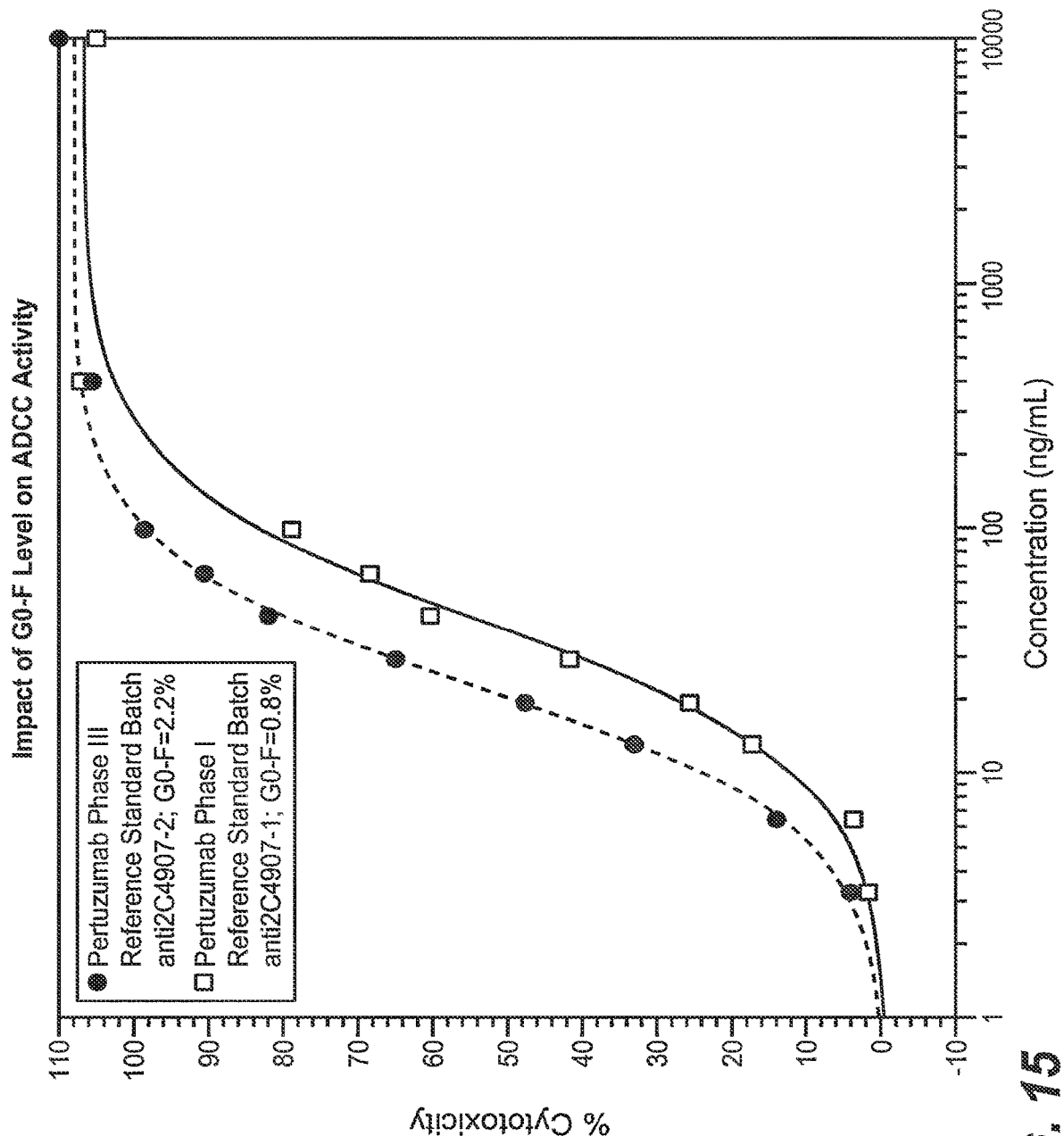
FIG. 15 depicts impact of G0-F level on ADCC activity. Samples tested were phase III Pertuzumab (G0-F=2.2%) and phase I Pertuzumab (G0-F=0.8%).

The levels of afucosylation in the pertuzumab Phase I and Phase III Reference Standards were measured using capillary electrophoresis. The higher level of afucosylated material (G0-F=2.2%) in the pertuzumab Phase III Reference Standard correlates with the higher ADCC activity observed compared to Phase I Reference Standard (FIG. 15), which had lower G0-F (0.8%). An enzymatically deglycosylated pertuzumab was also prepared and tested and showed no binding to FcγRIIIa and no ADCC activity (Table 8).

TABLE 8

Biological Activities of Deglycosylated Pertuzumab

| Pertuzumab Samples and Conditions | Mean % Activity (n = 3) | | | | |
|---|---|---|---|---|---|
| | Anti-Proliferation | HER2 Binding | FcγRIIIa Binding | ADCC | FcRn Binding |
| Control | 90 | 105 | 106 | 101 | 85 |
| Deglycosylated | 87 | 94 | No Activity | No Activity | 72 |

Note:
Percent activity reported relative to pertuzumab Reference Standard (Batch anti2C4907-2).
ADCC = antibody-dependent cell-mediated cytotoxicity.

These data show that measuring G0-F (afucosylated) pertuzumab is an effective means for quantifying pertuzumab's ADCC activity. Experiments to quantify afucosylation are as follows.

Oligosaccharide Analysis by Capillary Electrophoresis (CE): Pertuzumab samples (250-500 µg) were purified using Protein A solid phase extraction affinity tips (PHYTIPS™) and an automated liquid handling system. Pertuzumab samples were eluted from the protein A resin using 12 mM hydrochloric acid, pH 2.0 and neutralized using 10 µL of 50 mM sodium succinate. The resulting sample was incubated with 2.5 U/mL of PNGase F for 15 hours at 37° C. The protein was precipitated by heating the solution at 95° C. for 5 minutes and was removed by centrifugation. The supernatant solutions containing released oligosaccharides were vacuum dried. The released glycans were derivatized with 8-aminopyrene-1,2,6-trisulfonic acid (APTS) in a 15% acetic acid solution containing sodium cyanoborohydride at 55° C. for two hours. Analyses of derivatized glycans were performed with a capillary electrophoresis (CE) system equipped with a fluorescence detection module using an argon-ion laser (488 nm excitation, 520 nm emission) and an N—CHO coated capillary (50 μm×50 cm). The running buffer was 40 mM c-amino-n-caproic acid/acetic acid, pH 4.5, 0.2% hydroxypropyl methylcellulose (HPMC). Samples were injected into the capillary by pressure at 0.5 psi. The separation was performed at 20 kV, and the capillary temperature was maintained at 20° C.

Pertuzumab contains an N-linked oligosaccharide site in the $C_H2$ domain of the Fc portion of the molecule at Asn299. The relative distribution of the neutral oligosaccharides found at this site for each batch was determined using CE after treatment with PNGase F and labeling with APTS.

Figure 16:
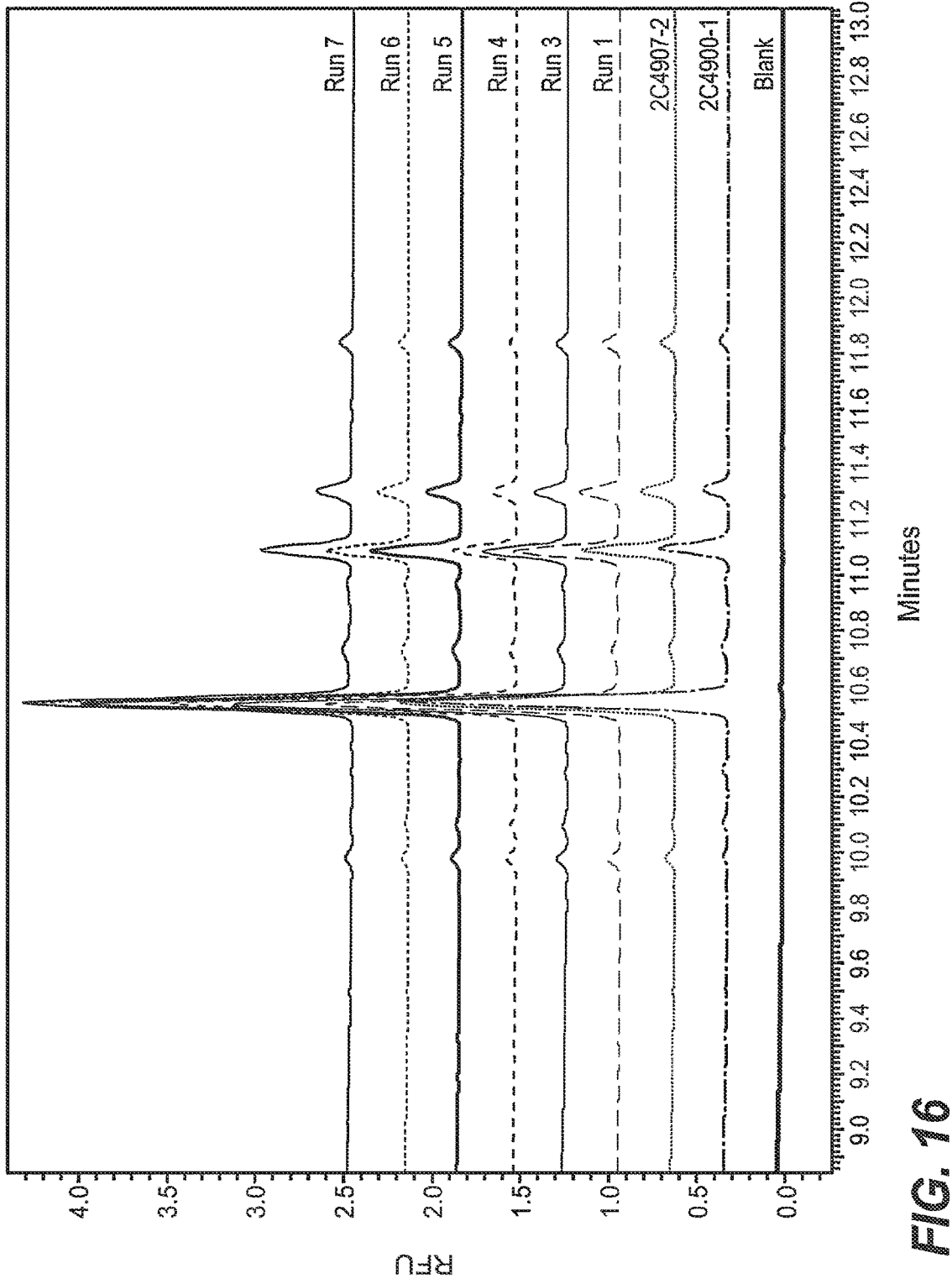
FIG. 16 depicts capillary electrophoresis analysis of N-linked oligosaccharides released from Pertuzumab.
Figure 17:
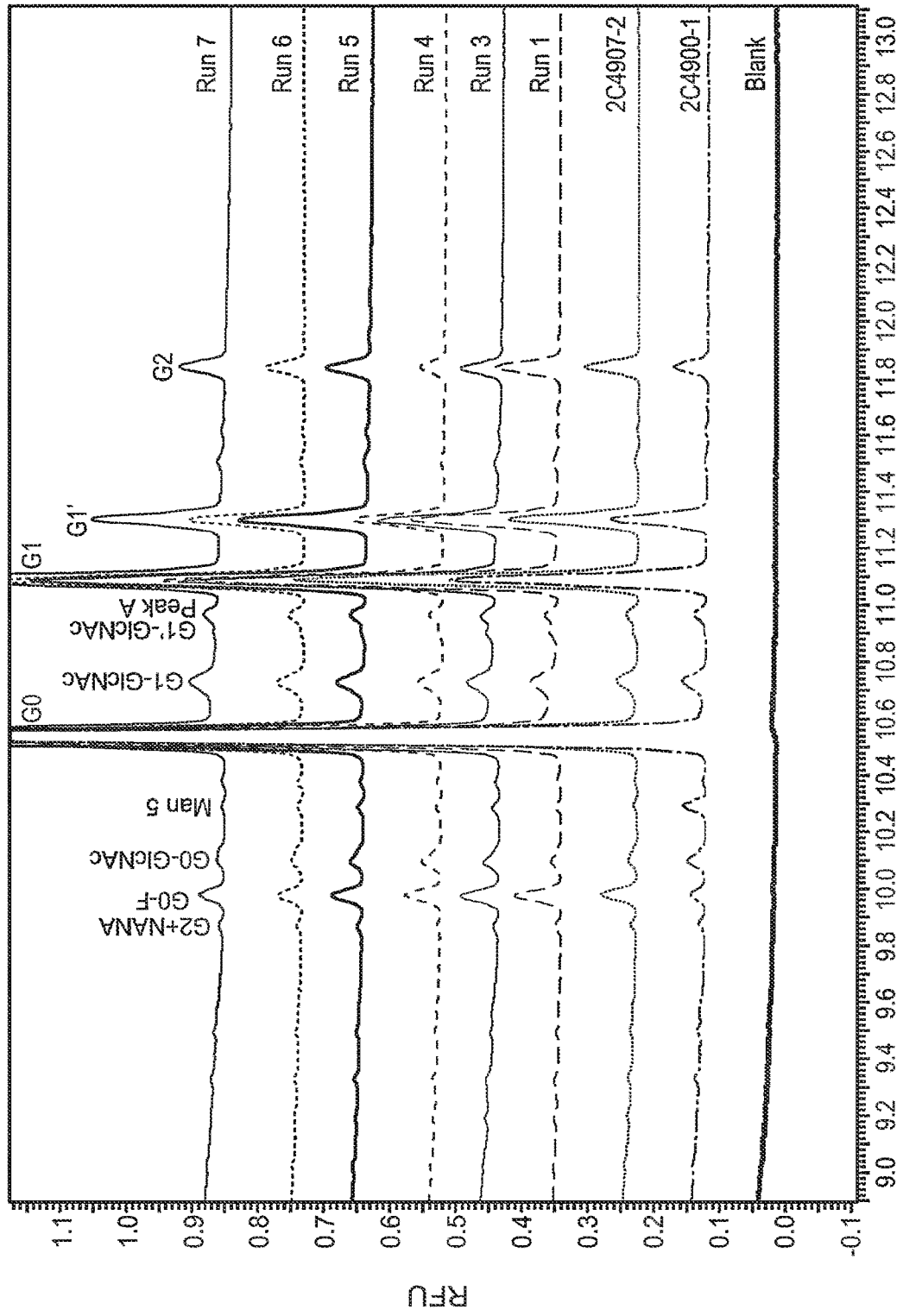
FIG. 17 depicts capillary electrophoresis analysis of N-linked oligosaccharides released from Pertuzumab (expanded view). Note: The G1 oligosaccharide has two isomeric forms (labeled G1 and G1') wherein the terminal galactose residue is attached to either the α1-6 branch or the α1-3 branch.

The electropherograms from CE analysis of the released, derivatized oligosaccharides are shown in FIG. 16 with expanded-view profiles in FIG. 17. Relative amounts of oligosaccharides in pertuzumab for the materials analyzed are summarized in Table 9.

TABLE 9

Distribution of Oligosaccharide Structures in Pertuzumab (Percent Peak Area)

| Batch Name | G0-F | G0-GlcNAc | Man5 | G0 | G1$^a$ | G2 |
|---|---|---|---|---|---|---|
| anti2C4-900-1 | 0.8 | 2.7 | 1.2 | 72.1 | 20.4 | 2.0 |
| anti2C4907-2 | 2.2 | 0.8 | 0.3 | 63.6 | 27.6 | 3.0 |
| Run 1 | 2.5 | 1.6 | 0.2 | 62.4 | 29.1 | 3.4 |
| Run 3 | 1.7 | 1.2 | 0.3 | 70.3 | 23.4 | 2.2 |
| Run 4 | 1.8 | 1.8 | 0.3 | 75.4 | 18.3 | 1.4 |
| Run 5 | 1.4 | 1.0 | 0.4 | 71.8 | 22.4 | 2.1 |
| Run 6 | 1.1 | 1.0 | 0.2 | 73.3 | 21.3 | 1.9 |
| Run 7 | 1.2 | 0.8 | 0.2 | 69.7 | 24.5 | 2.5 |

Note:
The total % may not add exactly to 100% due to rounding. In addition, minor species (<0.5%) may have been included in the total percent peak area but not reported in this table.
$^a$Sum of the two G1 isomers (refer to FIG. 17).

The oligosaccharide with G0 structure is the predominant species in all materials (62%-75%). The G0 glycoform was slightly more abundant in Runs 3-7 and the previous Reference Standard Batch 2C4-900-1 (70%-75%) compared to the current Reference Standard Batch anti2C4907-2 and Run 1 (62%-64%). The G1 glycoform was observed as two peaks corresponding to the two isomers with the terminal galactose on either branch of the biantennary structure. The areas of these two peaks were combined in order to determine the relative amount of G1 glycoform. The G1 and G2 glycoforms account for approximately 18%-29% and 1%-3%, respectively of the released oligosaccharides for all the materials. Peaks arising from other oligosaccharide structures were also observed in the electropherograms (all present at 3% or less). These structures include G0-F (G0 lacking core fucose), G0-GlcNAc (G0 lacking one GlcNAc), Man5, and other minor glycoforms (Ma and Nashabeh *Anal Chem* 71:5185-92 (1999)). Oligosaccharide structures on pertuzumab were consistent with those found CHO—derived MAbs (Ma and Nashabeh, supra) and naturally occurring human immunoglobulins (Flynn et al. *Mol Immunol* 47:2074-82 (2010)).

Example 3

Peptide Mapping and RP-HPLC for Evaluating Unpaired Cysteine Variant

Materials: Materials and devices used in the experiments include: 3-[N-Morpholino]propanesulfonic Acid (MOPS; Sigma-Aldrich), N-ethylmaleimide (d0-NEM; Thermo Scientific, Rockford, Il), N-ethylmaleimide (d5-NEM; Cambridge Isotope Laboratories, Andover, MA), L-Cysteine (Sigma-Aldrich), Trypsin (Promega, Madison, WI), Trifluoroacetic acid (TFA; Fisher, Fair Lawn, NJ), Acetonitrile (ACN, Burdick & Jackson, Muskegon, MI). All chemicals and reagents were used as received with no further purification.

Differential N-Ethylmaleimide (NEM) Labeling of Antibodies: Differential NEM tagging method allowed free thiols already present in the antibodies to be tagged with d0-NEM and remaining disulfide bridges to be reduced and tagged with d5-NEM. For initial d0-NEM tagging, 100 μL antibody (3 mg/mL) was gently mixed with 400 μL Denaturing Buffer (7.5 M GdnHCl, pH 5) containing 6.25 mM d0-NEM and incubated at 37° C. for 2 h. 20 μL Cysteine (125 mM) was added to the sample and incubated at 37° C. for 15 minutes to inactivate remaining d0-NEM. To reduce remaining disulfide bridges in the antibody, 10 μL TCEP (0.5 M) was added to the sample and incubated at 37° C. for 30 minutes. 70 μL d5-NEM (171 mM) was then added to the sample and incubated at 37° C. for 2 h to tag the free thiols created by the reduced disulfide bridges. 0.5 mL of the differential NEM tagged sample was buffer exchanged using NAP-5 columns and eluted with 0.6 mL MOPS buffer (20 mM MOPS, 0.5 mM TCEP, pH 7).

Peptide map analysis of Antibodies: Differential NEM tagged samples were digested with trypsin at a 1:50 (w/w) trypsin:antibody ratio at 37° C. for 2 h. Digestions were quenched with 10% TFA. The trypsin digested differential NEM tagged samples were separated using an Agilent 1200 HPLC system (Agilent, Palo Alto, CA). A Jupiter C18 column (250×2 mm, 5 μm) (Phenomenex, Torrance, CA) with 300 Å pore size was employed for chromatographic separation of samples. The injection volume was 95 μL, and the column temperature was 55° C. The mobile phase A was 0.1% TFA in water and mobile phase B was 0.08% TFA in 90% ACN (v/v). Initial conditions were set at 100% mobile phase A and kept for the first 3 minutes after sample injection. Mobile phase B was increased to 10% over the next 20 minutes and then further increased to 40% until 160 minutes and 100% until 162 minutes all over linear gradients. Mobile phase B was held at 100% until 170 minutes. The column was the re-equilibrated at 100% mobile phase A until 195 minutes. The flow rate was kept at 0.28 mL/min.

The effluent from the HPLC was directly connected to the electrospray ionization source of LTQ ORBITRAP™ mass spectrometer operating in a positive ion mode. The spray voltage was 4.5 kV, and the capillary temperature was 300° C. The mass spectrometer was operated in the data dependent fashion to switch automatically between MS and MS/MS modes. Survey full scan MS spectra were acquired from m/z 300 to m/z 2000 in the FT-Orbitrap with a resolution set for R=60,000 at m/z 400. The five most intense ions were fragmented in the linear ion trap using collision induced dissociation (CID) at normalized collisional energy of 35% with an activation time of 30 ms and isolation width of 2.5 m/z units. The dynamic exclusion (DE) function was enabled to reduce data redundancy and allow low-intensity ions to be selected for data dependent MS/MS scans. The dynamic exclusion parameters were as follows: a repeat duration of 30 seconds, an exclusion list size of 500, an exclusion duration of 90 seconds, a low exclusion mass width 0.76, a high exclusion mass width of 1.56, and a repeat count of 2. The data analyses were performed using XCALIBUR™ software.

The current Pertuzumab Reference Standard Batch anti2C4907-2 was analyzed using the method described above. It was found that 10.9% of the T2L peptides (produced by trpsin digestion and containing Cys23) and 8.3% of the T7L peptides (produced by trpsin digestion and containing Cys88) were tagged with d0-NEM. Because only unpaired cysteines were tagged with d0-NEM in this experiment, these results suggest that approximately 10% of the Cys23 and Cys88 in anti2C4907-2 are not linked by a disulfide bond (i.e. 10% unpaired cysteins variants). Using a calculation method similar to that described above to convert the percent unpaired cysteine Fab variant into percent unpaired cysteine intact variant, it was estimated that 18% of the pertuzumab molecules in anti2C4907-2 are heterodimer unpaired cysteine variants, 1% of the pertuzumab molecules are homodimer unpaired cysteine variants, and 81% are the wild-type homodimer form (without unpaired cysteines). These results are in a general agreement with the results from HIC analysis of either the Fab fragments or the intact pertuzumab.

Limited Endoproteinase Lys-C Digestion to Generate the Fab: The Fab fragment of MAb A was generated through limited Lys-C digestion procedure. Briefly, MAb A (1 mg/ml) was mixed with Lys-C enzyme at 1:400 ratio in 100 mM Tris, pH 7.6, and then the mixture was incubated at 37° C. for 30 minutes. The reaction mixture was tagged with NEMin pH 5.5, 350 mM sodium acetate and 8M Guanidine HCl. The digests were analyzed with an RP-HPLC method described below.

RP-HPLC Conditions: RP-HPLC analysis was performed on an AGILENT 1200™ HPLC system (Palo Alto, CA, USA) equipped with a binary gradient pump, autosampler, temperature-controlled column compartment, and a diode array detector. The system included a Pursuit 3 diphenyl reversed phase column (150×4.6 mm, 3 µm, Varian, Lake Forest, CA, USA) that was run at 75° C. and 1 ml/min. The separation was monitored using absorbance at 280 nm. The mobile phase consisted of 0.1% TFA in water (mobile phase A) and 0.09% TFA in ACN (mobile phase B). The 38-minute method began with a three minute gradient from 32% to 36% mobile phase B, followed by an 18 minute linear gradient to 42% mobile phase B. The column was washed at 95% mobile phase B for 5 minute and equilibrated at 32% mobile phase B for 10 minutes.

Figure 18:
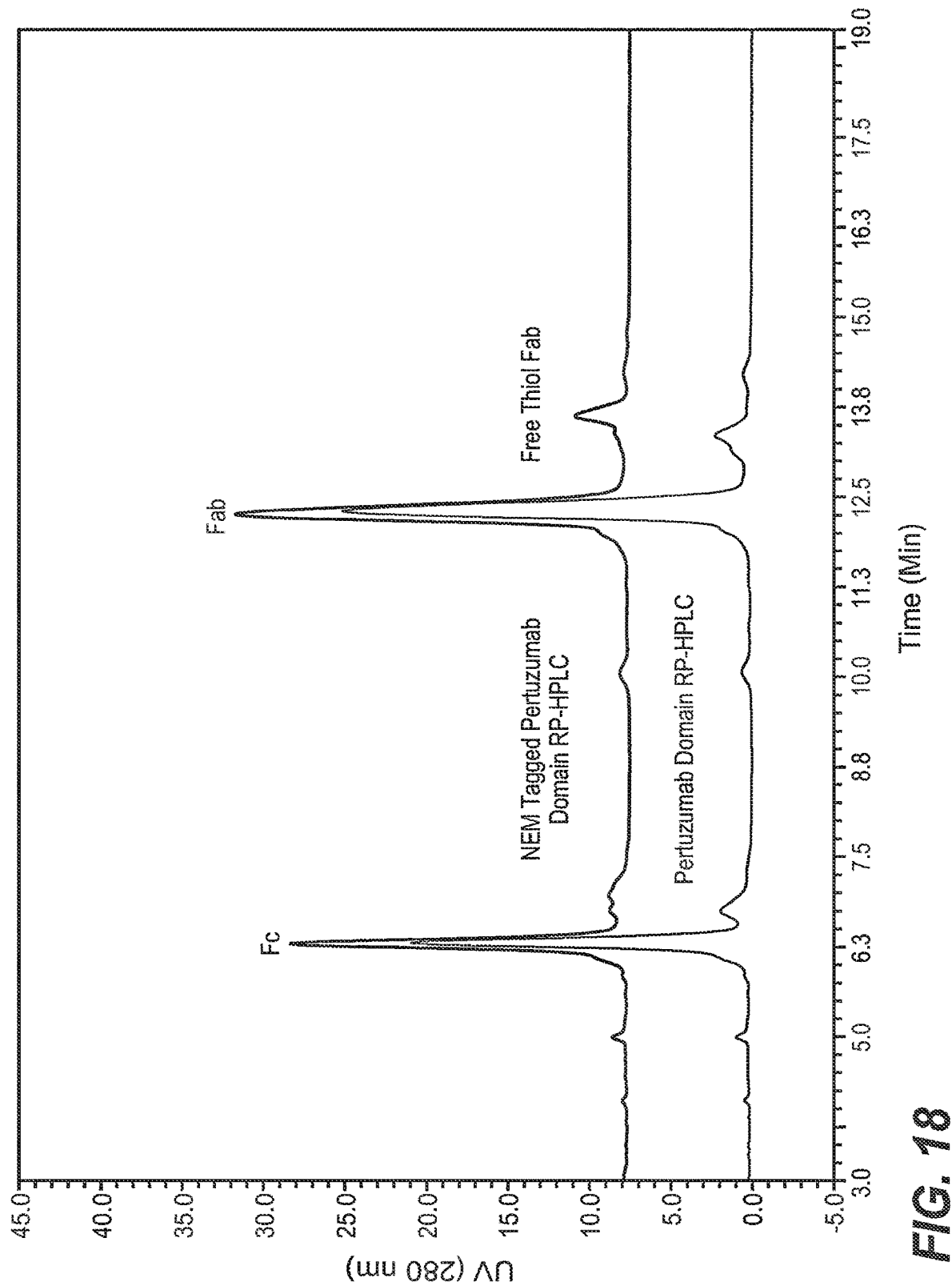
FIG. 18 depicts Reversed Phase-High Performance Liquid Chromatography (HP-HPLC) for Pertuzumab Fab and Fc (limited Lys-C digestion) separation. Limited Lys-C digested Pertuzumab and limited Lys-C digested Pertuzumab then treated with N-ethymaleimide (NEM) are shown.
Figure 19:
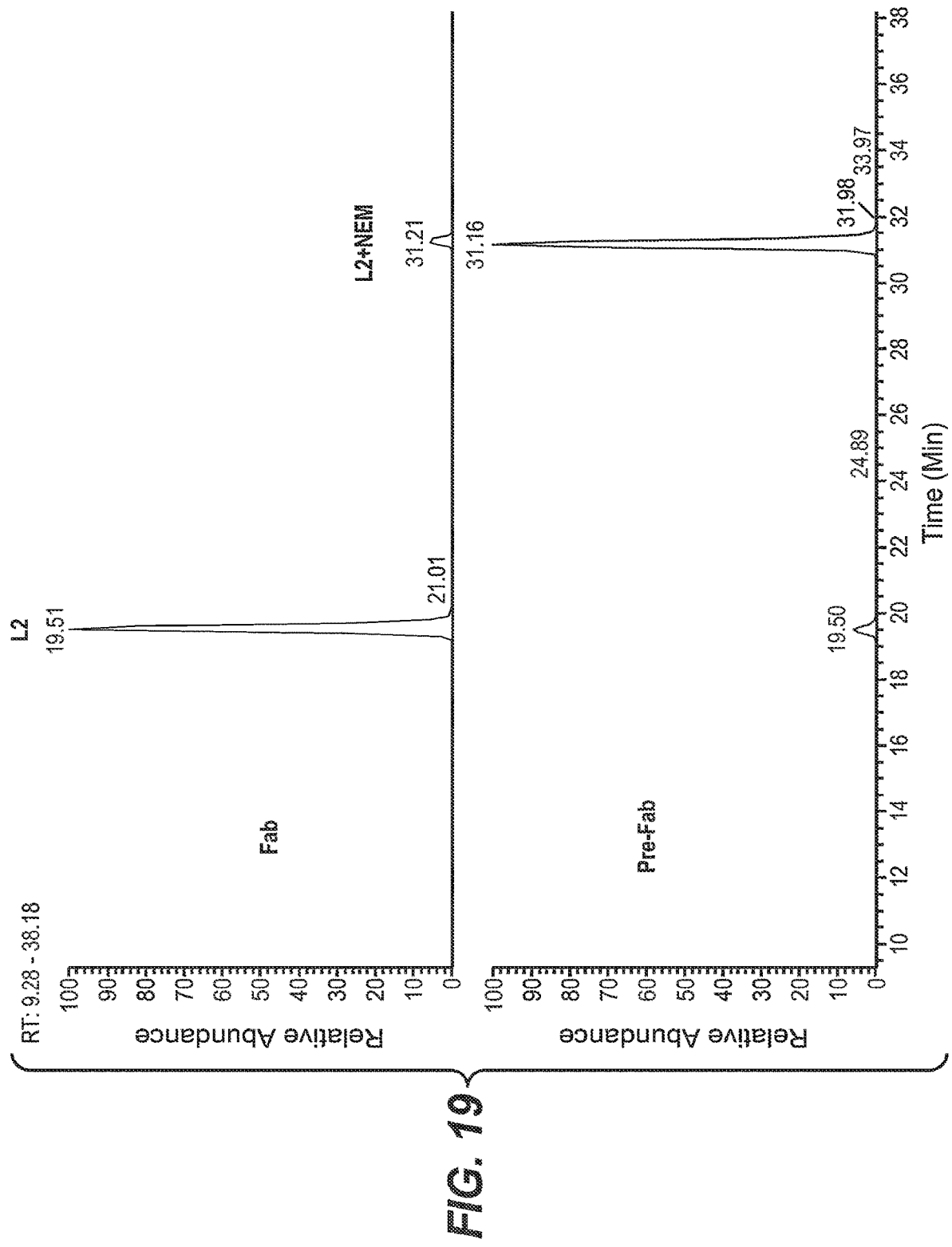
FIG. 19 depicts peptide mapping confirming Pertuzumab free thiol Fab contains free Cys23 and Cys88 at the light chain thereof. L2 peptide from the Fab containing free thiols was labeled by NEM and thus shifted in the peptide map analysis.

RP-HPLC analysis of free thiol Fab generated by limited Lys-C digestion (FIG. 18) indicated the free thiol Fab is around 13%, consistent with the HIC in Example 1. The NEM tagged free thiol Fab becomes more hydrophobic, thus eluted later compared with free thiol Fab (FIG. 18) and further confirmed the presence of free thiol. See also FIG. 19 in which peptide mapping confirms free thiol Example 4

Afucosylation Quantification by CE-LIF

This example describes a fully validated capillary electrophoresis-laser-induced fluorescence (CE-LIF) assay for quantifying afucosylated Pertuzumab variant. Modifications to the methods disclosed in Example 2 above include: no robotic sample preparation, no Protein A purification step ensuring consistent protein concentrations among samples, and changes to the electrophoretic parameters (buffer excipient concentration).

In the assay, Pertuzumab samples are diluted to 10 mg/mL using formulation buffer, and buffer exchanged into Peptide-N-Glycanase F (PNGase F) digest buffer. The asparagine-linked oligosaccharides are then released enzymatically with PNGase F. The released glycans are subsequently derivatized with 8-aminopyrene-1,3,6-trisulfonic acid (APTS), a negatively charged fluorophore. APTS provides all glycans with three negative charges, which allow their rapid electrophoretic analysis. The mixture containing the excess derivatizing agent and the APTS-glycan conjugates is analyzed by CE using a coated capillary that reduces the electroosmotic flow. The separation is monitored with a laser-induced fluorescence system using an argon-ion laser with an excitation wavelength of 488 nm and an emission band pass filter of 520 nm.

Figure 21:
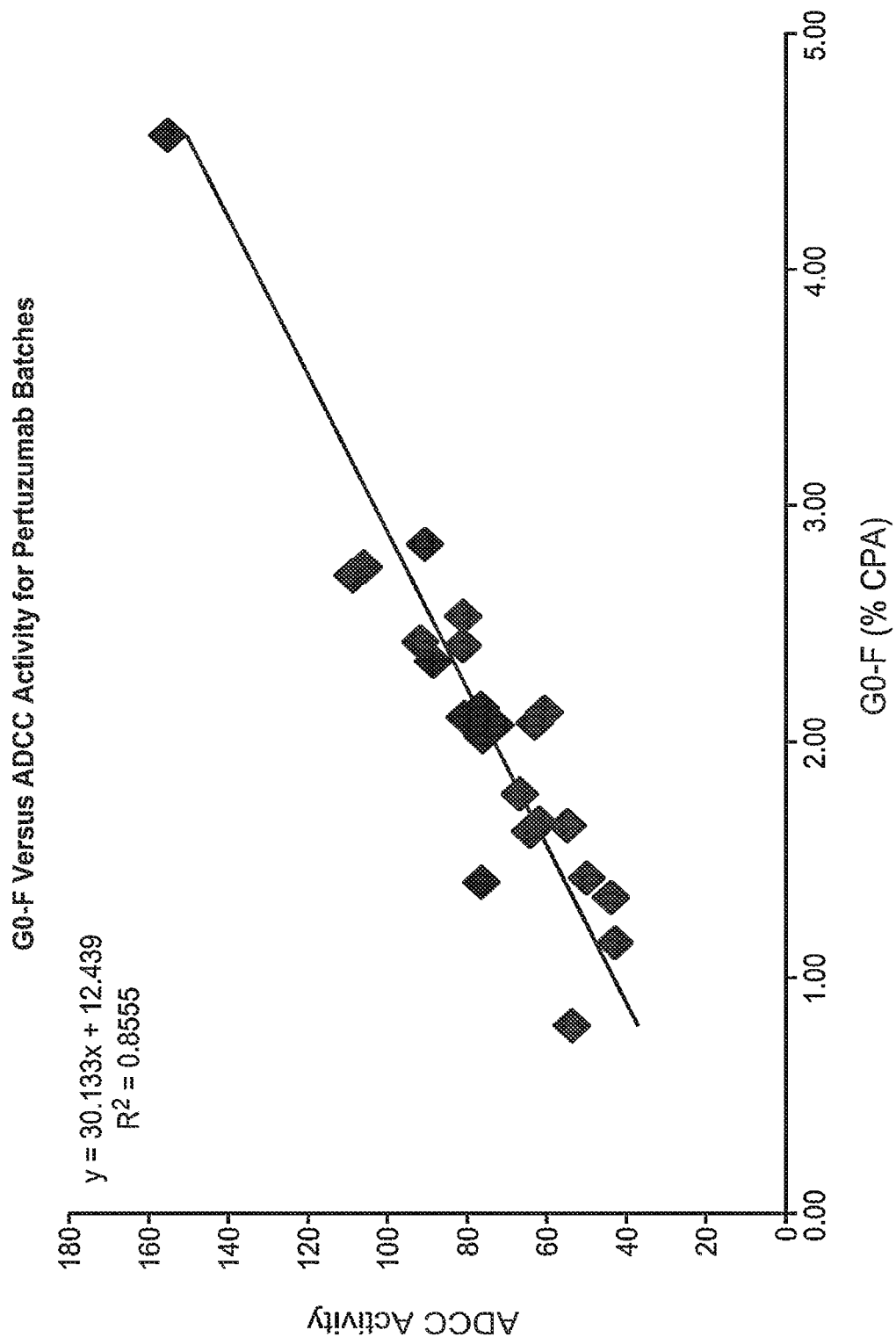
FIG. 21 depicts % G0-F versus ADCC activity for Pertuzumab batches using the assay in Example 4 herein.

Using the assay, a correlation plot is shown in FIG. 21. Using the correlation plot (% ADCC=30.133+12.439x, where x=% G0-F) and an ADCC range of 40-135%, the final specification for Pertuzumab corresponds to 0.9-4.1% G0-F.

Thus, using this validated CE-LIF assay, it is possible to evaluate Pertuzumab compositions to confirm the biological activity in terms of ADCC is within the desired range (40-135% ADCC activity=0.9-4.1% G0-F).

Example 5

Pertuzumab High-Molecular-Weight-Species (HMWS), Low-Molecular-Weight-Species (LMWS) and Characterization Thereof Pertuzumab was analyzed by SE-HPLC and CE-SDS to determine the amount of high-molecular-weight species (HMWS), generally dimer, and low-molecular-weight species (LMWS). There was no difference in HMWS upon dilution, suggesting that the aggregates are non-dissociable. There was good agreement between analytical ultracentrifugation (AUC) and SE-HPLC results in terms of HMWS quantitation, showing no evidence of size-exclusion chromatography missing or underestimating major HMWS.

Materials and Methods

Pertuzumab Compositions Tested: This example describes the characterization of the current Pertuzumab Reference Standard Batch anti2C4907-2 and Run 1, representing Phase III clinical material, and five Phase III/commercial batches (Runs 3-7), all produced at 12,000 liter (L) scale using the commercial process.

Isolated HMWS: To prepare representative HMWS used for biological characterization, a pertuzumab batch from Run 3 was injected onto a preparative HPLC system using a preparative SE-HPLC column (TSK G3000SW, 21.5 mm×600 mm) and the same isocratic mobile phase as described above at 4.5 mL/min. High-molecular-weight species were fraction collected and subsequently buffer exchanged into formulation buffer. HMWS were shown to be 70% pure by subsequent SE-HPLC analysis, with the remainder predominantly main peak. The main peak was also collected and shown to be 100% pure.

Isolated LMWS: To prepare isolated LMWS, a batch Number from Run 3 was digested with papain and subjected to fraction collection using preparative HPLC, as above. The predominant forms were verified to be Fc and Fab by intact ESI-MS analysis. LMWS were shown to be 99% pure by subsequent analytical SE-HPLC. Isolated Fab variants were also prepared using papain treatment and collected by preparative IE-HPLC. The Fab variant was shown to be 100% pure by subsequent analytical SE-HPLC.

SE-HPLC: Aliquots of pertuzumab were diluted to 10 mg/mL with mobile phase (0.2 M potassium phosphate, pH 6.2, 0.25 M potassium chloride). Samples were separated on a TSK G3000SW$_{XL}$ column (7.8 mm×300 mm) that was eluted isocratically. The flow rate was at 0.5 mL/min, and column temperature was at ambient temperature. The elution profile was monitored at 280 nm. For detection by multi-angle light scattering (MALS), pertuzumab samples were separated using two columns in sequence connected inline to a WYATT DAWN HELEO™ MALS detector (using 658 nm laser, 17 detectors) and a WYATT OPTI-LAB™ rex refractive index detector.

CE-SDS: Each Pertuzumab batch was derivatized with 5 carboxytetramethylrhodamine succinimidyl ester, a fluorescent dye. After removing the free dye using NAP-5 columns, non-reduced samples were prepared by adding 40 mM iodoacetamide and heating at 70° C. for 5 minutes. For the analysis of reduced samples, the derivatized pertuzumab was mixed with sodium dodecyl sulfate (SDS) and 1 M DTT to a final concentration of 1% SDS (v/v). Samples were then heated at 70° C. for 20 minutes. The prepared samples were analyzed on a CE system using a 50 μm inner diameter×31.2 cm fused silica capillary maintained at 20° C. throughout the analysis. Samples were introduced into the capillary by electrokinetic injection at 10 kV for 40 seconds. The separation was conducted at a constant voltage of 15 kV in the reversed polarity (negative to positive) mode using CE-SDS running buffer as the sieving medium. An argon ion laser operating at 488 nm was used for fluorescence excitation with the resulting emission signal monitored at 560 nm.

Results and Discussion

Figure 25:
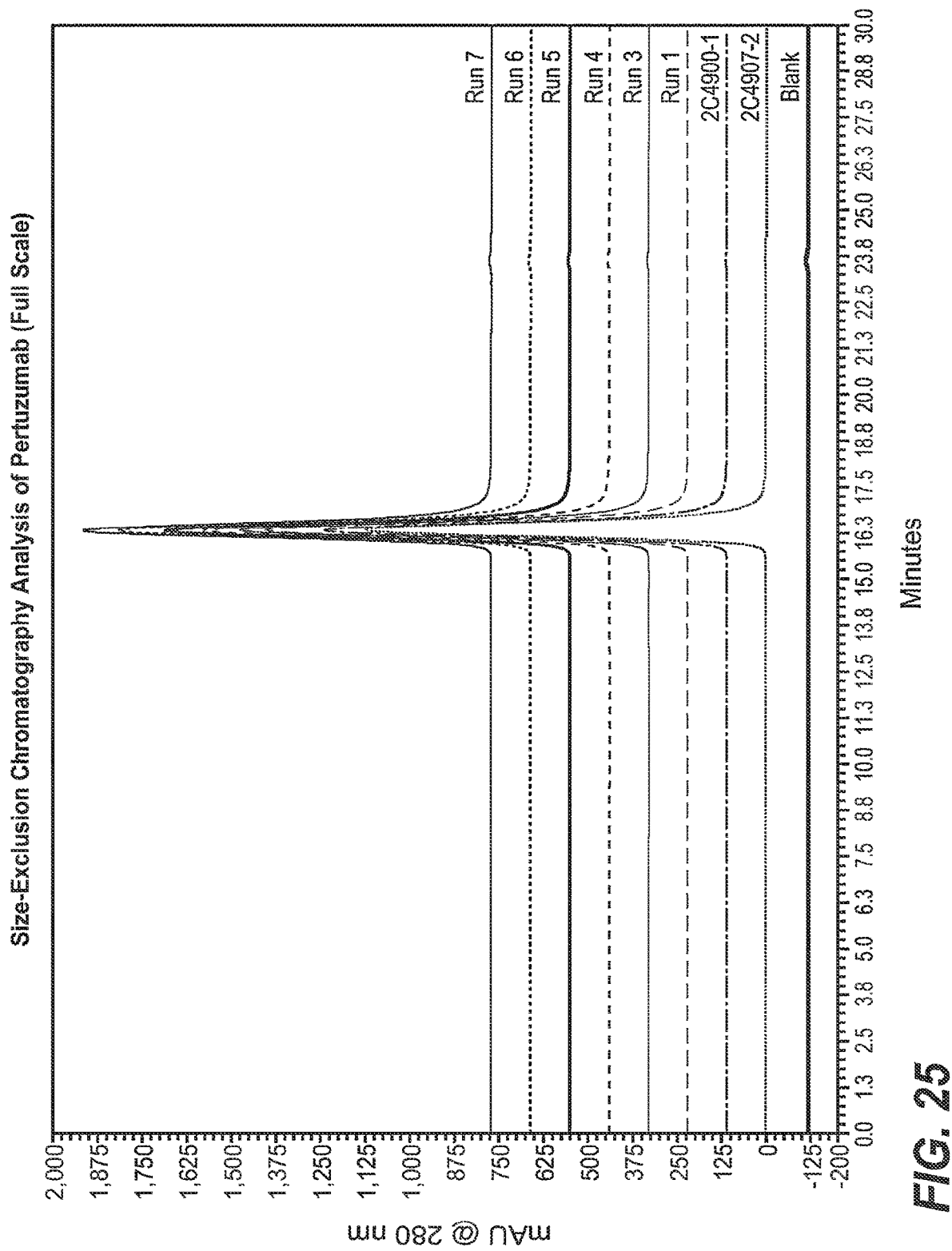
FIG. 25 depicts Size Exclusion Chromatography (SEC) analysis of Pertuzumab (full scale).
Figure 26:
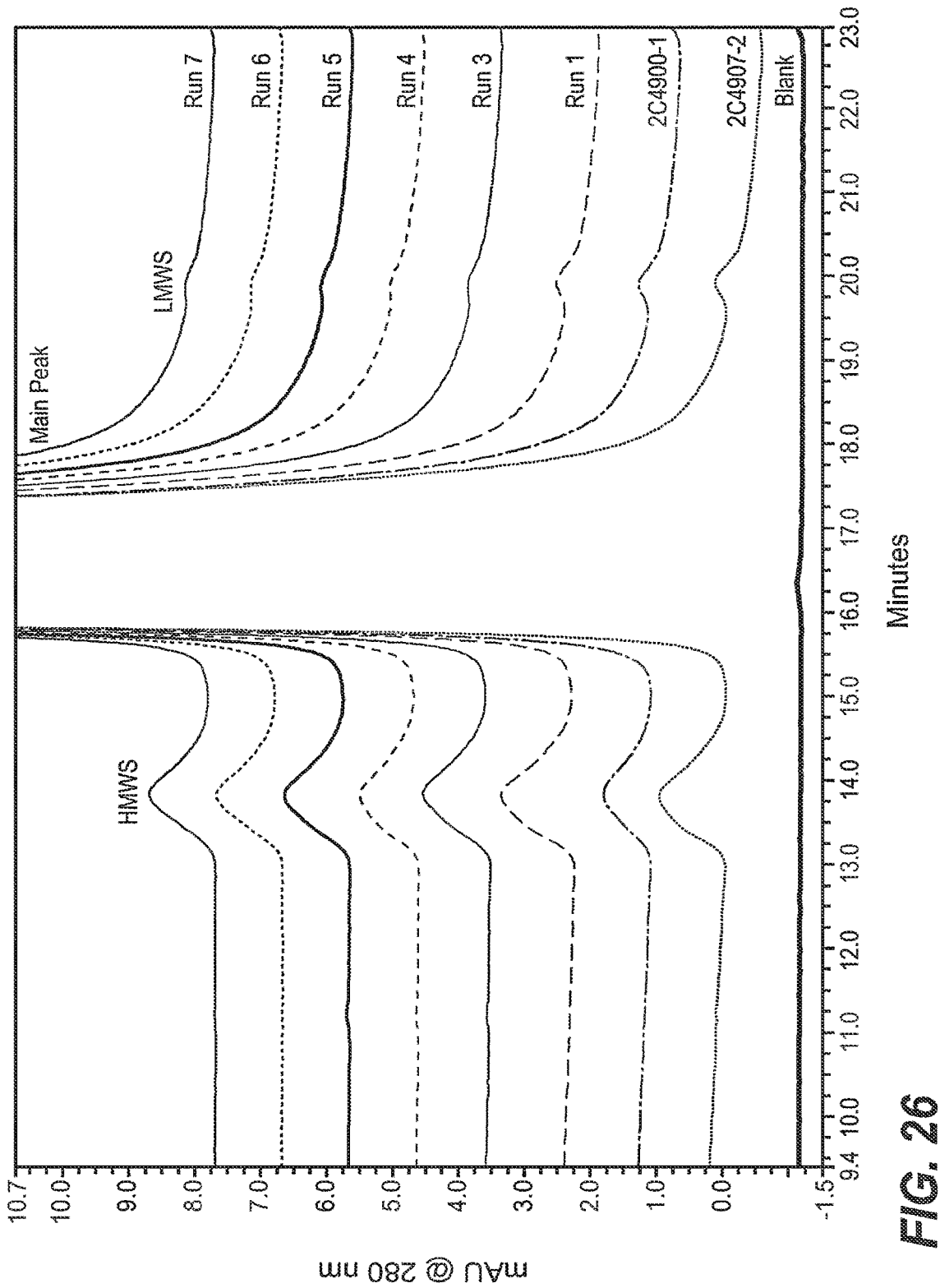
FIG. 26 depicts SEC analysis of Pertuzumab (expanded scale). Peaks include main peak (main species antibody), high molecular weight species (HMWS), and low molecular weight species (LMWS).

SE-HPLC provides quantitative information about the molecular size distribution of a native protein. The SE-HPLC profiles for the pertuzumab batches are shown in FIG. 25, and an expanded view of the profiles is shown in FIG. 26. The relative peak area distribution of size-exclusion peaks is listed in Table 10.

TABLE 10

Relative Size Distribution of Pertuzumab by Size-Exclusion Chromatography

| | Peak | | |
|---|---|---|---|
| Batch Name | HMWS (%) | Main Peak (%) | LMWS (%) |
| anti2C4-900-1 | 0.1 | 99.8 | 0.1 |
| anti2C4907-2[a] | 0.2 | 99.8 | 0.0 |
| Run 1 | 0.2 | 99.8 | 0.0 |
| Run 3 | 0.2 | 99.8 | 0.0 |
| Run 4 | 0.1 | 99.8 | 0.0 |
| Run 5 | 0.2 | 99.8 | 0.0 |
| Run 6 | 0.2 | 99.8 | 0.0 |
| Run 7 | 0.2 | 99.8 | 0.0 |

Note:
The total percent may not add exactly to 100% due to rounding.
HMWS = high-molecular-weight species; LMWS = low-molecular-weight species.
[a]Values obtained from Reference Standard anti2C4907-2.

The proportion of pertuzumab eluting in the main peak was more than 99% for all materials. The amount of high-molecular-weight species (HMWS) ranged from 0.1% to 0.2%, and the low-molecular-weight species (LMWS) was ≤0.1%. All batches displayed similar chromatographic profiles. A purified HMWS fraction, including dimer and higher aggregates, was shown to have 46% potency relative to Reference Standard Batch anti2C4907-2.

SE-HPLC was performed on both neat and diluted samples held at 30° C. to examine pertuzumab HMWS for both fast and slow-dissociating aggregates that could result from dilution and/or prolonged exposure to elevated room temperature. No decrease was seen in the HMWS content of diluted and/or heated Reference Standard Batch anti2C4907-2 as compared to the control.

SE-HPLC separation combined with MALS performed on Reference Standard Batch anti2C4907-2 confirmed the SE-HPLC main peak to be monomer, with a molecular weight of approximately 150 kDa.

AUC in sedimentation velocity mode was used to characterize the HMWS present in pertuzumab samples. Sedimentation velocity is a technique independent from size exclusion chromatography that measures the levels of HMWS in a sample in the absence of a solid column matrix. AUC was performed on pertuzumab samples with increasing levels of HMWS to determine if SE-HPLC is able to detect all major pertuzumab HMWS consistently by comparing the levels and species of aggregates determined by sedimentation velocity to those determined by SE-HPLC. Five samples ranging from 0.2% to 7.2% total HMWS (determined by SE-HPLC) were characterized by sedimentation velocity and labeled A-E in Table 11 and FIG. 27.

These samples consisted of a representative pertuzumab Drug Product batch (labeled A) and four samples with enriched HMWS. The samples with enriched HMWS were chosen to be representative of a wide range of degradation mechanisms (exposure to light, exposure to acidic pH, and purified IE-HPLC basic variants).

Figure 27:
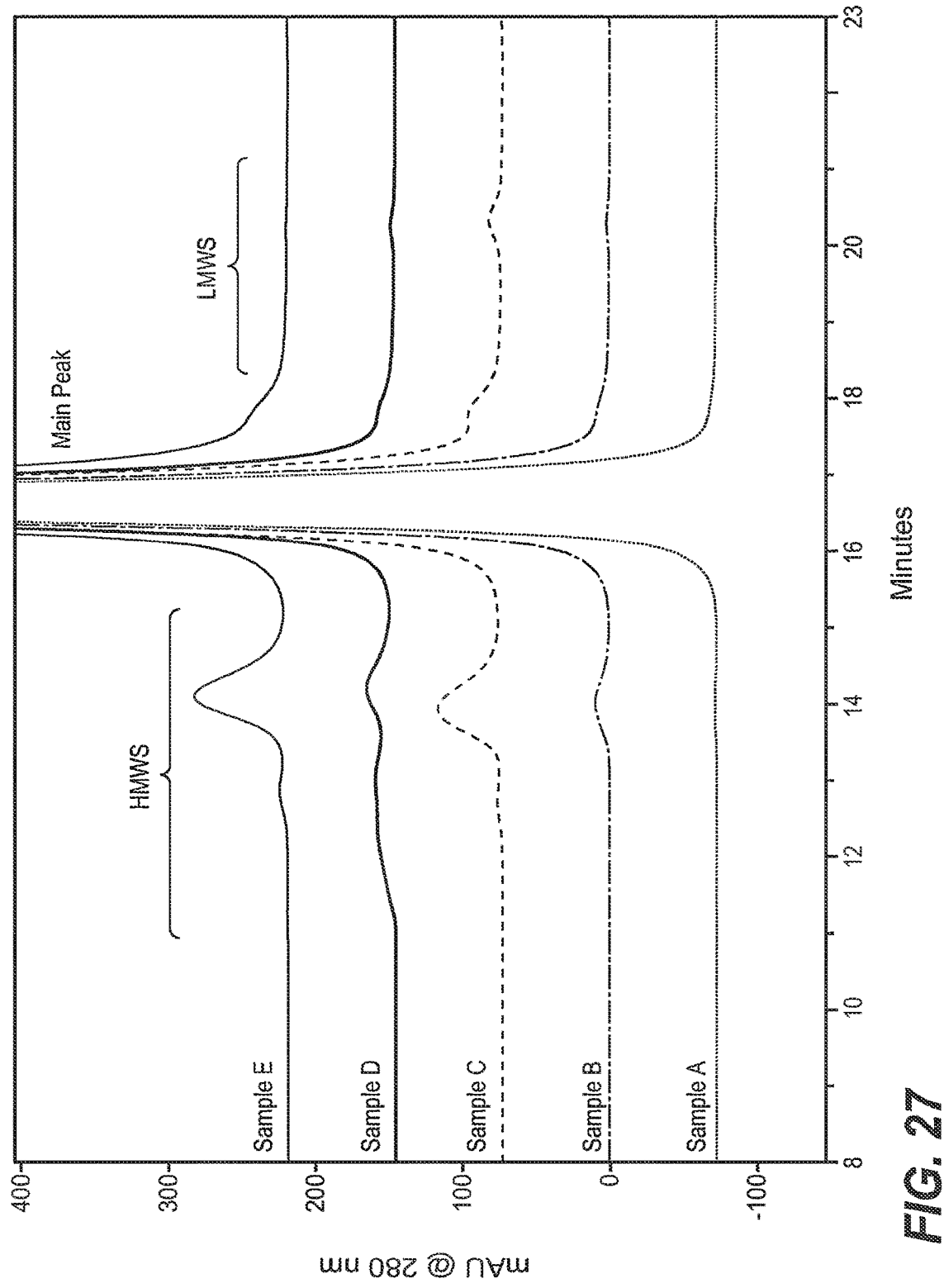
FIG. 27 depicts Size Exclusion-High Performance Liquid Chromatography (SE-HPLC) analysis of Pertuzumab samples. Sample A is representative Pertuzumab Drug Product batch. Sample B is Pertuzumab batch subjected to light exposure at 1.2 mlux hours. Sample C is a Pertuzumab batch subjected to light exposure at 3.6 mlux hours. Sample D is a Pertuzumab batch subjected to acid treatment at pH 3.2. Sample E is purified basic variants from Ion Exchange-HPLC (IE-HPLC).

SE-HPLC shows one major HMWS peak for samples A, B, C and E and two HMWS peaks for sample D (FIG. 27). For samples A, B, C and E, AUC showed only one HMWS peak with a sedimentation coefficient at about 9.1S. In sample D, AUC showed two HMWS peaks with sedimentation coefficients of about 9.1S and 10.8S. The HMWS detected by AUC are consistent with the SE-HPLC results; both methods show one main degradation product, with minor levels of a larger HMWS in sample D.

A comparison of the quantitative results of these samples from the two methods is presented in Table 11.

TABLE 11

Comparison of AUC and SE-HPLC Results

| | % HMWS (total) | |
|---|---|---|
| Sample | AUC | SE-HPLC |
| A | 1.2 [31.4% RSD][a] | 0.2 |
| B | 1.9 | 1.3 |
| C | 4.8 | 5.5 |

TABLE 11-continued

Comparison of AUC and SE-HPLC Results

| | % HMWS (total) | |
| --- | --- | --- |
| Sample | AUC | SE-HPLC |
| D | 6.4 | 6.6 |
| E | 7.6 [7.9% RSD] | 7.2 |

Note 1:
Sample A consists of a representative pertuzumab Drug Product batch, Sample B consists of a pertuzumab batch subjected to light exposure at 1.2 mlux hours, Sample C consists of a pertuzumab batch subjected to light exposure at 3.6 mlux hours, Sample D consists of a pertuzumab batch subjected to acid treatment at pH 3.2, and Sample E consists of purified basic variants from IE-HPLC.

Note 2:
Refer to FIG. 27 for corresponding SE-HPLC chromatograms.

AUC = analytical ultracentrifugation; HMWS = high-molecular-weight species; RSD = relative standard deviation; SE-HPLC = size-exclusion high-performance liquid chromatography.

[a] Samples A and B have HMWS levels that are below the limit of quantitation of the AUC technique.

Figure 28:
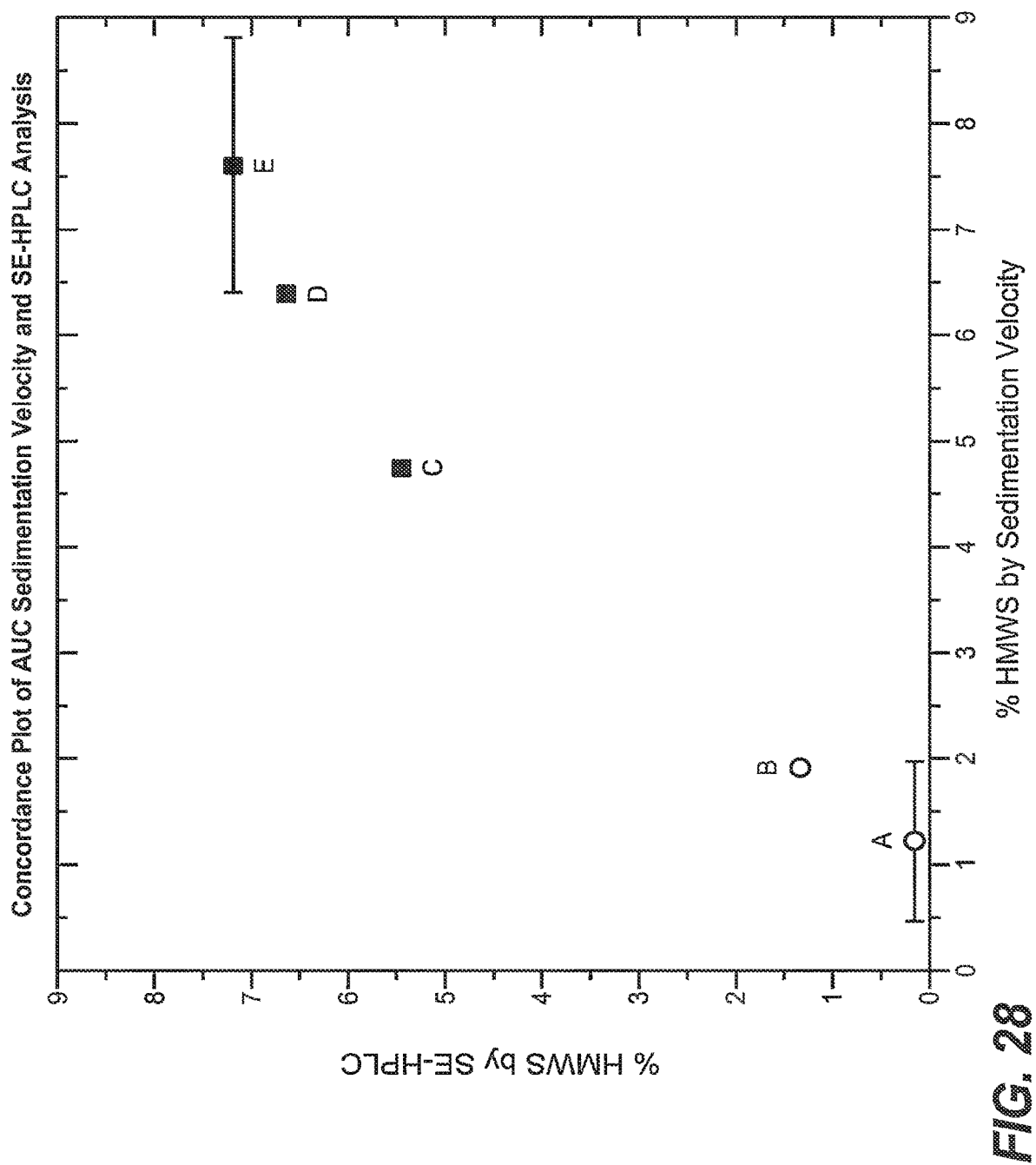
FIG. 28 depicts concordance plot of analytical ultracentrifugation (AUC) sedimentation velocity and SE-HPLC analysis. The error bars represent two standard deviations from n=3 determination. All other data points denote a single determination. Circles denote samples that have HMWS levels below the level of detection of the AUC.

For samples C, D, and E there is good agreement in the percent HMWS measured by both techniques. The low level of HMWS present in samples A and B prevents an accurate quantitation of the species by AUC, which has an estimated Limit of Quantitation of 3.7% (Gabrielson and Arthur, Methods 54:83-91 (2011)). This is reflected by an apparent discrepancy in percent HMWS between SE-HPLC and AUC (Table 11). A correlation across a range of HMWS levels was evaluated. The correlation coefficient (Lin, L, Biometrics 45:255-68 (1989)) was calculated to be 0.97 (n=5) indicating good agreement between AUC and SE-HPLC for the quantitation of HMWS (FIG. 28).

These results confirm that SE-HPLC is robust in measuring HMWS for pertuzumab. SE-HPLC is able to detect and accurately quantitate all HMWS species observed by AUC.

Size-based heterogeneity, analyzed by SE-HPLC, SDS-PAGE, and CE-SDS, was consistent among the batches. The SE-HPLC assay showed similar levels of HMWS (0.1%-0.2%) and LMWS (0.0%-0.1%) for all batches tested. The banding patterns developed by SDS-PAGE analysis for reduced and non-reduced samples were consistent, as were the electrophoretic profiles generated by CE-SDS.

In one embodiment, the amounts of the main species Pertuzumab and HMWS variant and LMWS variant as evaluated by SE-HPLC is as follows:
≥96% Main Peak e.g., ≥96.7% Main Peak, e.g., ≥97.3% Main Peak e.g., ≥97.4% Main Peak ≤2% HMWS, e.g., ≤1.7% HMWS, e.g., ≤1.5% HMWS, e.g., ≤1.4% HMWS, e.g. ≤0.8% HMWS. ≤2% LMWS, e.g., ≤1.6% LMWS, e.g., ≤1.2% LMWS, e.g. ≤0.6% LMWS.

Both the pertuzumab HMWS and LMWS fractions purified by SE-HPLC exhibited a decreased anti-proliferation activity compared to the main peak and control, which was fully potent. All size variants showed comparable HER2 binding activity and FcRn binding activity compared to the control, except for the LMWS, which showed lower FcRn binding. Since the LMWS sample contains ⅔ Fab fragments and ⅓ Fc fragments, the lower anti proliferation and FcRn binding activity are as expected. The HMWS showed higher FcγRIIIa (CD16) V158 binding activity, but lower ADCC activity. The LMWS showed lower FcγRIIIa (CD16) V158 binding activity, and no ADCC activity was observed for this variant (Table 12).

TABLE 12

Biological Activities of Pertuzumab Main Peak, HMWS, and LMWS

| Pertuzumab Samples and Conditions | Mean % Activity (n = 3) | | | | |
| --- | --- | --- | --- | --- | --- |
| | Anti-Proliferation | HER2 Binding | FcγRIIIa Binding | ADCC | FcRn Binding |
| Control | 103 | 108 | 91[b] | 80[b] | 80 |
| Main Peak | 104 | 96 | 96 | 79 | 87 |
| HMWS | 46 | 82 | 522 | 38 | 73 |
| LMWS | 12[a] | 73[a] | 23[a] | No Activity | 7[a] |

Note:
Percent activity reported relative to pertuzumab Reference Standard (Batch anti2C4907-2).
ADCC = antibody-dependent cell-mediated cytotoxicity; HMWS = high-molecular-weight species; LMWS = low-molecular-weight species.
[a] The LMWS sample consist of ⅔ Fab and ⅓ Fc fragments. The value shown reflects nM/nM adjustment based on molecular weight (Fab = 47644 Da, Fc = 52800 Da, and the full length antibody = 148088 Da.
[b] The pertuzumab Reference Standard (Batch anti2C4907-2) has a G0-F level of 2.2%, while the control sample had a G0-F of 1.7%. Results have not been corrected for difference in afucosylated material level.

Figure 29:
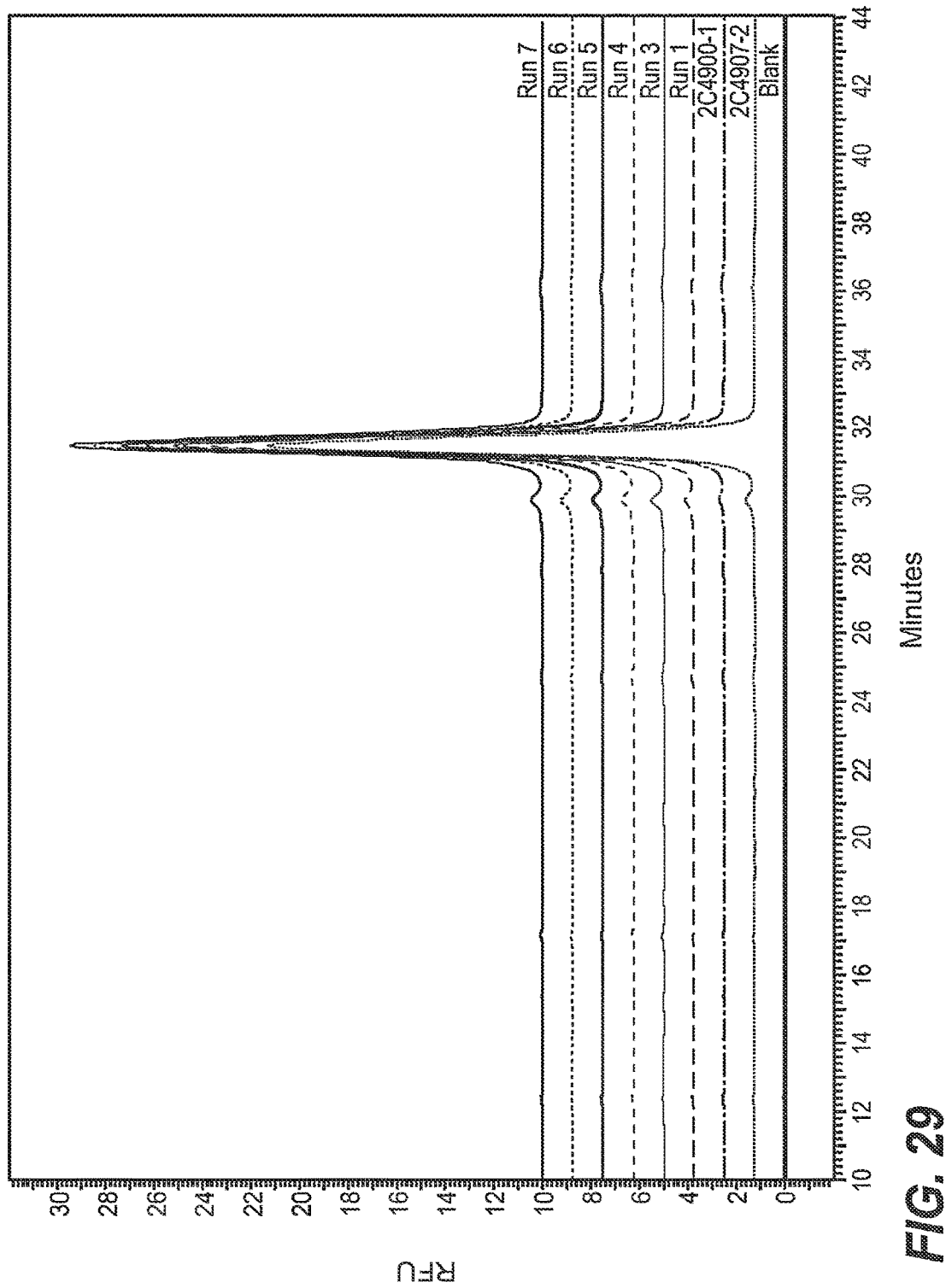
FIG. 29 depicts Capillary Electrophoresis Sodium Dodecyl Sulfate Analysis (CE-SDS) with Laser-Induced Fluorescence (LIF) detection of non-reduced Pertuzumab.
Figure 30:
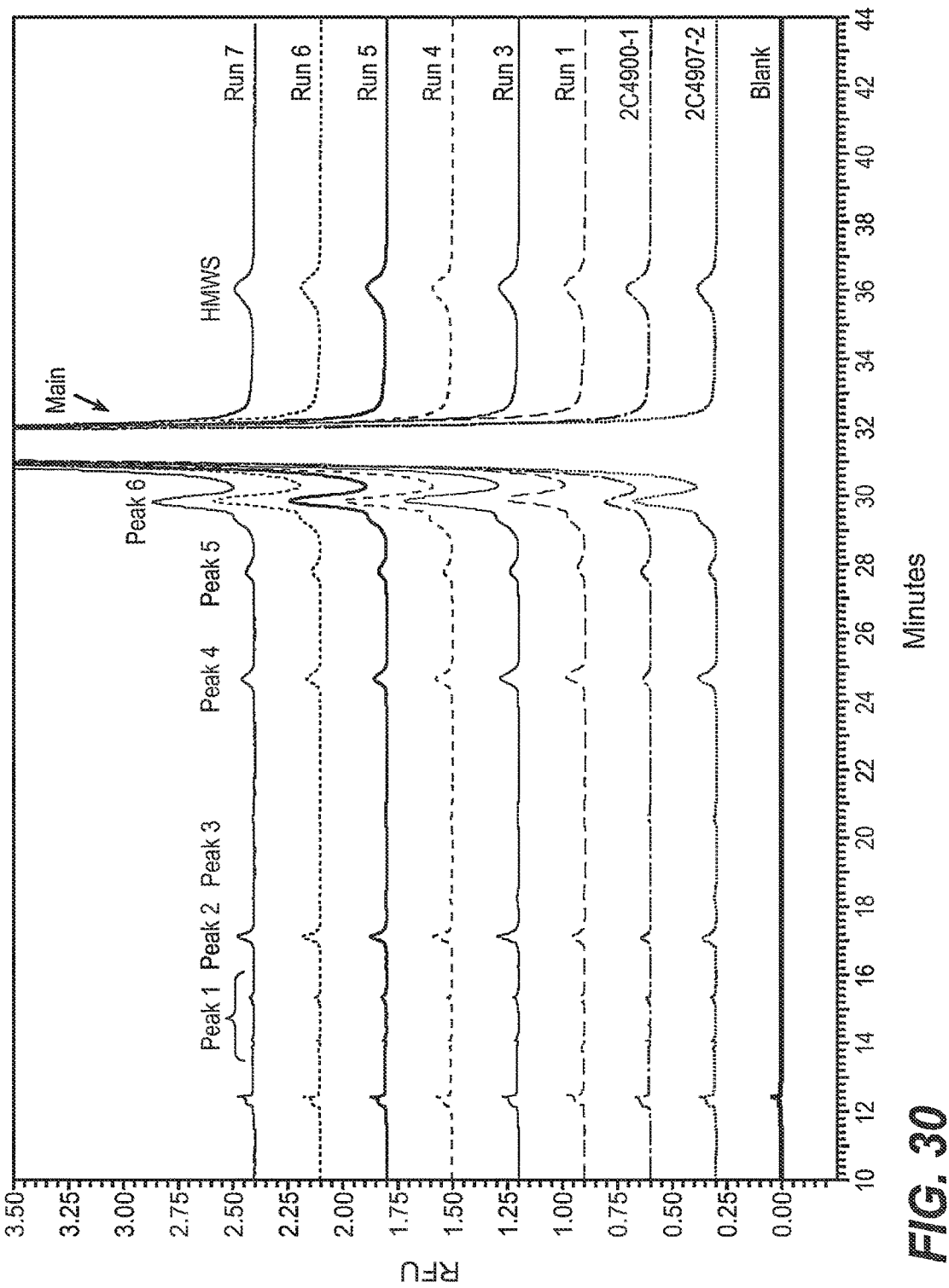
FIG. 30 depicts CE-SDS-LIF of non-reduced (NR) Pertuzumab (expanded view).
Figure 31A:
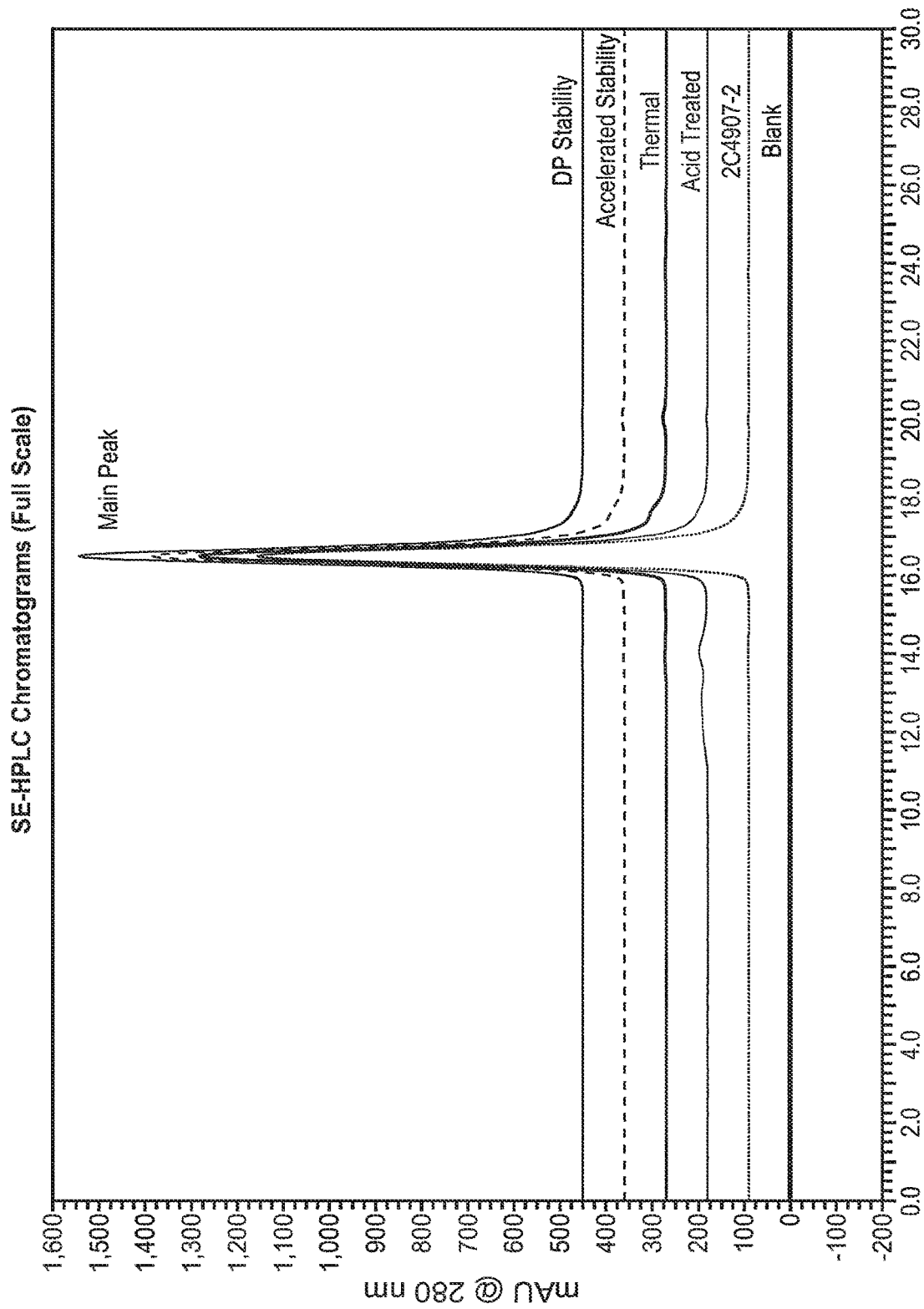
FIGS. 31A and 31B depict SE-HPLC Chromatograms for Example 6: full scale (FIG. 31A) and expanded scale (FIG. 31B).
Figure 31B:
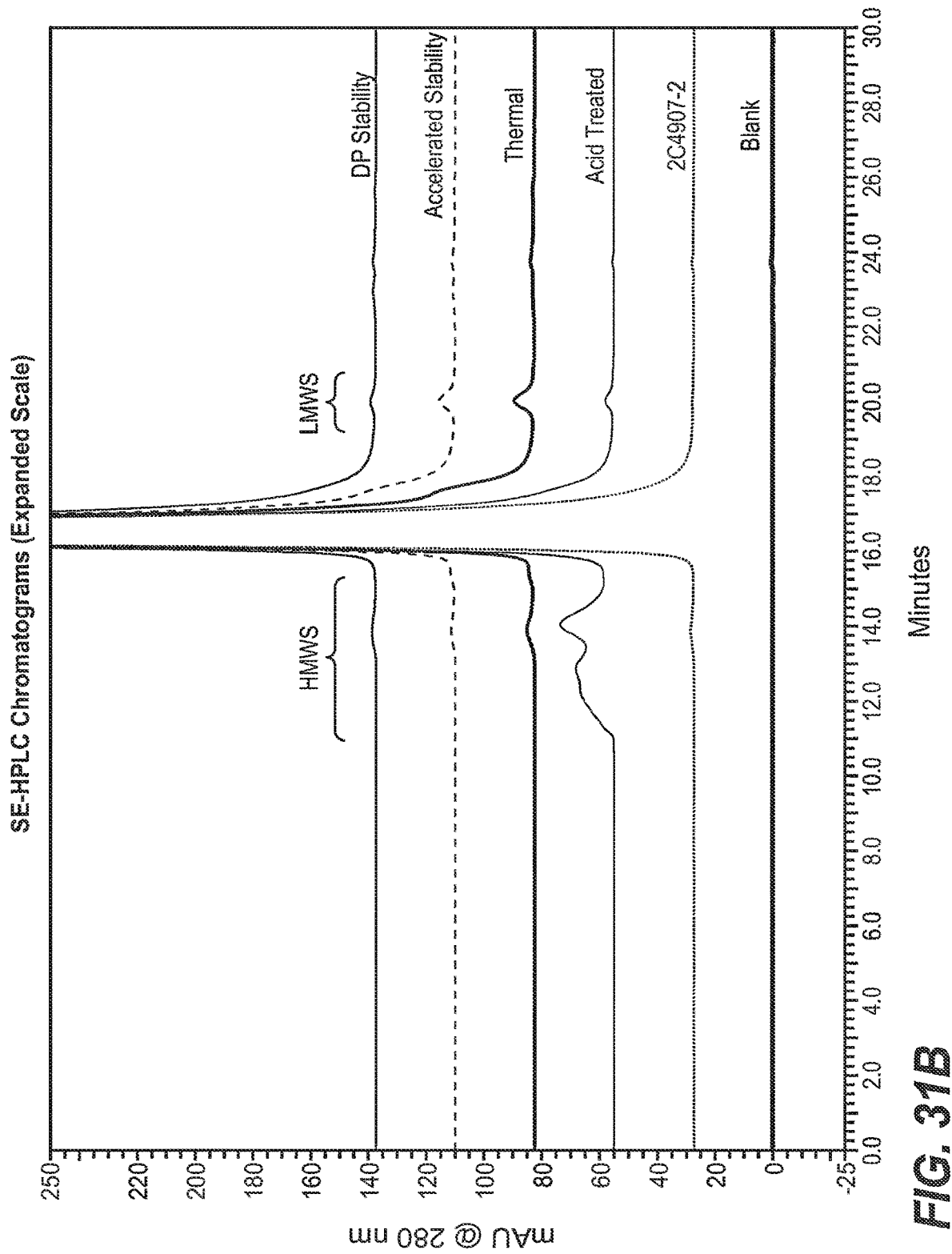
Figure 32A:
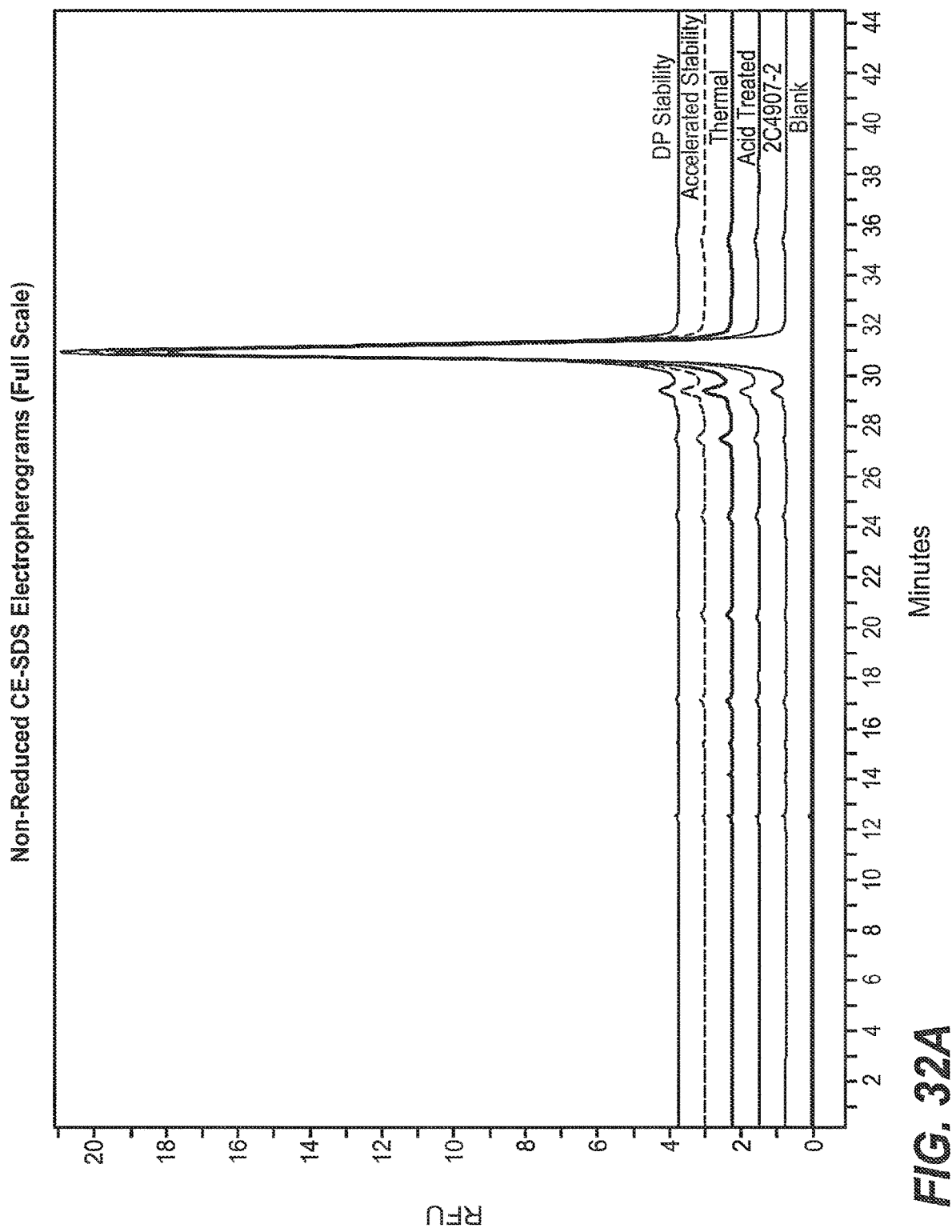
FIGS. 32A and 32B depict non-reduced CE-SDS (NR-CE-SDS) electropherograms for Example 6: full scale (FIG. 32A) and expanded scale (FIG. 32B).
Figure 32B:
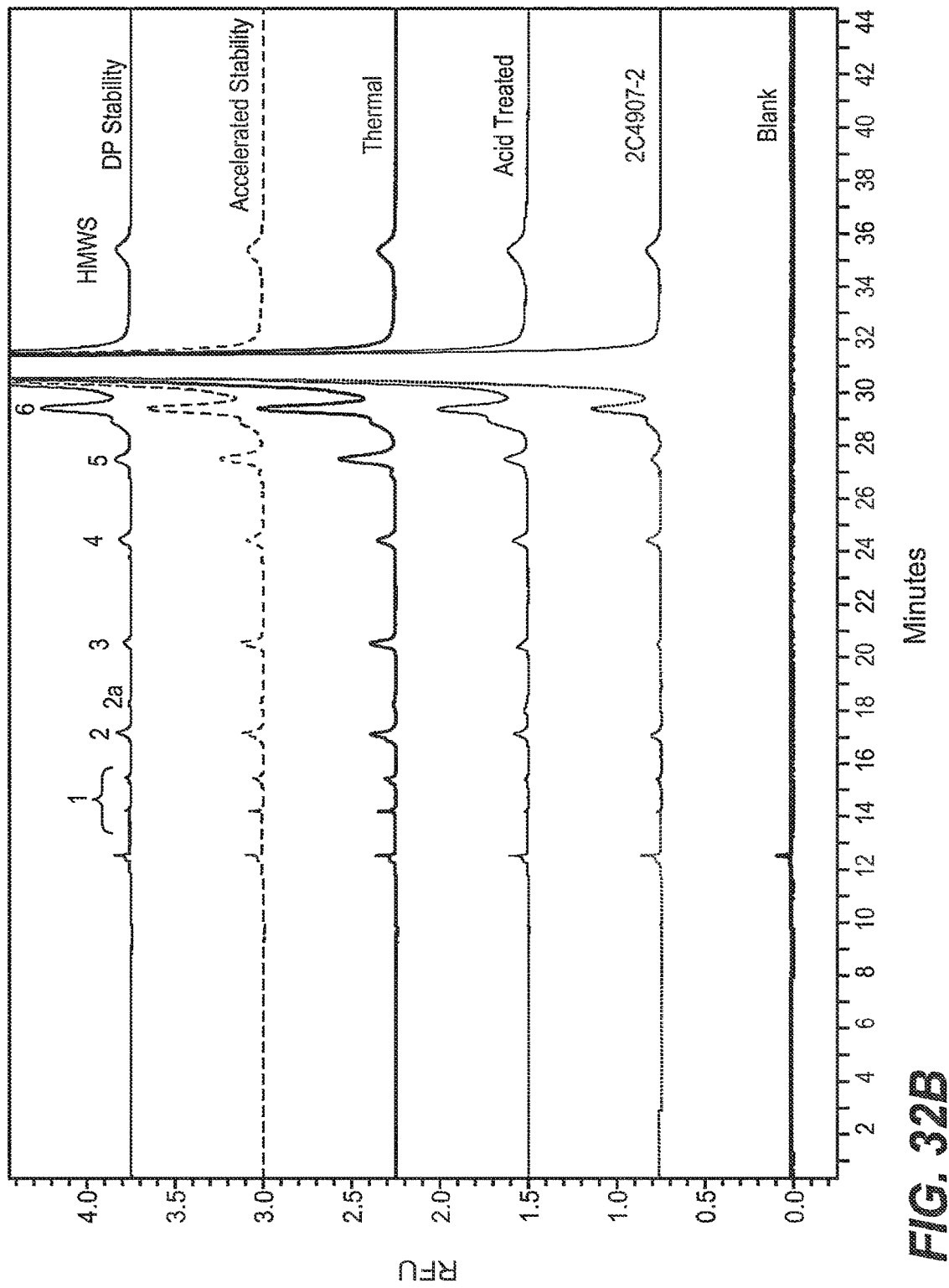

Capillary Electrophoresis Sodium Dodecyl Sulfate (CE-SDS): CE-SDS with laser-induced fluorescence (LIF) detection analysis is a high-sensitivity assay that provides a means of quantitatively assessing the molecular size distribution of proteins under denaturing conditions. In the CE-SDS analysis of non-reduced samples (FIG. 29), pertuzumab migrated as a prominent peak consisting of 96%-98% of the total peak area with minor peaks representing LMWS and HMWS. The amount of HMWS determined by this technique was 0.6% for all materials tested. The remaining species migrated as LMWS as shown in FIG. 30 (expanded view). The sample heating-induced fragmentation is minimized with alkylation (Salas-Solano et al. Anal Chem 78:6583-6594 (2006)). The relative distribution of the species separated by CE-SDS is listed in Table 13.

TABLE 13

Relative Distribution of Non-Reduced Pertuzumab by CE-SDS (Percent Peak Area)

| Batch Name | Peak | | | | | | | |
| --- | --- | --- | --- | --- | --- | --- | --- | --- |
| | 1 | 2 | 3 | 4 | 5 | 6 | Main | HMWS |
| anti2C4-900-1 | 0.1 | 0.2 | 0.1 | 0.2 | 0.2 | 0.9 | 97.8 | 0.6 |
| anti2C4907-2 | 0.1 | 0.3 | 0.1 | 0.3 | 0.2 | 1.9 | 96.5 | 0.6 |
| Run 1 | 0.1 | 0.3 | 0.1 | 0.4 | 0.2 | 1.7 | 96.7 | 0.6 |
| Run 3 | 0.1 | 0.4 | 0.1 | 0.3 | 0.2 | 2.3 | 96.0 | 0.6 |
| Run 4 | 0.1 | 0.4 | 0.1 | 0.3 | 0.2 | 2.3 | 96.1 | 0.6 |
| Run 5 | 0.1 | 0.3 | 0.1 | 0.2 | 0.2 | 2.0 | 96.4 | 0.6 |
| Run 6 | 0.1 | 0.4 | 0.1 | 0.3 | 0.2 | 2.2 | 96.2 | 0.6 |
| Run 7 | 0.1 | 0.4 | 0.0 | 0.2 | 0.2 | 2.1 | 96.3 | 0.6 |

Note:
The total % may not add exactly to 100% due to rounding.
CE-SDS = capillary electrophoresis sodium dodecyl sulfate;
HMWS = high-molecular-weight species.

A minor difference was observed wherein Peak 6 increased from 0.9% in the Reference Standard Batch anti2C4-900-1 (Phase I/II process) to 1.7%-2.3% for Reference Standard Batch anti2C4907-2, Run 1, and Runs 3-7.

In one embodiment, the Pertuzumab main peak (excluding LMWS and HMWS) as separated or isolated by NR-CE-SDS is from about 95% to about 99%, e.g., from about 96.0% to about 97.8%. Optionally, the amount of HMWS is ≤1%, e.g. ≤0.6% and the amount of LMWS is ≤4%, e.g. ≤3.4% as separated or isolated by CE-SDS.

Example 6

Detection and Quantification of Pertuzumab Fragmentation

The purpose of this example was to evaluate size exclusion chromatography (SE-HPLC), reduced capillary electrophoresis sodium dodecyl sulfate (R-CE-SDS), and non-reduced CE-SDS (NR-CE-SDS) methods for the detection of pertuzumab fragments.

Materials and Methods

Samples evaluated in this study are summarized below. These include pertuzumab samples that have been subjected to various stressed conditions which might result in increased fragmentation.

Reference Standard (2C4907-2)
Thermally stressed (42 days, 40° C.)
Acid treated (pH 3.2, 1 day, 40° C.)
Accelerated stability (30 days at 40° C. then stored at approximately 5° C.)
Real time Drug Product (DP) stability (T=0 and T=548 days and stored at approximately 5° C.) and corresponding Drug Substance (DS)

SE-HPLC was carried out as described in Example 5 above, with the following reportable values: LMWS, Main Peak, HMWS, and all other significant peaks above limit of quantification (LOQ).

Reduced CE-SDS (R-CE-SDS) was carried out according to Example 5 above, with reportable values: Peak 1, LC, Peak 2, Peak 3, NGHC, HC, Peak 5, Inc. Red., and other significant peaks above LOQ.

Non-reduced CE-SDS (NR-CE-CDS) was carried out as in Example 5 above, with sample preparation excluding the antibody reduction step to allow non-reduced analysis by eliminated dithiothreitol (DTT) from the SDS complexation step.

Qualitative results obtained by SE-HPLC, NR-CE-SDS, and R-CE-SDS are presented in FIGS. 31A-B, FIGS. 32A-B, and FIGS. 33A-B, respectively, as well as Tables 14, 15, and 16, respectively.

Peak identifications are based on Hunt & Nashabeh *Analytical Chemistry* 71: 2390-2397 (1999), and Ma & Nashabeh *Chromatographia Supplement* 53: S75-S89 (2001). For NR-CE-SDS analysis, a small peak after Peak 2 is typically included as part of Peak 2 during data reporting. For this study, this small peak is reported separately as Peak 2a to differentiate the fragment from light chain (LC).

TABLE 14

SE-HPLC Quantitative Data (% Peak Area)

|  | HMWS (%) | Main Peak (%) | LMWS (%) |
|---|---|---|---|
| 2C4907-2 | 0.18 | 99.77 | 0.04 |
| Thermal | 0.40 | 98.96 | 0.64 |
| Acid Treated | 7.09 | 92.65 | 0.26 |
| Accelerated Stability | 0.26 | 99.23 | 0.51 |
| DP Stability | 0.19 | 99.68 | 0.13 |

TABLE 15

NR-CE-SDS Quantitative Data (% CPA)

|  | Peak 1 | Peak 2 (LC) | Peak 2a | Peak 3 (Fab) | Peak 4 (HL) | Peak 5 (HH/des Fab) | Peak 6 (HHL) | Main Peak | HMWS |
|---|---|---|---|---|---|---|---|---|---|
| 2C4907-2 | 0.12 | 0.29 | 0.05 | 0.07 | 0.35 | 0.18 | 1.90 | 96.32 | 0.73 |
| Thermal | 0.42 | 0.70 | 0.09 | 0.61 | 0.52 | 1.36 | 3.62 | 91.99 | 0.71 |
| Acid Treated | 0.15 | 0.37 | 0.17 | 0.35 | 0.45 | 0.66 | 3.19 | 93.42 | 1.25 |
| Accel. Stability | 0.35 | 0.59 | 0.09 | 0.48 | 0.44 | 1.07 | 3.25 | 92.90 | 0.84 |
| DP Stability | 0.22 | 0.37 | 0.06 | 0.20 | 0.33 | 0.43 | 2.53 | 95.27 | 0.60 |

LC = Light Chain,
HC = Heavy Chain,
L = Light,
H = Heavy

TABLE 16

R-CE-SDS Quantitative Data (% CPA)

|  | Peak 1 | LC | Peak 2 | Peak 3 | NGHC | HC | Peak 5 | Inc. Red. |
|---|---|---|---|---|---|---|---|---|
| 2C4907-2 | 0.31 | 25.30 | 0.92 | 2.44 | 2.81 | 66.82 | 0.48 | 0.91 |
| Thermal | 0.54 | 26.16 | 1.12 | 3.13 | 2.81 | 64.54 | 0.27 | 1.43 |
| Acid Treated | 0.38 | 25.04 | 5.58$^c$ | 2.77 | 2.41 | 62.91 | 0.19 | 0.71 |
| Accel. Stability | 0.51 | 25.01 | 0.98 | 2.99 | 3.16 | 66.10 | 0.25 | 1.03 |
| DP Stability | 0.19 | 26.34 | 0.69 | 3.21 | 2.83 | 65.93 | 0.24 | 0.57 |

NGHC = Non-Glycosylated Heavy Chain,
HC = Heavy Chain,
Inc. Red. = Incompletely Reduced Data Evaluation: The percent peak area (or percent corrected peak area, % CPA, for CE-SDS) of relevant fragments was compared to determine if either of the CE-SDS methods provide non-redundant information as compared to SE-HPLC. Relevant fragments include peaks with unknown structure, or those that are known to contain products derived from cleavage of polypeptide chain(s). These fragments are distinct from the dissociable non-disulfide bonded heavy and/or light chain fragments that are present in antibody products and are commonly observed by CE-SDS. Fragment peaks must be resolved from other peaks to enable sensitive detection and accurate quantitation.

Ability to Detect Small Fragments: Small fragments can be observed in both R-CE-SDS and NR-CE-SDS analysis, and are named as Peak 1 in both assays. These peaks retain the same general shape and migration time, and increase similarly under stressed conditions in both assays. Therefore, Peak 1 is presumed to contain the same species in both assays. Both CE-SDS assays are capable of detecting small fragments, as noted in Table 17.

Figure 34:
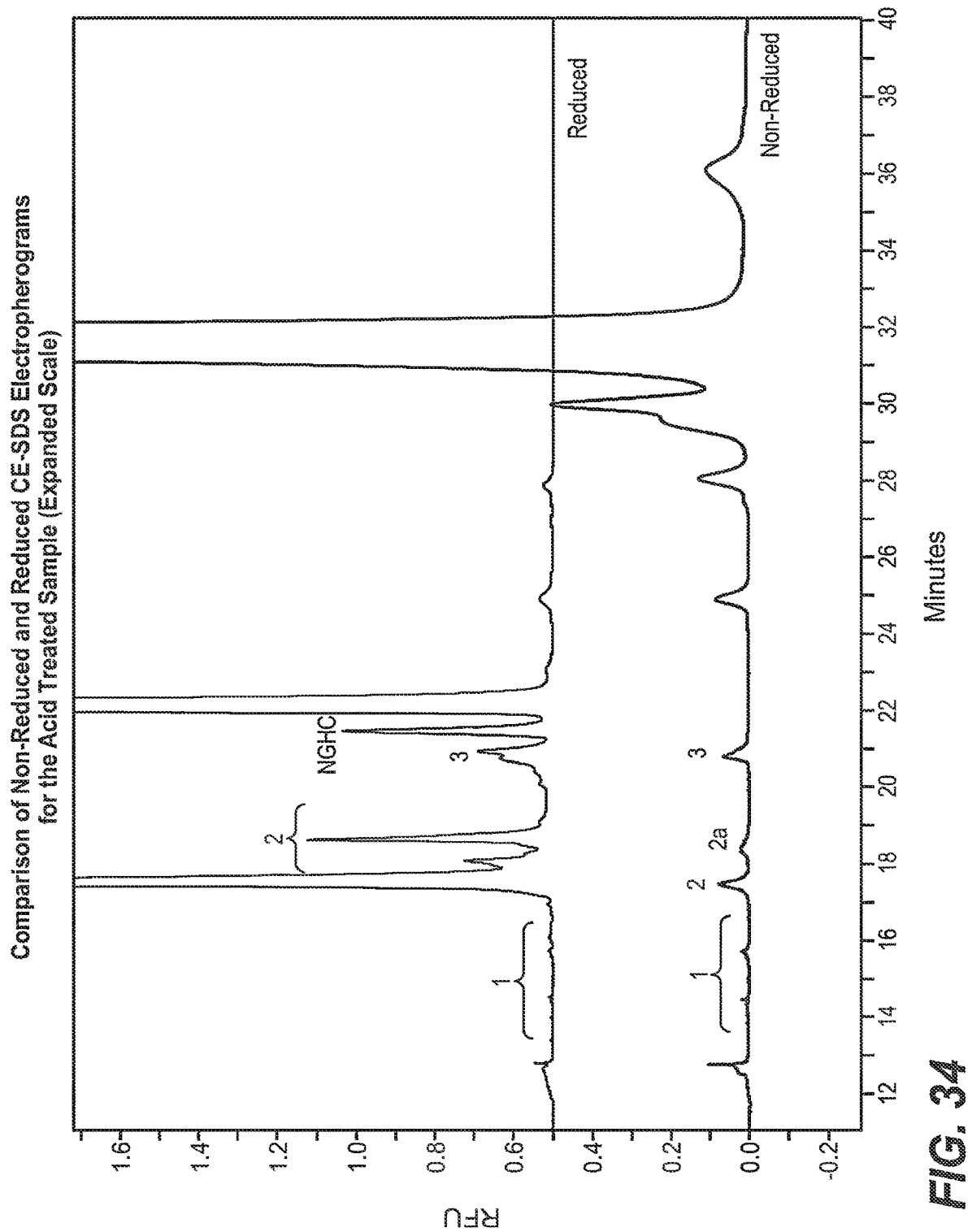
FIG. 34 provides a comparison of NR-CE-SDS and R-CE-SDS electropherograms for an acid treated sample (expanded scale).

Ability to Detect Fragments Generated by Acid Hydrolysis (Acid Clips): Prolonged exposure to acidic conditions can generate fragments, particularly at the Asp-Pro sequence (pertuzumab heavy chain residues 272-273), as supported by mass spectrometric analysis of the acid-treated sample showing masses at 29039 Da (HC 1-272) and 21513 Da (HC 273-448 with G0 glycan). The theoretical masses for these forms are 29031 Da and 21510 Da, respectively. Based on the expected migration time of these forms, a corresponding peak can be seen clearly in the reduced CE-SDS analysis of the acid treated sample (Peak 2, FIG. 34), but is detected at a much lower level (lower signal) in the non-reduced assay. It can be postulated that in the NR-CE-SDS assay the Peak 2 fragment is presumably disulfide linked, and therefore not detected. Since the level of Peak 2 detected by R-CE-SDS (5.58%) in the acid-treated sample exceeds the total LMWS as detected by SE-HPLC (0.26%) for this sample, it can be concluded that SE-HPLC is also insufficient for detection of these forms. Therefore, the reduced CE-SDS assay is the only assay presented herein capable of detecting fragmentation generated as a result of acid hydrolysis, as noted in Table 17.

Figure 35:
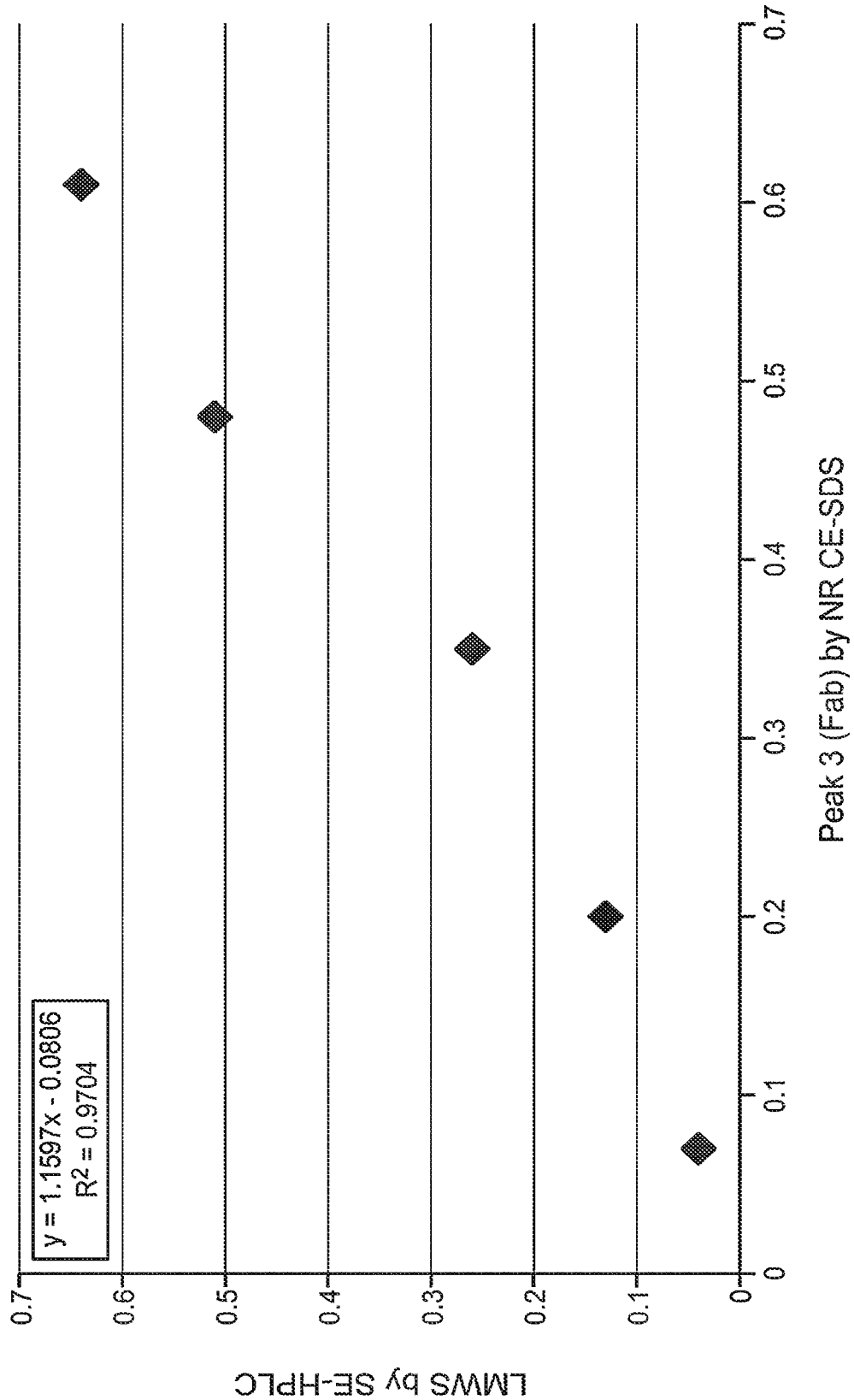
FIG. 35 depicts correlation of Fab quantitation between NR-CE-SDS and SE-HPLC.

Ability to Detect Fab/DesFab Fragments: There is a good linear correlation ($r^2$=0.97) between the LMWS as detected by SE-HPLC, and Peak 3 from the non-reduced CE-SDS assay (FIG. 35). The LMWS was identified to contain the Fab fragment through co-elution studies with enzymatically generated Fab. Similarly, Peak 3 and Peak 5 in the NR-CE-SDS assay were identified through co-migration studies with enzymatically generated Fab and DesFab, respectively (Ma & Nashabeh, supra). The desFab peak arises from the heavy chain cleavage that produced the Fab form, so it is presumed to be in a an equivalent molar quantity (corresponds to a 2:1 mass ratio) relative to the Fab fragment, and thus, information on this form can also be indirectly obtained by SE-HPLC as noted in Table 17.

TABLE 17

Detection Capability for Fragments by SE-HPLC, NR-CE-SDS, and R-CE-SDS

| Fragment | SE-HPLC | NR-CE-SDS | R-CE-SDS |
|---|---|---|---|
| Small Fragments CE-SDS Peak 1 | Unknown | Yes | Yes |
| Acidic Clips (R-CE-SDS Peak 2) | No | No | Yes |
| Fab/DesFab | Yes/(indirectly) | Yes | No |

Reduced CE-SDS Peak 3: R-CE-SDS Peak 3 is unique for pertuzumab and has not been observed in the CE-SDS analysis of other antibodies. Extended characterization results support the conclusion that Peak 3 is not a product variant or impurity, but rather a method-induced artifact specific to pertuzumab consisting of a dissociable form of LC-LC dimer. Multiple techniques were employed to characterize Peak 3.

Peak 3 is observed by R-CE-SDS with UV and LIF detection, suggesting it is not a dye-labeling or sample preparation artifact.

Upon analysis by R-CE-SDS, purified pertuzumab light chain fractions produce Peak 3 having an apparent MW approximately 2-times the theoretical size of LC.

Peak 3 is not observed when the electrophoretic conditions include a higher capillary temperature, and no other co-migrating fragments are observed under these conditions.

Studies involving single amino acid mutations have identified three amino acid residues in LC CDR1 and CDR2 correlated with LC-LC dimer formation. When any of these three residues is replaced by another amino acid, Peak 3 completely dissociates and is no longer observed by reduced CE-SDS.

SDS-PAGE analysis coupled with MALDI-TOF Protein Mass Fingerprinting (PMF) confirmed no host cell proteins were present in pertuzumab, nor was an analogous band detected at levels observed by CE-SDS.

Taken collectively, these results support the identification of Peak 3 as a method-induced, LC-LC dimer specific to pertuzumab.

Discussion

Evaluation of data obtained from this study indicates that:
(1) NR-CE-SDS does provide non-redundant information as compared to SE-HPLC for the detection of fragments
(2) The non-redundant fragmentation information obtained by the NR-CE-SDS method (as compared to SE-HPLC) can also be obtained using the R-CE-SDS method As shown in Table 16, the reduced assay detected cleavage products resulting from low pH exposure, which may occur during Drug Substance manufacture. Table 18 contains the values obtained for reduced CE-SDS Peak 1 and Peak 2 for pertuzumab reference standard, phase III material (n=3), and batches produced using the commercial manufacturing process (n=39). The 95/99 tolerance intervals (TIs) have been calculated for Peak 1 and Peak 2 using a k value of 3.2, and are presented in Table 18. The 95/99 tolerance interval for Peak 1 is 0.0 to 0.4% CPA. The 95/99 tolerance interval for Peak 2 is 0.3 to 0.9% CPA.

TABLE 18

R-CE-SDS Quantitative Data (% CPA) on 43 Batches Tested

| n | Batch | Peak 1 (% CPA) | Peak 2 (% CPA) |
|---|---|---|---|
| 1 | anti2C4907-2 | 0.31 | 0.92 |
| 2 | SSF0001 | 0.25 | 0.63 |
| 3 | SSF0002 | 0.20 | 0.62 |
| 4 | SSF0003 | 0.27 | 0.60 |
| 5 | VV0002 | 0.27 | 0.47 |
| 6 | VV0003 | 0.28 | 0.49 |
| 7 | VV0004 | 0.25 | 0.51 |
| 8 | VV0005 | 0.41 | 0.55 |
| 9 | VV0006 | 0.27 | 0.50 |
| 10 | VV0007 | 0.29 | 0.50 |
| 11 | VV0008 | 0.30 | 0.53 |
| 12 | VV0009 | 0.26 | 0.54 |
| 13 | VV0013 | 0.19 | 0.54 |
| 14 | VV0018 | 0.17 | 0.56 |
| 15 | VV0020 | 0.17 | 0.58 |
| 16 | VV0021 | 0.18 | 0.62 |
| 17 | VV0023 | 0.14 | 0.62 |
| 18 | VV0024 | 0.13 | 0.64 |
| 19 | VV0025 | 0.18 | 0.69 |
| 20 | VV0026 | 0.13 | 0.58 |
| 21 | VV0028 | 0.17 | 0.60 |
| 22 | VV0029 | 0.18 | 0.61 |
| 23 | VV0031 | 0.18 | 0.65 |
| 24 | VV0032 | 0.16 | 0.69 |
| 25 | VV0033 | 0.18 | 0.69 |

TABLE 18-continued

R-CE-SDS Quantitative Data (% CPA) on 43 Batches Tested

| n | Batch | Peak 1 (% CPA) | Peak 2 (% CPA) |
|---|---|---|---|
| 26 | VV0034 | 0.18 | 0.67 |
| 27 | VV0035 | 0.17 | 0.59 |
| 28 | VV0036 | 0.17 | 0.67 |
| 29 | VV0037 | 0.19 | 0.74 |
| 30 | VV0038 | 0.19 | 0.71 |
| 31 | VV0039 | 0.19 | 0.73 |
| 32 | VV0040 | 0.19 | 0.70 |
| 33 | VV0041 | 0.18 | 0.72 |
| 34 | VV0042 | 0.19 | 0.73 |
| 35 | VV0043 | 0.19 | 0.61 |
| 36 | VV0044 | 0.20 | 0.67 |
| 37 | VV0046 | 0.20 | 0.62 |
| 38 | VV0047 | 0.22 | 0.66 |
| 39 | VV0048 | 0.22 | 0.63 |
| 40 | VV0049 | 0.20 | 0.69 |
| 41 | VV0050 | 0.18 | 0.49 |
| 42 | VV0051 | 0.16 | 0.63 |
| 43 | VV0052 | 0.18 | 0.60 |
| | Mean | 0.21 | 0.62 |
| | Standard Deviation | 0.06 | 0.09 |
| | Minimum | 0.13 | 0.47 |
| | Maximum | 0.41 | 0.92 |
| | N | 43 | 43 |
| | K | 3.2 | 3.2 |
| | Lower TI | 0.02 | 0.33 |
| | Upper TI | 0.40 | 0.91 |

A final acceptance criteria of Peak 1≤0.5% and Peak 2≤1.0% on Drug Substance release is selected herein.

As the pertuzumab Drug Substance is stored frozen, there would be no expected changes on DS stability. In addition, based on R-CE-SDS data obtained for Drug Product at both T=0 and T548d (Table 19), no significant change is observed for any of the named species.

TABLE 19

R-CE-SDS Quantitative Data (% CPA) for a DP Stability Sample

| | Peak 1 | LC | Peak 2 | Peak 3 | NGHC | HC | Peak 5 | Inc. Red. |
|---|---|---|---|---|---|---|---|---|
| DS Release | 0.25 | 26.72 | 0.51 | 2.27 | 2.76 | 66.66 | 0.27 | 0.56 |
| DP Stability T = 0 | 0.13 | 26.45 | 0.54 | 2.78 | 2.78 | 66.53 | 0.30 | 0.49 |
| DP Stability T = 548 d | 0.19 | 26.34 | 0.69 | 3.21 | 2.83 | 65.93 | 0.24 | 0.57 |

NGHC = Non-Glycosylated Heavy Chain,
HC = Heavy Chain,
Inc. Red. = Incompletely Reduced

---

What is claimed is:

1. A method of making an article of manufacture comprising a Pertuzumab pharmaceutical composition suitable for treating a cancer patient, comprising:
   (1) recombinantly expressing Pertuzumab from recombinant Chinese Hamster Ovary (CHO) cells at manufacturing scale, and purifying a Pertuzumab composition;
   (2) analyzing fragmentation at Asp-Pro Pertuzumab heavy chain residues 272-273 comprising measuring and identifying the presence of Peak 2 fragment in an amount from 0.3% to 0.9% by reduced capillary electrophoresis sodium dodecyl sulfate (R-CE-SDS) assay in the purified Pertuzumab composition;
   (3) combining the purified Pertuzumab composition with one or more pharmaceutically acceptable excipients to make a pharmaceutical composition, wherein step (3) is before or after step (2); and
   (4) preparing an article of manufacture comprising a container with the pharmaceutical composition therein, and a package insert with prescribing information instructing the user thereof to use the pharmaceutical composition to treat a cancer patient.

2. The method of claim 1, further comprising measuring Peak 1 fragment in an amount ≤0 0.5% by R-CE-SDS assay in the purified Pertuzumab composition.

3. The method of claim 2, wherein the amount of Peak 1 fragment measured is from 0.02% to 0.4%.

* * * * *